(12) United States Patent
Lovell et al.

(10) Patent No.: US 10,918,599 B2
(45) Date of Patent: Feb. 16, 2021

(54) SERUM-STABLE COMPOSITIONS AND METHODS FOR LIGHT-TRIGGERED RELEASE OF MATERIALS

(71) Applicant: The Research Foundation for The State University of New York, Buffalo, NY (US)

(72) Inventors: Jonathan Lovell, Niagara Falls (CA); Dandan Luo, Amherst, NY (US); Kevin Carter, Amherst, NY (US); Shuai Shao, Tonawanda, NY (US); Jumin Geng, Williamsville, NY (US)

(73) Assignee: The Research Foundation for The State University of New York, Amherst, NY (US)

( * ) Notice: Subject to any disclaimer, the term of this patent is extended or adjusted under 35 U.S.C. 154(b) by 0 days.

(21) Appl. No.: 15/563,703

(22) PCT Filed: Apr. 4, 2016

(86) PCT No.: PCT/US2016/025882
§ 371 (c)(1),
(2) Date: Oct. 2, 2017

(87) PCT Pub. No.: WO2016/161428
PCT Pub. Date: Oct. 6, 2016

(65) Prior Publication Data
US 2018/0140552 A1 May 24, 2018

Related U.S. Application Data

(60) Provisional application No. 62/142,105, filed on Apr. 2, 2015.

(51) Int. Cl.
*A61K 9/127* (2006.01)
*A61K 31/704* (2006.01)
(Continued)

(52) U.S. Cl.
CPC .......... *A61K 9/1271* (2013.01); *A61K 9/0019* (2013.01); *A61K 9/127* (2013.01);
(Continued)

(58) Field of Classification Search
CPC .... A61K 9/127; A61K 9/1271; A61K 9/0019; A61K 47/6911; A61K 31/4745; A61K 31/704
See application file for complete search history.

(56) References Cited

U.S. PATENT DOCUMENTS 5,051,415 A * 9/1991 Morgan ................. A61K 31/40
424/1.53
5,707,608 A * 1/1998 Liu ........................ A61K 9/127
424/9.1
(Continued)

FOREIGN PATENT DOCUMENTS

WO 2011044671 A1 4/2011
WO 2014/100379 A1 6/2014

OTHER PUBLICATIONS

Luo et al., Doxorubicin encapsulated in stealh lipsomes conferred with light-triggered drug release, Biomaterials, vol. 75, pp. 123-202. Oct. 23, 2015.
(Continued)

*Primary Examiner* — Gollamudi S Kishore
(74) *Attorney, Agent, or Firm* — Hodgson Russ LLP

(57) ABSTRACT

Provided are serum-stable nanoparticles comprising porphyrin-phospholipid conjugates. Also provided are compositions comprising the nano-particles. The nanoparticles can comprise cargo such as therapeutic agents and/or diagnostic agents (e.g., imaging agents) and be used in drug delivery methods based on NIR stimulated cargo release.

22 Claims, 39 Drawing Sheets

(51) Int. Cl.
*A61K 9/00* (2006.01)
*A61K 47/69* (2017.01)
*A61K 31/4745* (2006.01)

(52) U.S. Cl.
CPC ........ *A61K 31/4745* (2013.01); *A61K 31/704* (2013.01); *A61K 47/6911* (2017.08)

(56) References Cited

U.S. PATENT DOCUMENTS

| | | | |
|---|---|---|---|
| 2004/0076559 A1* | 4/2004 | Brucker | A61L 2/08 422/186 |
| 2006/0039965 A1* | 2/2006 | Boch | A61K 9/1075 424/450 |
| 2006/0204447 A1* | 9/2006 | Knight | A61K 9/0073 424/45 |
| 2007/0231375 A1* | 10/2007 | Tsai | A61K 9/1271 424/450 |
| 2009/0030261 A1 | 1/2009 | Whitmore | |
| 2009/0196903 A1 | 8/2009 | Kliman | |
| 2013/0115273 A1* | 5/2013 | Yang | A61K 9/1272 424/450 |
| 2014/0271822 A1 | 9/2014 | McGhee et al. | |

OTHER PUBLICATIONS

Carter et al., "Porphyrin-phospholipid liposomes permeabilized by near-infrared light," Nat. Comm., Apr. 3, 2014, pp. 1-11, 5:3546.

\* cited by examiner

C

D

SERUM-STABLE COMPOSITIONS AND METHODS FOR LIGHT-TRIGGERED RELEASE OF MATERIALS

CROSS-REFERENCE TO RELATED APPLICATIONS

This application claims priority to U.S. Provisional patent application No. 62/142,105, filed Apr. 2, 2015, the disclosure of which is incorporated herein by reference.

STATEMENT REGARDING FEDERALLY SPONSORED RESEARCH

This invention was made with government support under contract no. EB017270 and OD017898 awarded by the National Institutes of Health. The government has certain rights in the invention.

FIELD OF THE DISCLOSURE

This disclosure relates generally to delivery compositions and more particularly to porphyrin phospholipid conjugate compositions.

BACKGROUND OF THE DISCLOSURE

Drug delivery to target tissues can be just as important as the drug being delivered. Several clinically approved nanocarriers have been developed to enhance the biodistribution and efficacy of certain drugs. However, such delivery is hampered by physiological barriers and release kinetics so that biodistribution and bioavailability are almost inevitably sub-optimal. Additionally, stability of the nanocarriers under physiological environment is also important. Presently, the most viable approaches for externally triggered cargo release from nanocarriers comprise systems that release their contents when the surrounding temperatures are raised by a few degrees above body temperature by direct or indirect heating. However, such mechanisms are not readily amenable to trigger-side release modulation and the narrow thermal operating window precludes high carrier stability at physiological temperatures and physiological environment.

SUMMARY OF THE DISCLOSURE

The present disclosure provides self-assembled nanoparticles comprising porphyrin-phospholipid (PoP) conjugates. Nanovesicles comprising the porphyrin-phospholipid conjugates, cholesterol, and other lipids of the present disclosure—also referred to herein as porphyrin-phospholipid liposomes ("PoP-liposomes")—are formulated to provide high efficiency of: 1) loading cargo, 2) serum-stable cargo retention in the absence of near infrared (NIR) irradiation (650-1000 nm) radiation, and 3) controlled release of cargo upon exposure to NIR irradiation.

In one aspect, this disclosure provides nanovesicles which comprise a bilayer, said bilayer comprising porphyrin-phospholipid conjugates. In one embodiment, the nanovesicles bilayers comprise porphyrin-phospholipid conjugate, phospholipid, cholesterol or analogs thereof. In one embodiment, the bilayer comprises porphyrin-phospholipid conjugate, phospholipid, cholesterol, and polyethylene glycol-lipid. In one embodiment, the disclosure provides compositions comprising the nanovesicles in a suitable medium such as a buffer or saline solution. In one embodiment, this disclosure provides nanovesicles wherein the bilayer of the nanovesicles comprises porphyrin-lipid, phospholipid, cholesterol or analogs thereof, and optionally, polyethylene glycol. The nanovesicles may be present in a buffer or saline solution and the nanovesicles may comprise a cargo (such as a therapeutic, targeting or diagnostic or any other agent).

In one aspect this disclosure provides methods for loading of the nanovesicles with desired cargo and methods for delivery of cargo in vitro or in vivo in a spatially and temporally controlled manner.

The following abbreviations are used in this disclosure:
DSPC: 1,2-distearoyl-sn-glycero-3-phosphocholine
Dox: Doxorubicin
IRT: irinotecan
PoP: Porphyrin-phospholipid conjugate (also referred to herein as porphyrin-phospholipid) Pyro-phosholipid conjugate (also referred to herein as pyro-phospholipid): A type of porphyrin-phospholipid conjugate that can be generated by an esterification reaction between lysophosphatidylcholine and pyropheophorbide.
PoP-liposomes: porphyrin-phospholipid (PoP)-doped liposomes (also referred to herein as nanovesicles)
PEG2K-lipid: PEG-lipid, 1,2-distearoyl-sn-glycero-3-phosphoethanolamine-N-[amino(polyethyleneglycol)-2000]
DMPC: 1,2-dimyristoyl-sn-glycero-3-phosphocholine
DOPC: 1,2-dioleoyl-sn-glycero-3-phosphocholine
DPPC: 1,2-dipalmitoyl-sn-glycero-3-phosphocholine
HSPC: L-α-phosphatidylcholine, hydrogenated (Soy)
DSPE: 1,2-distearoyl-sn-glycero-3-phosphoethanolamine
DPPA: 1,2-dihexadecanoyl-sn-glycero-3-phosphate (sodium salt)
DOTAP: 1,2-dioleoyl-3-trimethylammonium-propane (chloride salt)
DSPG: 1,2-distearoyl-sn-glycero-3-phospho-(1'-rac-glycerol) (sodium salt)

DESCRIPTION OF THE DISCLOSURE

Figure 1:
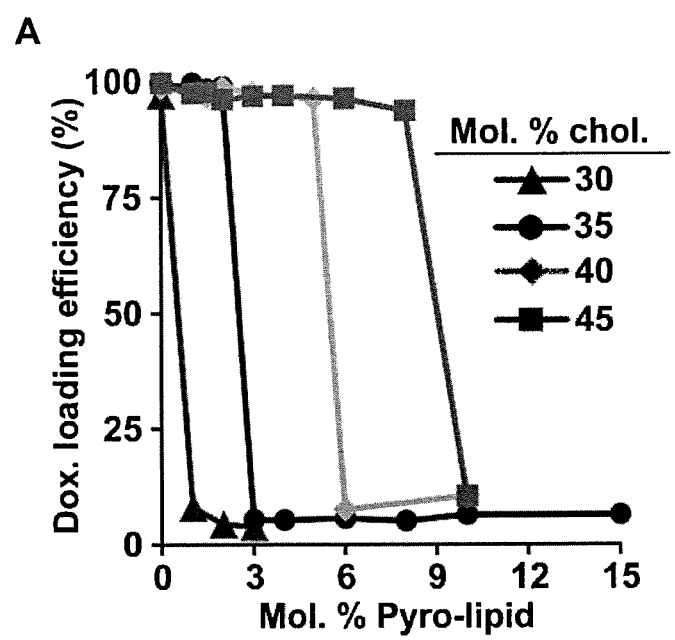
FIG. 1. Cholesterol enables Dox loading into PoP liposomes. A) Dox active loading efficiency in PoP liposomes with a Dox-to-lipid loading molar ratio of 1:8.5 mol % PEG-lipid was included together with the indicated amounts cholesterol and Pyro-phospholipid, and DSPC completed the formulation. B) Dox active loading efficiency in liposomes with or without 2 molar % pyro-phospholipid. The Dox-to-lipid loading molar ratio was 1:5. Values show mean+/−S.D. for n=3. C) Cryo-electron micrographs of Dox-PoP liposomes formed with a DSPC:CHOL:PEG-lipid:PoP molar ratio of 53:40:5:2 and a 1:5 Dox-to-lipid loading ratio. Images were collected with a defocus ranging between −7 to −8 microns defocus. Arrows point to Dox precipitates within the liposomes. 100 nm scale bar is shown. D) Loading efficiency of Pyro liposomes have a sharp decrease at the drug to lipid loading ratio of 0.2, while the loading efficiency of pyro free liposomes gradually decrease.
Figure 1:
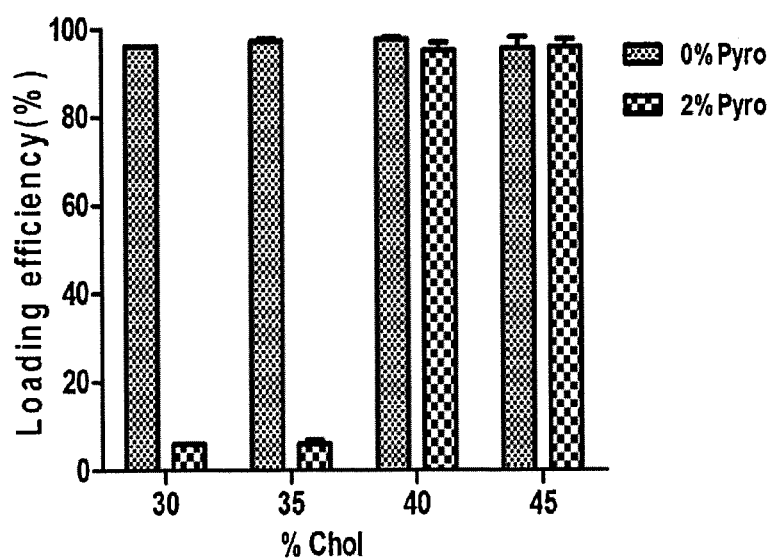
Figure 1:
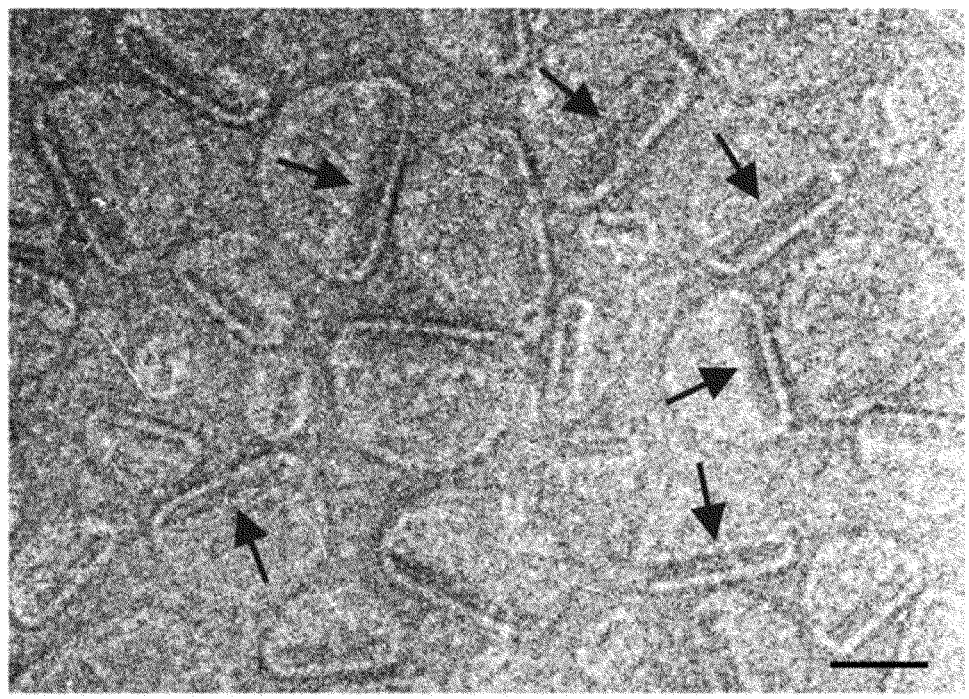
Figure 1:
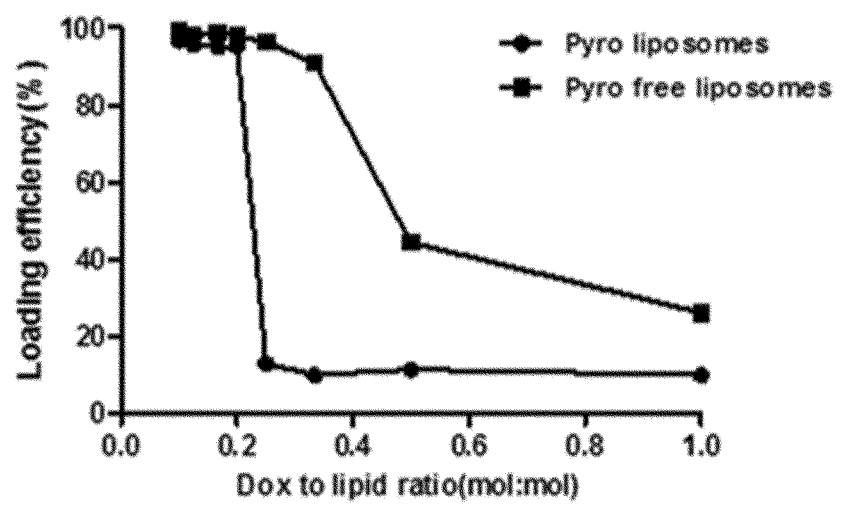

In this disclosure, provided are serum-stable, light-controlled-release porphyrin-phospholipid nanovesicles (PoP-liposomes), having high loading efficiency. Release of cargo from the PoP-liposomes can be triggered directly by near infrared (NIR) light, a clinically applicable stimulus that has negligible actuation in the "off state" and minimal interference with surrounding biological tissues.

The present disclosure is based on the surprising and unexpected observation that by including cholesterol in the formulation of the nanovesicles, the loading efficiency of these vesicles can be increased and the serum stability is improved. The nanovesicles of the present disclosure comprise porphyrin-lipid, phospholipids, cholesterol, and optionally PEG-lipid. The nanovesicles of the present disclosure exhibit stable loading, high loading efficiency, serum-stability, and controlled-release of cargo.

In specific embodiments, the bilayer of the PoP-liposomes of the present disclosure comprises, consists essentially of, or consist of porphyrin conjugate, phospholipid, cholesterol, and optionally PEG-lipid. In one embodiment, the bilayer of the present PoP liposomes comprises porphyrin conjugates and lipids, wherein the only lipids—whether conjugated to the porphyrin, or present as additional lipids are phospholipids, and sterols.

In one aspect, this disclosure provides a liposome formulation comprising porphyrin-phospholipid and cholesterol and other lipid components that is able to 1) rapidly release contents in response to exposure to near infrared (NIR) light; 2) actively load drugs into the liposomes; 3) be stable in serum (e.g., for 6 hours with less than 20% drug leakage) in the absence of laser exposure. A feature of the present formulations is that it minimizes the amount of PoP in the cargo-loaded PoP-liposomes (cargo-PoP-liposomes) while maintaining serum stability and fast releasing properties. This is advantageous because increased amounts of photosensitizing components carry potential side effects for patients (e.g. sunlight sensitivity).

In one aspect, the present disclosure provides nanovesicles and compositions comprising nanovesicles. The bilayer of the nanovesicles comprises porphyrin conjugates. The porphyrin conjugate making up some or all of the bilayer of the nanovesicles comprises porphyrins, porphyrin derivatives, porphyrin analogs, or combinations thereof. Exemplary porphyrins include hematoporphyrin, protoporphyrin, and tetraphenylporphyrin. Exemplary porphyrin derivatives include pyropheophorbides, bacteriochlorophylls, Chlorophyll A, benzoporphyrin derivatives, tetrahydroxyphenyl chlorins, purpurins, benzochlorins, naphthochlorins, verdins, rhodins, keto chlorins, azachlorins, bacteriochlorins, tolyporphyrins, and benzobacteriochlorins. Exemplary porphyrin analogs include expanded porphyrin family members (such as texaphyrins, sapphyrins and hexaphyrins) and porphyrin isomers (such as porphycenes, inverted porphyrins, phthalocyanines, and naphthalocyanines).

In certain embodiments, the porphyrin conjugate comprises a metal chelated therein, preferably a divalent metal such as Zn, Cu, Ni, Co, Pd or Mn, and optionally a radioisotope of a metal such as Cu-64.

As used herein, "phospholipid" is a lipid having a hydrophilic head group having a phosphate group connected via a glycerol backbone to a hydrophobic lipid tail. The phospholipid comprises an acyl side chain of 6 to 22 carbons, including all integer number of carbons and ranges therebetween. In certain embodiments, the phospholipid in the porphyrin conjugate is 1-palmitoyl-2-hydroxy-sn-glycero-3-phosphocholine. The phospholipid in the porphyrin conjugate may comprise, or consist essentially of phosphatidylcholine, phosphatidylethanoloamine, phosphatidylserine and/or phosphatidylinositol.

In certain embodiments, the bilayer of the self-assembled nanovesicle further comprises PEG-lipid. The PEG-lipid can be DSPE-PEG such as DSPE-PEG-2000, DSPE-PEG-5000 or other sizes of DSPE-PEG. The PEG-lipid is present in an amount of 0.5 to 8 mol % including all percentage amounts therebetween to the tenth decimal point. In one embodiment, the PEG-lipid is present from 4-6 mol %. In one embodiment, it is present about 5% (4.8 to 5.2 mol %). The average molecular weight of the PEG moiety can be between 500 and 5000 Daltons and all integer values and ranges therebetween. In one embodiment the molecular weight of the PEG moiety is 2000 Daltons.

In various embodiments, in addition to the porphyrin conjugates disclosed herein, the bilayer of the nanovesicles also comprises other polar lipids. The fatty acid chains of the phospholipids of the present compositions may contain a suitable number of carbon atoms to form bilayer. For example, the fatty acid chain may contain 12, 14, 16, 18, 20 or 22 carbon atoms. In different embodiments the bilayer may comprise phosphatidylcholine, phosphatidylethanoloamine, phosphatidylserine,phosphatidylinositol and/or cationic lipids. Examples of suitable lipids include, but are not limited to, DSPC, DPPC, DMPC, HSPC, DSPG, DPPA, DSPE, DOTAP, sphingomyelin and the like.

The bilayer of the present nanovesicles also comprises sterols. The sterols may be animal sterols or plant sterols. Examples of sterols include cholesterol, sitosterol, stigmasterol, and cholestanol. For example, cholesterol can be more than 30 mol %. In one embodiment, it is 35 to 50 mol % and all integers therebetween. In one embodiment cholesterol is about 45% (43-47 mol %). In one embodiment, it is 40, 41, 42, 43, 44, or 45 mol %. The use of the PoP-liposome monomer of the present disclosure enabled effective loading of cargo into nanovesicles and use of mild NIR resulted in rapid and up to 100% release of cargo.

The present disclosure provides compositions comprising a porphyrin-phospholipid conjugate having the following structure:

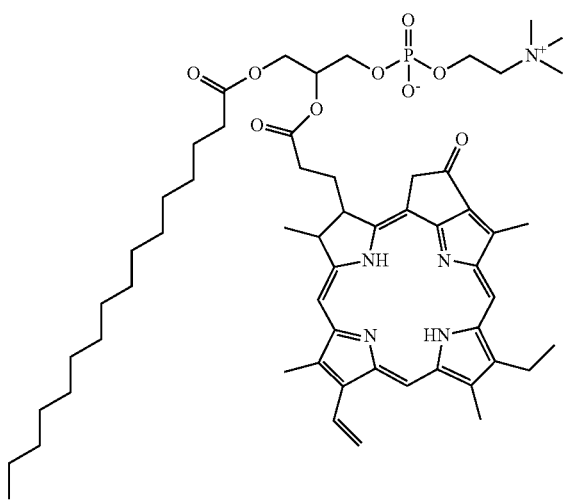 [SMILES: C=CC1=C(C)c2cc3[nH]c(c4c5nc(cc6[nH]c(cc1n2)c(C)c6CC)C(C)=C5C(=O)C4)C(CCC(=O)OC(COC(=O)CCCCCCCCCCCCCCC)COP(=O)([O-])OCC[N+](C)(C)C)C3C]

Pyro-phospholipid (Structure I)

In one embodiment, the mole % of the porphyrin-phospholipid conjugate compounds of nanovesicles of the present disclosure is from 0.1 to 5. In one embodiment, the PoP-liposome bilayer is made up of from 0.5 to 8 mol %. In one embodiment, the PoP-liposome bilayer comprises 1, 2, 3, 4, 5, 6, 7, or 8 mol %. In one embodiment, the PoP-liposomes comprise all mol percents to the tenth decimal place between 0.1 to 8.0.

In one embodiment, the present compositions comprise nanovesicles, wherein the nanovesicle comprises a bilayer, where the bilayer comprises 45 to 61.5 mol % phospholipid, 0.5 to 8% porphyrin conjugate, 35 to 45% sterol, and optionally, 1 to 6 mol % PEG-lipid. In one embodiment, the porphyrin conjugate, sterol, and optionally, PEG-lipid PEG are added in the desired amounts and then the remainder is made up with phospholipid. In one embodiment, the bilayer comprises 0.5 to 8% pyro-phospholipid, 35 to 45% cholesterol, and optionally, 1 to 6 mol % PEG-lipid, and the remaining is made up with a phospholipid (such as DSPC).

The nanovesicles of the present disclosure can have 0.1 to 5 mol % pyro-phospholipid, 30 to 50% sterol, optionally, PEG-lipid, and remaining phospholipid (which is not pyro-phospholipid). For example, the nanovesicles can have 0.1, 0.2, 0.3, 0.4, 0.5, 0.6, 0.7, 0.8, 0.9, 1.0, 1.5, 2.0, 2.5, 3.0, 3.5, 4.0, 4.5 or 5.0 mol % pyro-phospholipid, 30-50 mol % cholesterol, optionally, 1-6 mol % PEG-lipid and remaining phospholipid. The phospholipids may be any phospholipids. For example, the phospholipids can be DSPC. The phospholipids can be DOPC and DSPC. In an example, DSPC and DOPC are present and DOPC is present from 1 to 10 mol %. For example, the nanovesicles can have 0.1 to 5 mol % pyro-phopholipid, 30 to 50% cholesterol, optionally 1-6 mol % PEG-lipid, 0.1 to 10 mol % DOPC and remaining DSPC. A portion of DSPC may be replaced by other phospholipids (e.g., saturated, unsaturated, or partially unsaturated phospholipids) or lipids (e.g., sphingomyelin). The formulations were found to exhibit desirable release of cargo (e.g., 90% or greater release after 2 minute irradiation with a 350 mW/cm² laser) when irradiated with NIR light. To achieve improved serum stability at physiological temperatures, DOPC can be less than 7 mol %. For example, DOPC can be from 0.1 to 6.5 mol %, such as from 0.1 to 6.0 mol %, or 0.1 to 5 mol %.

The phospholipids (i.e., free phospholipids that are not conjugated to a porphyrin) can have two saturated alkyl chains (e.g., saturated phospholipids such as, for example, DSPC) or two unsaturated alkyl chains (e.g., unsaturated phospholipids such as, for example, DOPC and DLPC) or one saturated alkyl chain and one unsaturated alkyl chain (e.g., partially unsaturated phospholipids). The unsaturated phospholipids can have at least one or all cis carbon-carbon double bonds. The phospholipids can be a mixture of saturated phospholipid(s), unsaturated phospholipid(s), and/or partially unsaturated phospholipid(s). The unsaturated phospholipid can be from 0.1 mol % to 10 mol % of the nanovesicle. For example, the unsaturated phospholipid can be from 0.1 mol % to 6.5 mol % of the nanovesicle. In one example, the nanovesicles comprise an unsaturated phospholipid that is x mol %, a saturated phospholipid that is y-x mol % (wherein y=45 to 61 mol %, such as, for example, 59 to 60 mol % and all values to the tenth decimal place therebetween), sterol is 30 to 50 mol %, and porphyrin conjugate is from 0.1 to 5 mol % (such as, for example, 0.1 to 1.0 mol %). In one example, the nanovesicles comprise DOPC is x mol %, DSPC is y-x mol % (wherein y=45 to 61 mol %, such as, for example, 45 to 60, 59 to 61 or 59 to 60 mol % and all values to the tenth decimal place therebetween), cholesterol is 30 to 50 mol %, and pyro-phospholipid is from 0.1 to 5 mol % (such as, for example, 0.1 to 1.0 mol %). For example, the nanovesicles can comprise, consist essentially of, or consist of, 0.1 to 1.0 mol % pyro-phospholipid, 35 to 45 mol % cholesterol, 0.1 to 5 mol % DOPC and the remaining is DSPC.

The nanovesicles are substantially spherical prior to cargo (e.g., drug) loading. The nanovesicles can be non-spherical after cargo (e.g., drug) loading. The nanovesicles (loaded or unloaded) can have a size (e.g., a longest dimension) of from 50 nm to 250 nm in diameter and all integer to the nm and ranges therebetween. In one embodiment, the size of the nanovesicles is from 75-175 nm. In one embodiment, at least 50%, 60%, 70%, 80%, 85%, 90%, 95%, 99%, or 100% of the nanovesicles in the composition have a size of from 50 to 250 nm, from 75 to 175 nm, or from 80-100 nm. In one embodiment, these sizes are observed in PBS.

A composition can comprise one or more nanovesicles in carrier. For example, a composition further comprises a carrier. The carrier can be an aqueous carrier suitable for administration to individuals including humans. The carrier can be sterile. The carrier can be a physiological buffer. Examples of suitable carriers include sucrose, dextrose, saline, and/or a pH buffering element (such as, a buffering element that buffers to, for example, a pH from pH 5 to 9, from pH 6 to 8, (e.g., 6.5)) such as histidine, citrate, or phosphate.

In one aspect, the disclosure provides a composition comprising nanovesicles of the present disclosure and a sterile, suitable carrier for administration to individuals including humans—such as a physiological buffer such as sucrose, dextrose, saline, pH buffering (such as from pH 5 to 9, from pH 7 to 8, from pH 7.2 to 7.6, (e.g., 7.4)) element such as histidine, citrate, or phosphate. In one embodiment, the composition comprises at least 0.1% (w/v) PoP-liposomes of the present disclosure. In various embodiments, the composition comprises from 0.1 to 100% PoP-liposomes. Apart of the agent molecule (cargo) may be embedded in the bilayer.

In one aspect, the present PoP liposomes may be provided in serum-based media or carriers. Thus, for example, the PoP liposomes may be present in diluted, concentrated or undiluted serum.

The PoP liposomal formulations can be incubated in buffers, including physiological buffers, or serum-containing media for periods of 4 to 24 hours at physiological temperatures (e.g., 37° C.) without releasing the majority of their cargo. In various examples, the PoP liposomal formulations can be incubated in physiological buffers or serum-containing media for periods of 4 to 24 hours at physiological temperatures (e.g., 37° C.) without releasing 60% or more, 70% or more, 80% or more, or 90% or more of their cargo.

The nanovesicles are stable in diluted (e.g., 50% by weight serum and 50% by weight aqueous buffer) or undiluted serum. In various example, the nanovesicles release 20% or less, 15% or less, or 10% or less of their cargo after storage at physiological temperatures (e.g., 37° C.) for 6 hours to 24 hours.

A wide variety of cargo may be loaded into the nanovesicles of the present disclosure and delivered to desired locations using near infrared light. For example, bioactive or therapeutic agents, diagnostics agents, targeting agents, pharmaceutical substances, and/or drugs can be encapsulated within the interior of the PoP-liposome. This includes water soluble drugs and also drugs that are weak acids or bases that can be loaded via chemical gradients and concentrated in the aqueous core of the nanovesicle. Thus, in various embodiments, the nanovesicle comprises an active agent encapsulated therein, such as a therapeutic agent or a diagnostic agent, which can be a chemotherapy agent such as doxorubicin. In one embodiment, the chemotherapeutic agent doxorubicin and/or irinotecan can be actively loaded and released with NIR irradiation providing for robust and direct light-triggered release using PoP nanovesicles.

Cargo can be passively loaded and can be, including but not limited to, hydrophilic imaging and therapeutic compounds such as gadolinium chelates, such as Gd-DTPA, fluorescence imaging dyes such as ICG, SRB, or fluorescein, and passively loaded drugs such as cisplatin, oxaliplatin, carboplatin, methotrexate, prednisolone phosphate, gentamicin, or therapeutic proteins and therapeutic nucleic acids. Cargo can be actively loaded cargo such as weak amphiphatic drugs, with weak basic or acidic moieties that form precipitates inside the liposomes and include but is not limited to bupivacaine, epirubicin, daunorubicin, vinblastine, hydromorphone, vincristine, mitomycin C, dopamine, serotonin, epinephrine, codeine, meperidine, methadone, morphine, atropine, imipramine, amitriptyline, doxepin, desipramine, quinidine, acridine orange.

In one embodiment, the ratio of lipid to drug (or any other cargo agent) (on a mol basis) is from 10:1 to 5:1. In various embodiments, the ratio of lipid to drug/cargo ratio is 10:1, 9:1, 8:1, 7:1, 6:1, or 5:1. In one embodiment, the lipid value used for these determinations takes into consideration all the lipid—including lipid conjugated to porphyrin, additional phospholipid, sterol, and lipid conjugated to PEG (if present).

The term "therapeutic agent" refers to any chemical moiety that is a biologically, physiologically, or pharmacologically active substance. Examples of therapeutic agents, also referred to as "drugs", are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Drugs that are known to be loaded via active gradients include doxorubicin, irinotecan, gemcitabine, epirubicin, topotecan, vincristine, mitoxantrone, ciprofloxacin, cisplatin and daunorubicin. These drugs can be loaded in and released from PoP-liposomes. Therapeutic cargo also includes various antibiotics (such as gentamicin) or other agents effective against infections caused by bacteria, fungi, parasites, or other organisms, anti-inflammatory agents, or antiviral agents.

A "diagnostic" or "diagnostic agent" is any chemical moiety that may be used for diagnosis. For example, diagnostic agents include imaging agents, such as those containing radioisotopes such as indium or technetium; contrast agents containing iodine or gadolinium chelates.

In certain embodiments, the nanovesicle further comprises a targeting molecule, such as an antibody, peptide, aptamer or folic acid. "Targeting molecule" is any molecule that can direct the nanovesicle to a particular target, for example, by binding to a receptor or other molecule on the surface of a targeted cell. Targeting molecules may be proteins, peptides, nucleic acid molecules, saccharides or polysaccharides, receptor ligands or other small molecules. The degree of specificity can be modulated through the selection of the targeting molecule. For example, antibodies typically exhibit high specificity. These can be polyclonal, monoclonal, fragments, recombinant, or single chain, many of which are commercially available or readily obtained using standard techniques.

In one aspect, the disclosure provides a method of preparing a nanovesicle comprising mixing a porphyrin-phospholipid conjugate in buffer, wherein the porphyrin-phospholipid conjugates are as described herein, and extruding the mixture to yield a porphyrin-phospholipid bilayer nanovesicle comprising a bilayer of the desired amount of the porphyrin-phospholipid conjugate. In addition to the porphyrin-phospholipid (such as 2 mol %), other phospholipids or lipids may be included in the mixture to make the PoP-liposomes. For example, in one embodiment, DSPE-PEG-2K (e.g. 5 mol %); cholesterol (e.g., 40 mol %) and lipid (e.g. DSPC 53 mol %) may be used. Porphyrin-phospholipid conjugate may be prepared by esterifying a carboxylic acid-bearing tetrapyrrole to a lyso-phospholipid. For example, Pyro-phospholipid can be esterified at room temperature with 1-palmitoyl-2-hydroxy-sn-glycero-3-phosphocholine (lyso-C16-PC), Avanti #855675P) using EDC and 4-dimethylaminopyridine (DMAP, Fisher #AC14827-0250) in chloroform at a 1:1:2:2 lyso-C16-PC:Pyro:EDC:DMAP molar ratio.

In one embodiment, PoP-liposomes are formed by the dispersion of porphyrin-lipid, cholesterol and other lipid and optionally, PEG-lipid components. For example, in one embodiment, Pyro-phospholipid liposomes can be prepared by dissolving DSPC, DSPE-PEG2K, Pyro-phospholipid and cholesterol in a solvent and heated (such as to 60 to 70° C.). Buffered ammonium sulfate or sodium citrate can then be added to the reaction mixture while maintaining the temperature. Upon liposome formation, the liposomes can be extruded under high pressure (such as with sequentially stacked polycarbonate membranes) to achieve the desired liposome size. Residual starting materials, such as ammonium sulfate or sodium citrate, can be removed (such as by dialysis). Cargo loading into the nanovesicle can be carried out by addition of the desired ratio of cargo followed by incubation. Liposome sizes and zeta potential, if desired, can be determined by light scattering techniques. Loading efficiency can be determined by running a solution of liposomes over a column, and quantifying the percentage of drugs in the liposome containing fractions. The drug quantities can be measured using fluorescence spectroscopy. Light-triggered release can be achieved by using a laser diode. If desired, cargo release can be assessed by measuring the release before and after exposure to laser.

In one aspect, the disclosure provides a method of delivery of agents contained as cargo in the nanovesicles to desired locations. Although at times, cargo is described as drug in the disclosure, the description is equally applicable to any agent contained for treatment and/or delivery to a desired location, and the term "drug" is intended to refer to any agent. The agent may be contained, in whole or in part, within or in the PoP-liposomes—whether present in the aqueous compartment, the bilayer or both. Thus, in another aspect, the disclosure provides a method for delivery of cargo of a nanovesicle comprising the steps of: 1) providing a composition comprising nanovesicles of the present disclosure comprising the cargo (such as an active agent); 2) allowing the nanovesicles to reach a selected or desired destination; 3) irradiating the nanovesicle with radiation having a wavelength of near-infrared under conditions such that at least a portion of the cargo is released from the nanovesicle.

The method of the present disclosure can be carried out in vitro or in vivo. When carried out in vivo, in one embodiment, the irradiation with near-infrared radiation is such that the temperature of the surrounding tissue does not increase more than 10 degrees Celsius. In various embodiments, the temperature of the surrounding tissue does not increase more than 5, 6, 7, 8, 9 and 10, 11 and 12 degree Celsius. In other embodiments, the temperature of surrounding tissue increases by less than 5 degrees Celsius. The method of the present disclosure can be used in any individual of any age including animals and humans.

The nanovesicles are irradiated with near-infrared light from a laser of power 5 to 1000 mW/cm$^2$, including all integer values to the mW/cm$^2$ and ranges therebetween, at a wavelength of from 650 to 1000 nm, including all integer values to the nm and ranges therebetween. In one example, the power is from 10 to 350 mW/cm$^{2'}$ For example, the power of the laser can be from 250 to 350 mW/cm$^2$ and the wavelength of the laser can be from 650 to 800 nm, or 655-675, or 660 to 670 nm including all integer values to the nm and all ranges therebetween.

The release of cargo is dependent upon laser power. In one embodiment, the present formulations in physiological buffers or serum-based medium at physiological temperatures (around 37° C.) exhibit no detectable release of cargo in the absence of a light trigger. However, when light in the 660-670 nm wavelength from a 300 mW/cm$^2$ laser is shined on the nanovesicles, immediate release of the cargo is observed. At least 90%, 91, 92, 93, 94, 95, 96, 97, 98, 99 or 100% of the cargo can be released from PoP liposomes in a serum-based medium at 37° C. within 5 minutes of exposure to a laser of 300 mW/cm$^2$ having a wavelength of about 665 nm. Such release can be observed within 1, 2, 3, or 4 minutes. If a laser with higher power is used, the release of the cargo can be achieved faster. However, 300 mW/cm$^2$ can be considered to be clinically acceptable.

The extent of release of cargo is also dependent upon the exposure time. Generally, a time of up to 30 minutes or less is sufficient. The nanovesicles in vitro or in vivo may be irradiated from 0.5 to 30 minutes and all values to the tenth decimal place therebetween. For example, the nanovesicles can be irradiated with a 665 nm laser diode for up to 10 minutes. By varying the laser power and/or the laser time, control over how much drug is released from the nanovesicles is achieved. Further, controlled irradiation to achieve a "small-vessel-only" light-release strategy that can result in lower systemic drug release and will not harm critical vessels in organs with extensive vasculature (such as the pancreas). The infrared radiation can be delivered to the desired area directly by shining laser light on the area or fiber optic probes may be used. In the case of a tumor, the fiber optic probe can be inserted into the tumor (i.e., via a catheter or endoscopic device) to provide irradiation to a localized area. Following laser exposure, the nanovesicles may be resealed. In this manner, the opening and closing of the nanovesicles may be reversible.

The methods can use nanovesicles loaded with both imaging and therapeutic agents into the liposome. These liposomes can be administered to an individual (e.g., injected into a tumor) and imaging agents used to verify location of the nanvesicles and/or tumor distribution, and the nanovesicles irradiated triggering release of the agents.

The methods can selectively/sequentially deliver two or more cargos by irradiating two or more types of nanovesicles having at least one different porphyrin conjugate. An example of selective/sequential delivery is described in Example 4. For example, if the individual porphyrin conjugates in the administered nanovesicles have an absorption maximum that allow triggered release from one type of nanovesicles without detectible triggered release from other nanovesicles. For example, at least two different nanovesicles with at least one different porphyrin conjugate that have absorption maxima separated by 10 nm or more can selectively/sequentially delivered by irradiating the nanovesicles with light of a wavelength that triggers release from one or more types of nanovesicles without triggering release of more than 20% of the cargo from at least one other type of nanoparticles. In various examples, at least two nanovesicles with at least one different porphyrin conjugate that have absorption maxima separated by 15, 20, 25, or 50 nm or more can selectively/sequentially delivered by irradiating the nanovesicles with light of a wavelength that triggers release from one or more types of nanovesicles without triggering release of more than 10, 5, 4, 3, 2, 1, or 0.5% of the cargo from at least one other type of nanoparticles. In an example, at least two nanovesicles with at least one different porphyrin conjugate that have absorption maxima separated by 10, 15, 20, 25, or 50 nm or more can selectively/sequentially delivered by irradiating the nanovesicles with light of a wavelength that triggers release from one or more types of nanovesicles without triggering release of any detectible cargo from at least one other type of nanoparticles. The release of cargo can be detected by methods known in the art and by methods disclosed herein.

A useful property of the nanovesicles of the present disclosure is there is minimal release (i.e., less than 5% release of contents per hour) of the active agent when incubated in serum-containing media at 37° C. until near-infrared light is shined at the nanovesicle. In one embodiment, 100% of the active agent (cargo) that is irradiated in the target tissue with sufficient laser power is released from the nanovesicle. When the active agent is released in vivo from the nanovesicle, the temperature of the surrounding tissue does not increase significantly. By selecting the intensity of the NIR applied, the amount of cargo released at a given location or given time can be controlled. Thus, anywhere between 1 to 100% (and all integers therebetween) of the cargo from nanovesicles can be released at desired locations and times. In one embodiment, the release of cargo (anywhere from 1 to 100% of the cargo) is achieved in one or more steps. For example, pulses of NIR exposure may be used at desired time intervals so that the cargo is released in steps.

The composition comprising the nanovesicles in a suitable carrier can be administered to individuals by any suitable route. In one embodiment, it is administered by intravenous infusion such that it will enter the vasculature (circulatory system). The composition may be administered systemically or may be administered directly into the blood supply for a particular organ or tissue or tumor. When irradiated by NIR, the contents of the PoP-liposomes may be released within the circulatory system and may then enter the surrounding tissue. In certain embodiments, the PoP-liposomes may be directly provided to the relevant tissue.

Additionally, the serum stability of the PoP-liposomes enables longer time point options for triggered release (less stable delivery systems must be triggered immediately following administration).

In one embodiment, the present disclosure provides a nanovesicle comprising a bilayer of at least 0.5 mol % to 8 mol % of a porphyrin-phospholipid conjugate and all percentages to the tenth decimal place therebetween. In specific embodiments, the nanovesicles comprise from 1 to 8 mol %, from, 0.5 to 5.0 mol %, from 0.5 to 3 mole %, from 1 to 3 mol %, about 2 mol % (1.5 to 2.5 mol %), and 2 mol % porphyrin-phospholipid conjugate, wherein the porphyrin-phospholipid conjugate can be the structure of Pyro-phospholipid. In one embodiment, the present disclosure provides compositions comprising the nanovesicles in a suitable carrier. In another embodiment, the present disclosure provides a method of delivering an agent to a desired site comprising the steps of: loading the agent as a cargo in the PoP-liposomes of the present disclosure, administering the PoP-liposomes to an individual, causing the release of the cargo (agent) at desired sites by shining near infra-red radiation as the nanovesicles are passing through the vasculature at the desired site such that the cargo from the nanovesicles is released. In one embodiment, upon shining the NIR radiation, the cargo (agent) release may be achieved when the nanovesicles are moving through small blood vessels (such as capillaries). In this manner, drug release may be confined only to smaller vessels in the target tissues and not nearby larger blood vessels.

In the following Statements, various examples of the compositions and methods of the present disclosure are described:

1. In an example, a composition comprises nanovesicles (e.g., nanovesicles having a bilayer), wherein the bilayer of the nanovesicles comprises 0.1 to 5 mol % porphyrin-phospholipid, 30 to 50% sterol, 45 to 61.5 mol % phospholipid which is not conjugated to porphyrin, and optionally 1 to 6% polyethylene glycol-lipid.

2. In another example, a composition is the composition of Statement 1, where the porphyrin-phospholipid has the following structure (pyro-phospholipid):

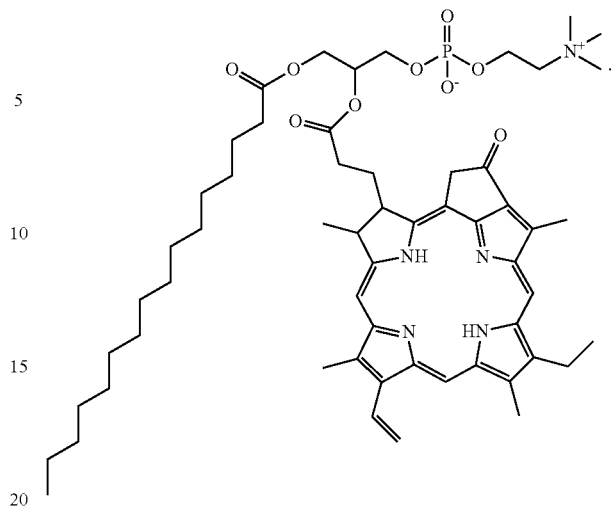

3. In another example, a composition is the composition of Statement 1 or 2, where the sterol is cholesterol.
4. In another example, a composition is the composition of any one of the preceding Statements, where the phospholipid comprises DSPC and DOPC.
5. In another example, a composition is the composition of any one of the preceding Statements, where the bilayer comprises 0.1 to 1.0 mol % porphyrin-phospholipid, 35 to 45% cholesterol, with the remainder being made up by phospholipids.
6. In another example, a composition is the composition of any one of the preceding Statements, where the nanovesicles composition is selected from the group consisting of:
  i) DSPC:PEG-lipid:cholesterol:PoP (e.g., pyro-phospholipid conjugate)::53:5:40:2;
  ii) DSPC:DOPC:Cholesterol:PoP (e.g., pyro-phospholipid conjugate)::54.7:5:40:0.3;
  iii) Cholesterol:DSPC:DOPC:PEG-lipid:PoP (e.g., pyro-phospholipid conjugate)::50:32:11:5:2; and
  iv) DSPC:PEG-lipid:Cholesterol:PoP (e.g., pyro-phospholipid conjugate)::60:%:35:2.
7. In another example, a composition is the composition of any one of the preceding Statements, where the nanovesicles are present in a carrier (e.g., a physiological buffer or a serum-containing solution).
8. In another example, a composition is the composition of any one of the preceding Statements, where the phospholipid comprises DSPC and DOPC, wherein the DOPC is present from 0.1 to 5 mol %.
9. In another example, a composition is the composition of any one of the preceding Statements, where the nanovesicles comprise 0.1 to 5 mol % pyro-phospholipid, 35 to 45 mol % cholesterol, DSPC and DOPC, wherein DSPC and DOPC together is 59 to 61 mol %, and wherein DOPC is from 0.1 to 5 mol %.
10. In another example, a composition is the composition of any one of the preceding Statements, wherein cargo molecules (e.g., a single type of cargo, a mixture of a single type of cargo, or a mixture of two or more different types of cargo) are present in the nanovesicles.
11. In another example, a composition is the composition of any one of the preceding Statements, where the cargo is Doxorubicin, Irinotecan, Daunorubicin, or a combination thereof.
12. In another example, a composition is the composition of any one of the preceding Statements, where the nanovesicles comprise a therapeutic agent and an imaging agent and the agents are separate and distinct molecules.

13. In another example, a composition is the composition of any one of the preceding Statements, where the cargo is present in the internal aqueous compartment of the nanovesicles.

14. In another example, a composition is the composition of any one of the preceding Statements, wherein the phospholipid to cargo drug ratio is from 10:1 to 5:1.

15. In another example, a composition is the composition of any one of the preceding Statements, wherein the nanovesicles are at least of two types, wherein each type of nanovesicle has a different porphyrin-lipid, and each different porphyrin-lipid has a different absorption maximum.

16. In another example, a composition is the composition of any one of the preceding Statements, wherein the nanovesicles are of two types, wherein the porphyrin-phsopholipid in one type is pyro-phospholipid and the porphyrin-phospholipid in the second type is purpurin-phospholipid.

17. In an example, a method of delivering a cargo to a desired location comprises the steps of: a) administering to an individual the composition of any one of the preceding Statements such that it enters the circulatory system; b) allowing the nanovesicles to reach the desired location; and c) exposing the nanovesicles to near infrared radiation of wavelength from 650 to 1000 nm such that the cargo is released from the nanovesicles.

18. In another example, a method is the method of Statement 17, where the nanovesicles comprise an imaging agent and the method further comprises imaging the individual after administration and before exposing the nanovesicles and determining that the nanovesicles have reached the desired location.

19. In another example, a method is the method of any one of Statements 17 or 18, where the individual is a human or non-human mammal.

20. In another example, a method is the method of any one of Statements 17 to 19, where the nanovesicles are exposed to a wavelength of 658, 665, 671, or 695 nm.

21. In another example, a method is the method of any one of Statements 17 to 20, where the nanovesicles are exposed to near infrared radiation for up to 30 minutes.

22. In another example, a method is the method of any one of Statements 17 to 21, where c) is carried out as multiple exposures to the near infrared radiation.

23. In an example, a method of controlled release of cargo comprises: a) providing a composition comprising nanovesicles in a carrier, wherein the bilayer of the nanovesicles comprises 0.1 to 5 mol % porphyrin phospholipid, 30 to 50% sterol, 45 to 61.5 mol % phospholipid which is not conjugated to porphyrin, and optionally 1 to 6% polyethylene glycol-lipid, wherein there is no detectable release of the cargo at temperatures from room temperature to 37° C. (e.g., in a physiological buffer or serum-based medium); b) exposing the composition to a light of wavelength of 650-1000 nm (e.g., 650-675 nm) from a laser which has a power of from 10 to 350 mW/cm$^2$, where at least 90% of the cargo is released within 1 to 8 minutes upon exposure to light in b).

24. In another example, a method is the method of Statement 23, where the phospholipid not conjugated to porphyrin is DSPC and DOPC, and wherein DOPC is present from 0.1 to 5 mol %.

25. In another example, a method is the method of Statement 23, wherein the pyro-phospholipid is present from 0.1 to 1.0 mol %, and wherein at least 50% of the cargo is released within 1 minute.

26. In an example, a method of sequential release of multiple cargo comprises: a) administering to an individual at least a first type and a second type of nanovesicles, wherein the bilayer of the first and second nanovesicles each individually comprises 0.1 to 5 mol % porphyrin phospholipid, 30-50% sterol, 45 to 61.5 mol % phospholipid which is not conjugated to porphyrin, and optionally 1 to 6% polyethylene glycol-lipid, where the first type and second type of the nanovesicles have a different porphyrin phospholipid with different absorption maxima; and b) sequentially exposing the composition to at least two different wavelengths of light, wherein the first wavelength corresponds to the absorption maximum for the porphyrin-phospholipid of the first type of nanovesicle and the second wavelength corresponds to the absorption maximum for the second type of nanovesicle; thereby providing sequential release of the cargo in the first and the second types of nanovesicles.

27. In another example, a method is the method of Statement 26, where the at least two types of nanovesicles are present in the same composition.

28. In another example, a method is the method of any one of Statements 26 or 27, where the individual is a human or non-human mammal.

29. In another example, a method is the method of any one of Statements 26 to 28, where the nanovesicles are exposed to a wavelength of 658, 665, 671, 695 nm, or a combination thereof.

30. In another example, a method is the method of any one of Statements 26 to 29, where the nanovesicles are sequentially exposed to near infrared radiation for up to 30 minutes for each individual exposure.

The following examples are presented to illustrate the present disclosure. They are not intended to limiting in any manner.

EXAMPLE 1

This example describes the preparation of PoP-liposomes, and loading and release of cargo.

Materials and Methods. Preparation of PoP liposomes. Unless otherwise noted, lipids were obtained from Avanti and other materials were obtained from Sigma. HPPH-lipid and Pyro-phospholipid were synthesized as previously reported. Various liposome formulations were all made using the same method. The finalized stealth PoP liposome formulation included 53 mol % 1,2-distearoyl-sn-glycero-3-phosphocholine (DSPC, Avanti #850365P), 40 mol % cholesterol (Avanti #700000P), 2 mol % Pyro-phospholipid and 5 mol % 1,2-distearoyl-sn-glycero-3-phosphoethanolamine-N-[methoxy(polyethylene glycol)-2000 (DSPE-PEG-2K, Avanti #880120P). To generate 100 mg of PoP liposomes (a 5 mL batch), 57.1 mg DSPC, 19.1 mg DSPE-PEG-2K, 2.76 mg Pyro-phospholipid and 21.1 mg cholesterol were fully dissolved in 1 mL ethanol at 60-70° C., then 4 mL 250 mM ammonium sulfate (pH 5.5) buffer was injected into the mixed lipids (both mixed lipids and ammonium sulfate buffer were kept at 60-70° C. while injection). Lipids and buffer were fully mixed. The solution was passed 10 times at 60-70° C. through sequentially stacked polycarbonate membranes of 0.2, 0.1 and 0.08 μm pore size using a high pressure nitrogen extruder (Northern Lipids). Free ammonium sulfate was removed by dialysis in a 800 mL solution of 10% sucrose with 10 mM histidine (pH 6.5) with at least 2 times buffer exchanges.

Cargo loading and release of PoP liposomes. Doxorubicin (Dox; LC Labs #D-4000) was loaded by adding the indicated ratio of drug and incubating at 60° C. for 1 hour.

Liposome sizes were determined by dynamic light scattering in PBS. Loading efficiency was determined by running 25 µL of liposomes diluted in 1 mL PBS over a Sephadex G-75 column. 24×1 mL fractions were collected and the loading efficiency was determined as the percentage of the drugs in the liposome-containing fractions (which elute in the in the first 3-10 mL). Dox was measured using fluorescence with an excitation of 480 nm and emission of 590 nm using a TECAN Safire fluorescent microplate reader. Light-triggered release experiments were performed using a power-tunable 665 nm laser diode (RPMC laser, LDX-3115-665) at a fluence rate of ~310 mW/cm$^2$ and Dox release was measured in real time in a fluorometer (PTI). Irradiations were performed in 50% sterile mature bovine serum (Pel-Freez #37218-5) at 37° C. Temperature was measured by inserting a K-type thermocouple probe directly into the irradiated solution. Dox release was assessed by measuring the release before and after treatment. Release was calculated using the formula Release=$(F_{final}-F_{initial})/(F_{X-100}-F_{initial})*100\%$.

Cryo-electron microscopy. For cryo-EM, holey carbon grids (c-flat CF-2/2-2C-T) were prepared with an additional layer of continuous thin carbon (5-10 nm) and treated with glow discharge at 5 mA for 15 sec. Then, 3.4 µL of liposome loaded with doxorubicin in buffer containing 10% sucrose solution and 10 mM histidine (pH 6.5) were applied to the grids for 30 sec. To perform the specimen vitrification, grids were blotted and plunged in liquid ethane at ~−180° C. using a Vitrobot (FEI) with the blotting chamber maintained at 25° C. and 100% relative humidity. Liposomes were imaged in a JEOL2010F transmission electron microscope at 200 kV using a Gatan 914 cryo-holder. Images were collected at ×50,000 magnification and using a total dose of ~20 electrons per Å2 and a defocus range between −7 to −11 microns. Images were recorded in SO-163 films. Micrographs were digitized in a Nikon Super Coolscan 9000 scanner.

Liposome storage stability. Dox loaded stealth PoP Liposomes (drug to lipid molar ratio 1:5) were stored at 4° C. in closed amber vials without any other precautions and liposomes were periodically removed for routine analysis. Loading stability, size, polydisperity, serum stability and light triggered release rates were assessed every two weeks for 3 months with 3 separately prepared batches of liposomes. Liposomes sizes were determined in phosphate buffered saline (PBS) by dynamic light scattering. For serum stability measurements, liposomes were diluted 200 times (to 13.5 µg/mL Dox) in PBS containing 50% mature bovine serum (Pel-Freez #37218-5). Initial readings were taken and samples were incubated at 37° C. for 6 hours. 0.5% X-100 was added to lyse the liposomes and final fluorescence value were read. Dox release was calculated according to the formula % Release=$(F_{final}-F_{initial})/(F_{X-100}-F_{initial})\times100\%$. Loading stability and light triggered release rates were determined as described above.

Pharmacokinetics. All procedures in this work performed on mice were approved by the University at Buffalo Institutional Animal Care and Use Committee. Female mice (female CD-1, 18-20 g, Charles River) were intravenously injected via tail vein with Dox-PoP-liposomes, sterically stabilized liposomal Dox or 10% HPPH liposomes (10 mol % HPPH-lipid, 35 mol % cholesterol, 5 mol % DSPE-PEG-2K and 50 mol % DSPC) at dose of 10 mg/kg Dox (N=4 per group). Small blood volumes were sampled at sub-mandibular and retro-orbital locations at the indicated time points. Blood was centrifuged at 2000×g for 15 minutes. 10 µL serum was added to 990 µL extraction buffer (0.075N HCl, 90% isopropanol) and stored for 20 minutes at −20° C. The samples were removed and warmed up to room temperature and centrifuged for 15 minutes at 10,000× g. The supernatants were collected and analyzed by fluorescence. Dox concentrations were determined from standard curves. Non-comparmental pharmacokinetics parameters were analyzed by PKsolver.

Tumor drug uptake. Five week old female nude mice (Jackson Labs, #007850) were inoculated with 5×10$^6$ MIA Paca-2 cells on both flanks and randomly grouped when the sizes of the tumors reach 6-8 mm (n=4). 1 h post i.v. injection with 5 mg/kg or 10 mg/kg Dox-PoP stealth liposomes, mice were treated 350 mW/cm$^2$ from a 665 nm laser diode (RPMC laser, LDX-3115-665) for 15 min or 30 min on one flank. Mice were sacrificed immediately after treatment and tumors were collected. For tumor drug deposition determination, tumors were homogenized in nuclear lysis buffer [0.25 mol/L sucrose, 5 mmol/L Tris-HCl, 1 mmol/l MgSO4, 1 mmol/L CaCl$_2$ (pH 7.6)] and extracted overnight in 0.075N HCl 90% isopropanol. Dox and Pyro-phospholipid was determined via fluorescence measurements.

Tumor temperature and blood flow. Mice bearing MIA Paca-2 tumors were grouped into 4 groups: Dox-PoP+laser (350 mW/cm$^2$), Dox-PoP+laser (250 mW/cm$^2$), laser alone (350 mW/cm$^2$) and no laser control (n=3-4). Mice in the first two groups were i.v. injected with 7 mg/kg Dox-PoP. 1 hour post injection, mice were anesthetized and placed on a heating pad to maintain body temperature around 35° C. Tumor blood flow were measured by laser Doppler (moorLDI2-IR) in single spot mode. 665 nm laser illumination for phototreatment was initiated 5 minutes after blood flow stabilized. After 30 minutes of illumination, mice were monitored for another 10 minutes. Data were analyzed as % flow rate compared to that of the first five minutes. Tumor temperatures during the treatment courses were recorded by an infrared camera (FLIR ix series).

Survival study. 5×10$^6$ MIA Paca-2 cells (obtained from ATTC) were injected in the right flank female nude mice (5 weeks, Jackson Labs, #007850). When tumor volumes reached 4-6 mm in diameter, mice bearing MIA Paca-2 tumors were grouped as follows: 1) Saline control; 2) Dox-PoP-laser; 3) Empty PoP+laser; 4) Dox-PoP+laser. N=5-6. Dose for Dox-PoP is 7 mg/kg for Dox and the dose of PoP was adjusted to be equivalent to that of Dox-PoP 7 mg/kg (Dox to lipid loading ratio 1:5), which is 1.225 mg/kg (1.21 µmol/kg Pyro-phospholipid). For the different dosing experiment, another two groups Dox-PoP+laser (3 mg/kg based on Dox) and Dox-PoP+laser (5 mg/kg based on Dox) were studied. 21 mg/kg of sterically stabilized liposomal Dox (HSPC:CHOL:DSPE-PEG-2K=56.3:38.4:5.3% mole) was used for standard treatment of Doxil®. Free Dox 7 mg/kg was used as a free drug control. 1 h after intravenous injection, tumors that need laser treatment were all irradiated at a fluence rate of 300 W/cm$^2$ for 16 min 40 s (total fluence 300 J/cm$^2$). HPPH was diluted in PBS containing 2% ethanol and 0.2% Tween 80 and injected at a dose of 1.21 µmol/kg. Light treatment was performed 24 h post injection. Tumor size was monitored 2-3 times per week and tumor volumes were estimated by measuring three tumor dimensions using a caliper and the ellipsoid formula: Volume=$\pi \cdot L \cdot W \cdot H/6$, where L, W and H are the length, width and height of the tumor, respectively. The weights of the mice were monitored every week. MIA PaCa-2 mice were sacrificed when the volume exceeded 10 times of its initial volume.

Statistical analysis. All data were analyzed by Graphpad prism (Version 5.01) software as indicated in figure captions.

For Kaplan-Meier survival curve, each pair of group were compared by Log-rank (Mantel-Cox) test. Bonferroni method is used to adjust for multiple comparisons. Differences were considered significant at p<0.05. Median survival is defined as the time at which the staircase survival curve crosses 50% survival.

Results. It was reported that the PoP HPPH-lipid, but not Pyro-phospholipid, could entrap cargo when liposomes were form with 95 molar % PoP and Dox-loaded liposomes were subsequently prepared with 10 molar % HPPH-lipid PoP. Pyro-phospholipid was reexamined due to its extreme ease of synthesis and lack of stereocenters. Liposomes were prepared with distearoylphosphocholine (DSPC), Cholesterol (CHOL), DSPE-PEG-2K and Pyro-phospholipid. 5 molar % DSPE-PEG-2K was included and the remaining lipids were varied as indicated in FIG. 1A. Increasing amounts of Pyro-phospholipid prevented the liposomes from actively loading Dox using an internal ammonium sulfate gradient at 60° C., an established method for liposomal drug loading. However, this effect could be countered by increasing the cholesterol concentration. Liposomes with higher pyro-phospholipid concentrations could be loaded by including higher cholesterol concentrations. Liposomes with 30 molar % cholesterol could effectively load Dox, but not when amounts of Pyro-phospholipid as little as 1 molar % were included in the formulation. With 35 molar % cholesterol, Dox could only be loaded into liposomes containing small amounts of Pyro-phospholipid (0-2 molar %). The maximal amount of pyro-phospholipid that could be incorporated in Dox-loaded liposomes increased to 5 and 8 molar % when 40 and 45 molar % cholesterol were included in the formulation, respectively. This phenomenon with relatively abrupt loading behavior was both surprising and unexpected and was not observed in conventional liposomes lacking Pyro-phospholipid. As shown in FIG. 1B, Dox loading with a relatively high drug to lipid ratio (1:5) was also impacted by the cholesterol content. Unlike conventional liposomes, which loaded Dox in all conditions, PoP liposomes formed with 2 molar % pyro-phospholipid could only be loaded if more than 35% cholesterol was included. Pyro-phospholipid PoP liposomes with 45 molar % cholesterol enabled robust active loading of Dox.

Figure 10:
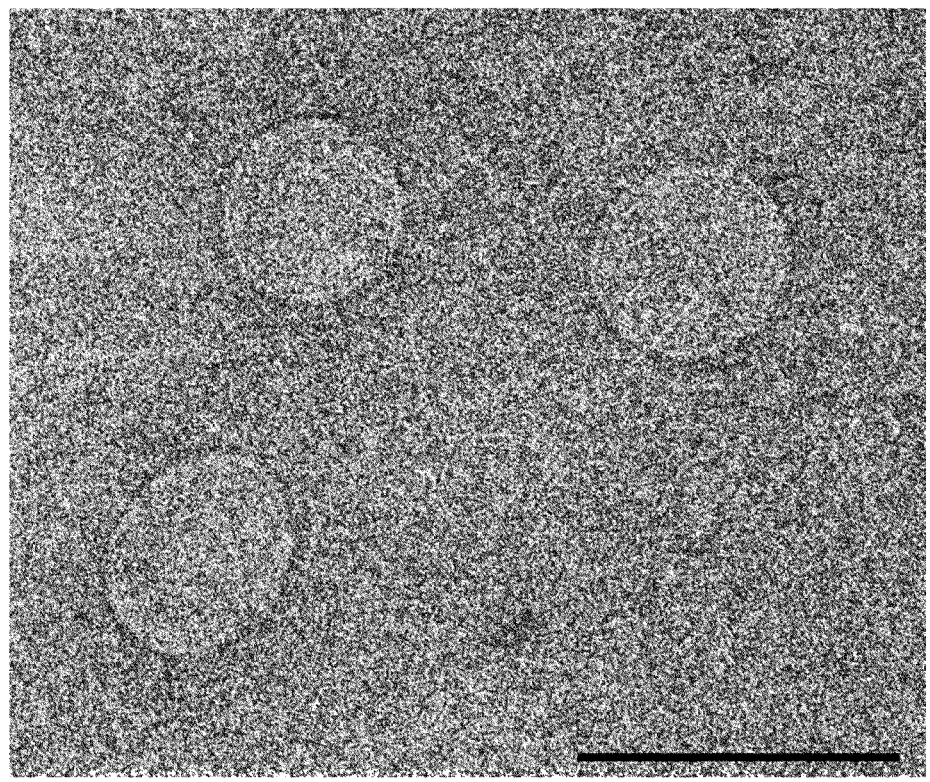
FIG. 10. Structure of empty PoP liposomes. Cryo-electron micrographs of Dox-PoP liposomes formed with a DSPC: CHOL:PEG-lipid:PoP molar ratio of 53:40:5:2. Scale bar indicates 100 nm.

To characterize the morphology of the Dox-PoP liposomes cryo-electron microscopy was used. Liposomes were formed with [DSPC:CHOL:PEG-lipid:Pyro-phospholipid] at a molar ratio of [53:40:5:2] with 1:5 Dox-to-lipid loading ratio. Electron micrographs revealed an unexpected asymmetric structure (FIG. 1C). Each Dox-loaded liposome enclosed a prominent electron dense object (indicated by arrows) that was absent from the same liposomes not loaded with Dox (FIG. 10). These were presumably Dox-sulfate precipitates and were typically located off-center. The part of the bilayer near the Dox precipitate had reduced curvature.

FIG. 1D demonstrated that loading of Pyro liposomes was affected by the drug to lipid ratio. The maximum amount of doxorubicin can be loaded for Pyro liposomes with 2 molar % pyro-phospholipid 40 molar % Cholesterol is 1:5 (Dox to lipid molar ratio), above that less than 10% of doxorubicin could be loaded. However, this is not the case for Pyro-phospholipid free liposomes with the loading efficiency gradually decrease along with higher Dox to lipid molar ratio.

Figure 2:
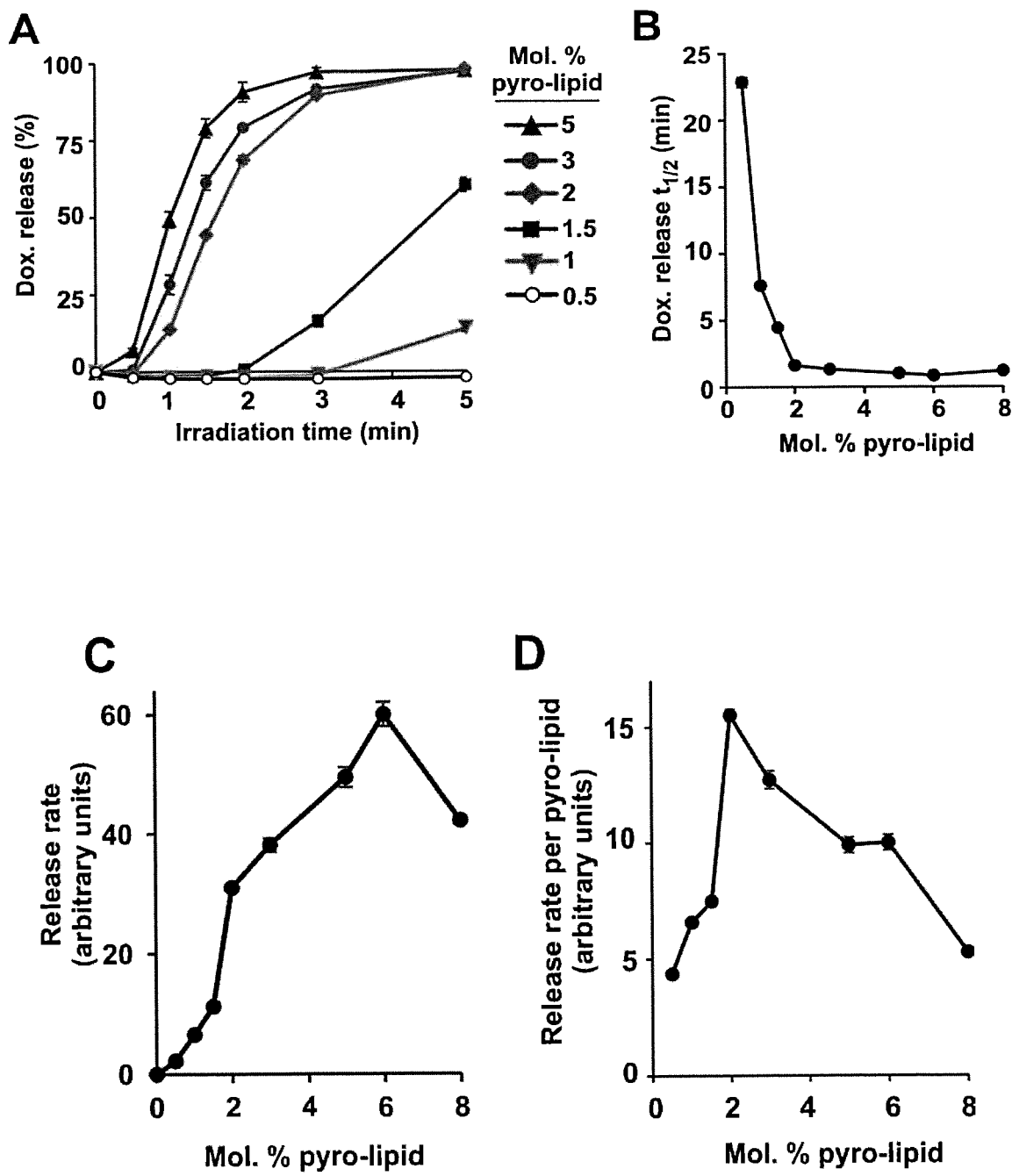
FIG. 2. Effect of PoP concentration on the rate of light-triggered Dox release. A) Real-time Dox release from PoP liposomes during 665 nm laser irradiation with varying amounts of Pyro-phospholipid incorporated. No detectable release occurs without laser irradiation. B) Laser irradiation time required for PoP liposomes to release 50% of the loaded Dox. C) Light-induced Dox release rate for PoP liposomes. D) Light-induced Dox release rate normalized by the amount of Pyro-phospholipid. Data show mean+/−Standard Deviation (S.D.). for n=3. All measurements were recorded in 50% bovine serum at 37° C.

Light-triggered release was assessed in vitro with Dox-PoP liposomes at 37° C. in 50% bovine serum. As shown in FIG. 2A, increasing amounts of PoP led to faster NIR light-induced release rates, with full release being achieved in a few minutes for most formulations. The fastest times to achieve 50% release occurred in liposomes containing between 2-8 molar % PoP (FIG. 2B,C). However when the release rate was normalized to the amount of pyro-phospholipid in the membrane, 2% pyro-phospholipid was found to be optimal on a per pyro basis (FIG. 2D). In other words, if a set dose of photosensitizer was to be injected, having it in the form of 2 molar % PoP liposomes would result in the greatest amount of light-triggered Dox release. 2% PoP was therefore selected for future experiments since in addition to providing the fastest release per unit PoP, the diminished PoP concentration reduces potential clinical photosensitizer-related side effects such as cutaneous sunlight toxicity.

Figure 3:
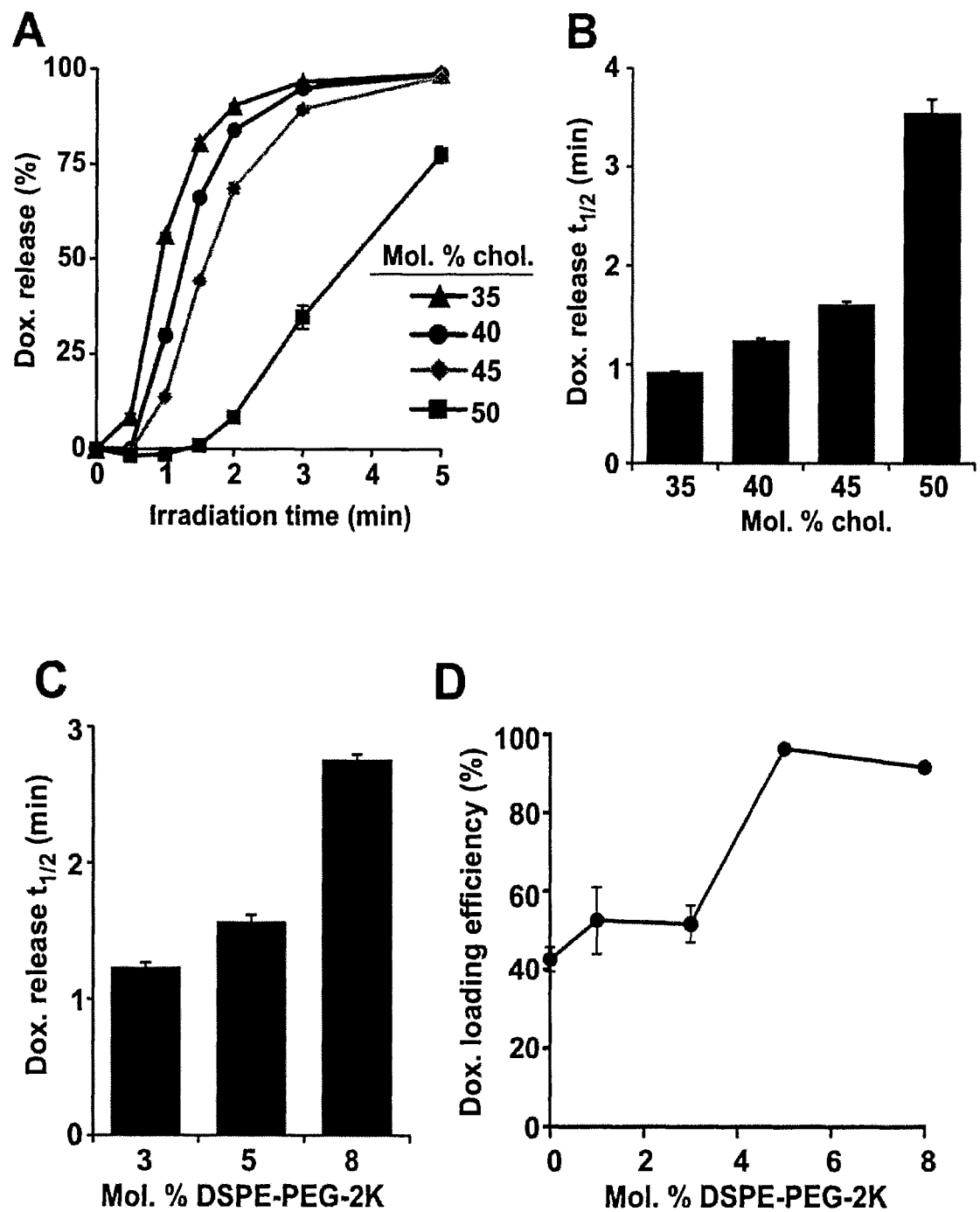
FIG. 3. Cholesterol and DSPE-PEG-2K slow light-triggered release from PoP liposomes. A) Real-time Dox release during 665 nm laser irradiation from PoP liposomes containing 2 molar % Pyro-phospholipid with varying amounts of cholesterol. Laser irradiation time required for PoP liposomes to release 50% of loaded Dox as a function of incorporated B) Cholesterol or C) DSPE-PEG-2K. Light-triggered release measurements were recorded in 50% bovine serum at 37° C. D) Dox active loading efficiency in liposomes made with varying amounts of DSPE-PEG-2K using a 1:5 Dox-to-lipid molar ratio. All data show mean+/−S.D. for n=3.

While increasing cholesterol enabled Dox loading in PoP liposomes (FIG. 1), it also slowed the light-triggered Dox release rate. As shown in FIG. 3A, PoP liposomes containing 35% cholesterol released Dox the fastest when exposed to NIR laser light whereas those with 50% cholesterol released the slowest. Using less cholesterol to increase release rates was not feasible since it was required to load the Dox into the liposomes. The irradiation time required to induce release of 50% Dox from PoP liposomes showed a clear trend of slower release occurring with increasing cholesterol (FIG. 3B), with substantial slowing observed with 50 molar % cholesterol. 40 molar % cholesterol provided the best balance between Dox loading efficiency and rapid light-triggered Dox release.

The effect of DSPE-PEG-2K on Dox loading and triggered release was investigated. PoP liposomes incorporating 45 molar % cholesterol (selected to encourage efficient active loading) and 2 molar % pyro-phospholipid were formed with varying amounts of DSPE-PEG-2K. As shown in FIG. 3C, the time required for 50% Dox release increased from 1.2 min to 2.8 min when 8 molar % of DSPE-PEG-2K was used in place of 3%. However, DSPE-PEG-2K also played a role in Dox loading, with optimum loading efficiency observed with 5 molar % (FIG. 3D), an amount that maintained reasonably fast triggered release (FIG. 3C). Thus, after considering each lipid component, PoP liposomes containing DSPC:CHOL:PEG-lipid:PoP with a molar ratio of 53:40:5:2 were finalized as putative stealth PoP liposomes for further evaluation.

Figure 11:
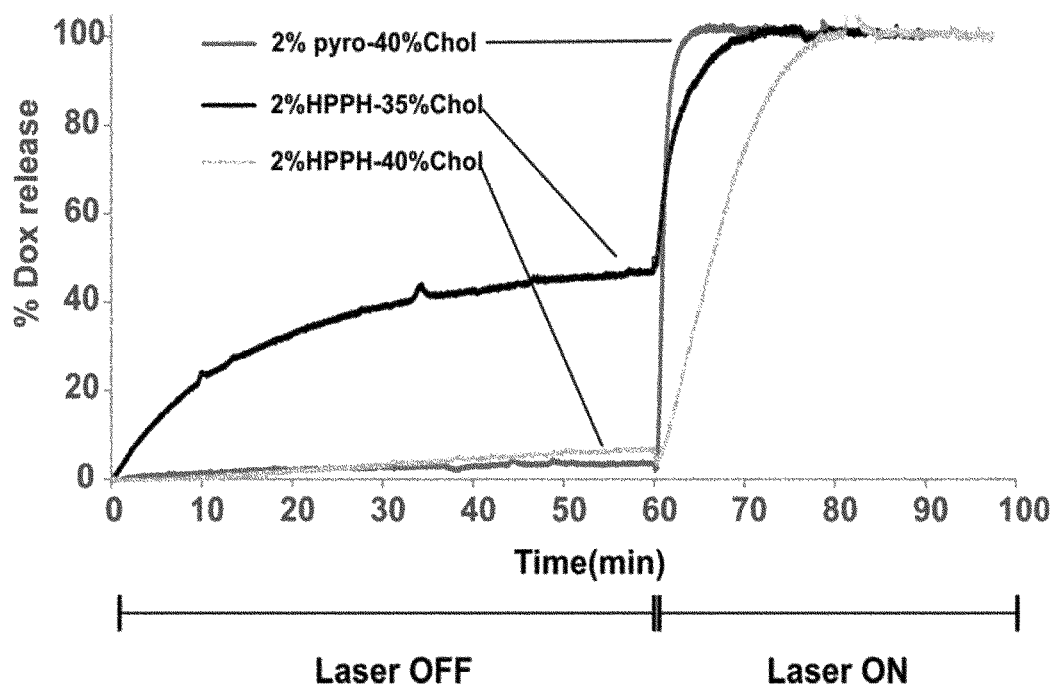
FIG. 11. Pyro-phospholipid, but not HPPH-lipid enables good serum stability and rapid light-triggered drug release. Representative real time plots of Dox release PoP liposomes made with liposomes containing 2% HPPH-lipid and 35% cholesterol, 2% HPPH-lipid and 40% cholesterol or 2% Pyro-phospholipid and 40% cholesterol. All liposomes were incubated for 1 h in 50% mature bovine serum and laser irradiation started at 1 h. All liposomes contained 5 mol % DSPE-PEG-2K and loaded at drug to lipid molar ratio of 1:5.
Figure 12:
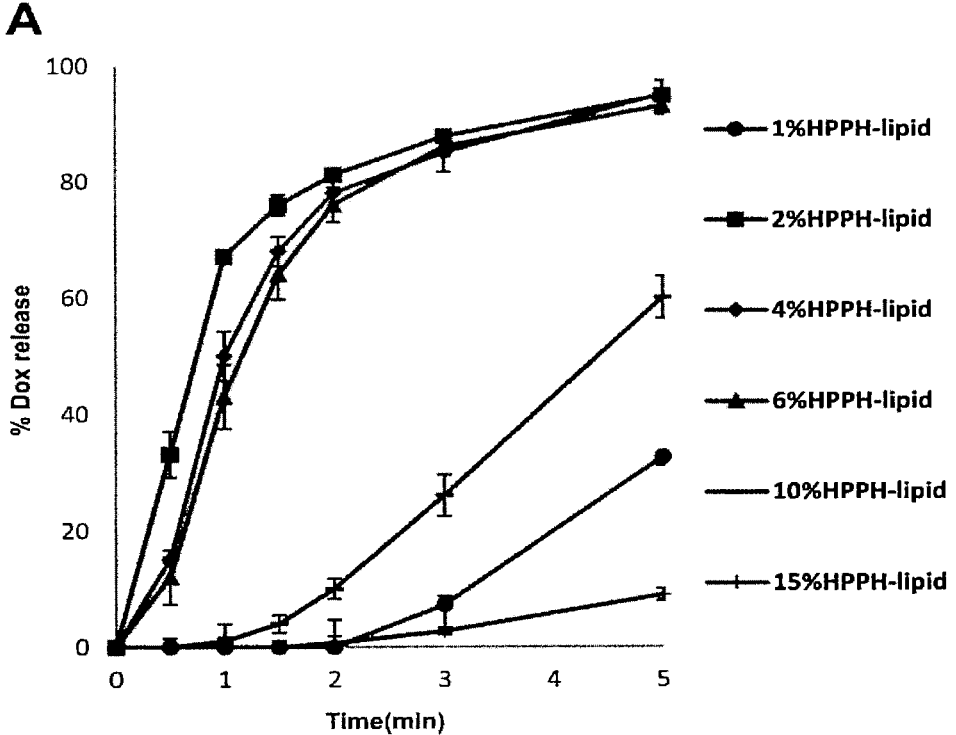
FIG. 12. 2% HPPH-lipid is optimal for rapid release of loaded Dox. 35 mol % cholesterol and 5 mol % DSPE-PEG-2K (Drug to lipid ratio of 1:8) were used for all the formulations. A) Release profiles of HPPH liposomes with variable amounts of HPPH loaded with doxorubicin upon laser irradiation. B) Time required to reach 50% release of doxorubicin for HPPH liposomes with variable amounts of HPPH-lipid. Mean±S.D., n=3.
Figure 12:
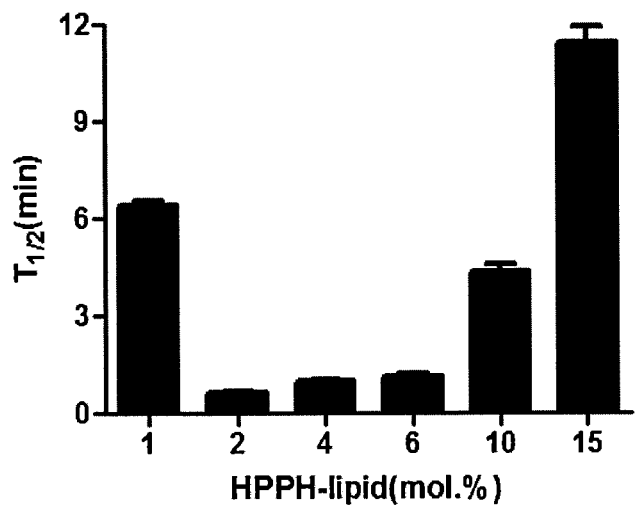
Figure 13:
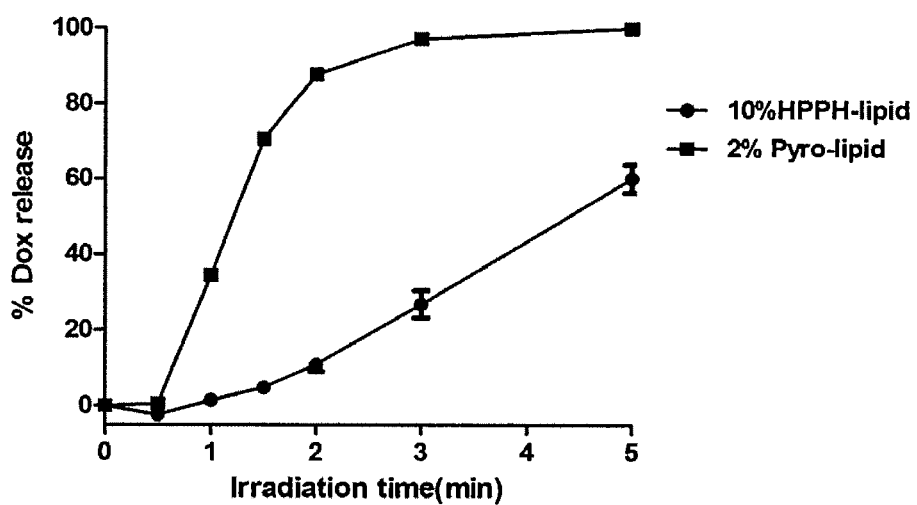
FIG. 13. Rapid NIR light-triggered release in serum using Dox-loaded stealth PoP liposomes A) Comparison of the NIR laser-induced release rate of new (2% Pyro-phospholipid) and previously reported (10% HPPH-lipid) formulations of PoP liposomes. B) Time required to reach 50% Dox release for previous (10% HPPH-lipid) and stealth PoP liposomes (2% Pyro-phospholipid) formulations. Previous formulation used 10% HPPH-lipid, 35% Cholesterol, drug to lipid loading ratio 1:8 while the stealth PoP liposome formulation consists of 2% Pyro-phospholipid, 40% Cholesterol, drug to lipid loading ratio 1:5. Mean±S.D., n=3.
Figure 13:
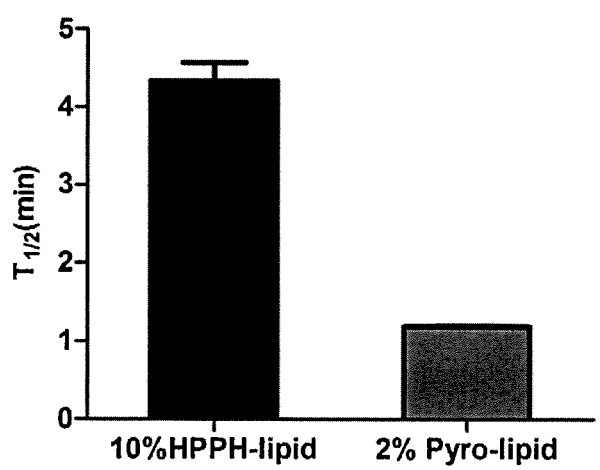

A formulation with 10 molar % HPPH-lipid was previously developed, based on the optimal release of calcein. However the optimal amount of HPPH-lipid for the release of actively loaded doxorubicin was found to be 2 molar % (FIG. 11). While HPPH-lipid conferred the conventional stealth liposomes with light-induced release properties, it also led to liposome leakiness. Unlike Pyro-phospholipid, PoP liposomes formed from HPPH-lipid could not achieve an acceptable balance between serum stability and rapid NIR laser-triggered release (FIG. 12). The developed formulation with 2 molar % Pyro-phospholipid released contents substantially faster than the previously reported formulation (FIG. 13).

Figure 4:
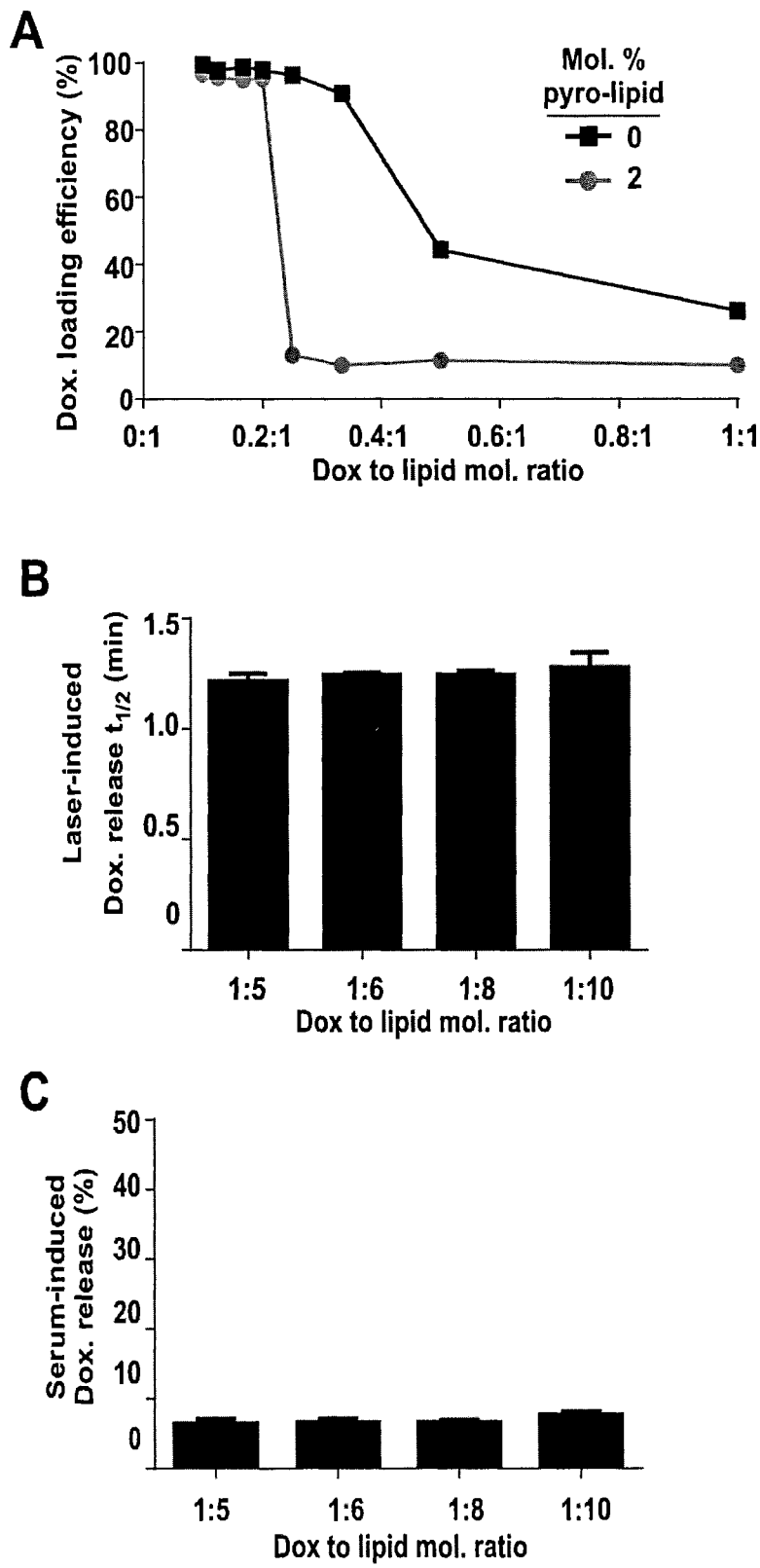
FIG. 4. Dox-to-lipid loading ratios do not impact stealth PoP liposome light-triggered release rates or in vitro serum stability. Stealth PoP liposomes were formed with DSPC: CHOL:DSPE-PEG-2K:PoP with molar ratios of 53:40:5:2. A) Dox active loading efficiency in liposomes with or without 2 molar % Pyro-phospholipid at varying drug-to-lipid molar ratios. B) Laser irradiation time required for stealth PoP liposomes to release 50% of loaded Dox as a function of Dox-to-lipid molar ratio. C) Serum stability of stealth PoP liposomes loaded at the indicated Dox-to-lipid molar ratios in 50% bovine serum, incubated at 37° C. for 4 hours. Mean+/−S.D., n=3.

The effect of the drug-to-lipid loading ratio on the encapsulation efficiency, triggered release rates and serum stability at 37° C. of stealth PoP liposomes was next investigated. FIG. 4A shows that Dox encapsulation efficiency in PoP liposomes (with 2 molar % Pyro-phospholipid) with increasing drug-to-lipid loading ratios exhibited a sharp transition point, beyond which drug loading was ineffective. This was in contrast to the same liposomes lacking pyro-phospholipid, which exhibited gradually decreasing drug encapsulation efficiencies as drug-to-lipid loading ratios increased. The highest drug-to-lipid loading ratio that could be effectively loaded was 1:5 (displayed as 0.2:1 on the graph) and beyond that ratio less than 10% of the Dox could be loaded.

For Pyro-phospholipid PoP liposomes, there was no relationship between the drug loading ratio and the rate of light-triggered drug release and rates of release were highly consistent between all samples (FIG. 4B). FIG. 4C shows that PoP liposomes with variable loading ratios all exhibited excellent serum stability in vitro. A drug to lipid ratio of 1:5 was selected for further use since it minimizes the amount of injected Pyro-phospholipid to avoid potential photosensitizer induced side effects.

Figure 5:
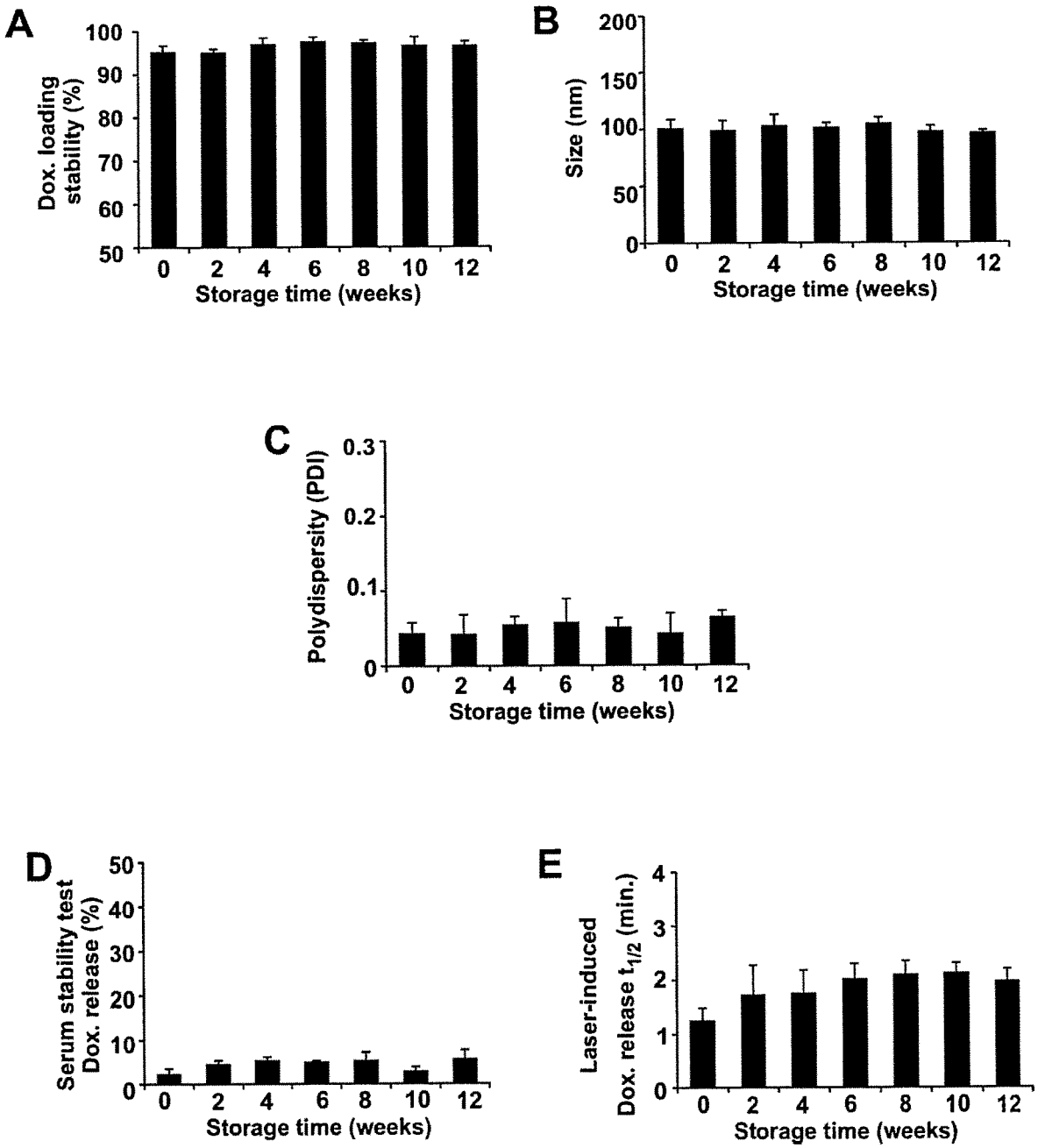
FIG. 5. Storage stability of Dox-loaded stealth PoP liposomes. Liposomes were stored at 4° C. A) Dox retention; B) liposome size; and C) liposome polydisperity. D) In vitro serum stability of loaded Dox following 6 hours incubation at 37° C. in 50% bovine serum. E) Laser irradiation time required for release 50% of loaded Dox in 50% bovine serum at 37° C. Data show mean+/−S.D. for n=3 separately prepared batches of liposomes.

The long term storage stability of stealth PoP liposomes was evaluated (FIG. 1C). The liposomes were stored at 4° C. in closed amber vials without any other precautions and liposomes were periodically removed for routine analysis. Loading stability, size, polydisperity, serum stability and light triggered release rates were assessed every two weeks for 3 months with 3 separately prepared batches of liposomes. As shown in FIG. 5A, over 95% of the Dox remained stably trapped inside the stealth PoP liposomes. FIGS. 5B and 5C show that for all separately prepared batches, the size of stealth PoP liposomes remained close to 100 nm, together with a low polydisperity index of close to 0.05, indicating a small and monodisperse population of nanoparticles. Consistently over the storage period, less than 10% of the loaded Dox leaked from the liposomes when incubated for 6 hours in 50% bovine serum at 37° C. in vitro (FIG. 5D). Thus, for a phototreatment that occurs shortly after intravenous administration of the liposomes, little serum-induced leakage would be predicted to occur. The NIR light-triggered Dox release rate from stealth PoP liposomes remained relatively stable during storage, with close to two minutes of irradiation being required to achieve 50% Dox release (FIG. 5E). Thus, despite the high drug-to-lipid loading ratio of 1:5, which gave rise to unusual and asymmetric liposome morphology (FIG. 1C), stealth PoP liposomes loaded with Dox exhibited excellent storage stability by all metrics examined. They performed consistently in functional assays for being stable in serum in the absence of NIR light yet quickly releasing contents when exposed to it.

Figure 6:
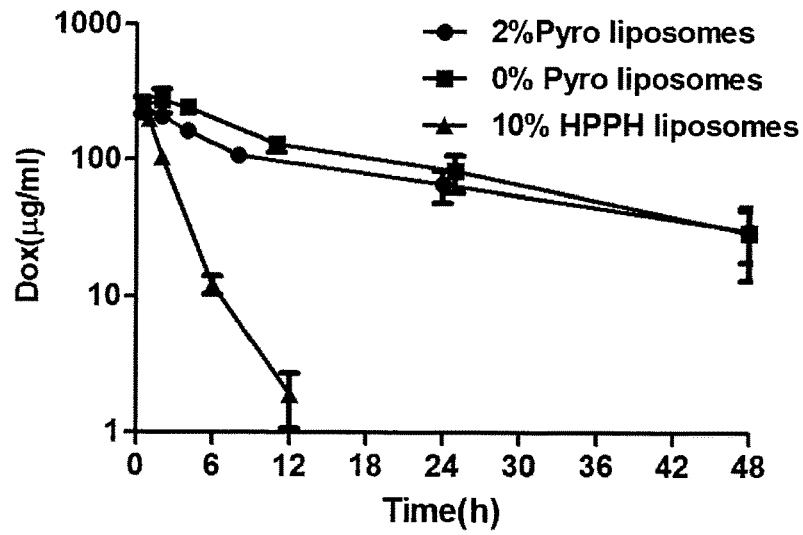
FIG. 6. Long blood circulation of Dox loaded in stealth PoP liposomes. Serum concentration of Dox loaded in indicated liposomes and intravenously administered to CD-1 mice. Values show mean+/−S.D. for n=4-5 mice per group.

The pharmacokinetic behavior of stealth PoP liposomes loaded with Dox was studied following intravenous administration to CD-1 mice. As shown in FIG. 6, encapsulated Dox demonstrated a long-circulating pharmacokinetic profile. The blood elimination time and half-life of Dox in stealth PoP liposomes was close to that of conventional stealth liposomes (containing no Pyro-phospholipid; equivalent to sterically stabilized liposomal Dox or SSL Dox). Dox-loaded stealth PoP liposomes exhibit a circulating half-life of 21.9 hours with an area under the curve (AUC) of 4837 μg/(ml*h). The half-life of SSL Dox liposomes was 16.9 hours with an area under the curve of 5695 μg/(ml*h). These formulations exhibited substantially greater circulation half-lives and AUC than previously reported PoP liposomes that included 10 molar % HPPH-lipid and 35 molar % cholesterol. Table 1 lists pharmacokinetic parameters of Dox-loaded stealth PoP liposomes and other Dox-loaded liposome formulations.

TABLE 1

Noncompartmental pharmacokinetics analysis of liposomal Dox

| | $T_{1/2}$ (h) | $C_{max}$ (μg/ml) | $AUC_{0\to\infty}$ (μg · h/ml) | $MRT_{0\to\infty}$ (h) | Cl (ml/h/g) | $V_{ss}$ (ml/g) |
|---|---|---|---|---|---|---|
| 2% Pyro liposomes | 21.9 | 250.1 | 4837 | 29.3 | 0.002 | 0.06 |
| 0% Pyro liposomes | 16.9 | 275.0 | 5695 | 22.8 | 0.002 | 0.04 |
| 10% HPPH liposomes | 1.6 | 224.2 | 581 | 2.1 | 0.02 | 0.04 |

MRT; median residence time.
AUC; the area under the product of c · t plotted against t from time 0 to infinity.
Cl, clearance.
$V_{ss}$, volume of distribution at steady state.

Figure 7:
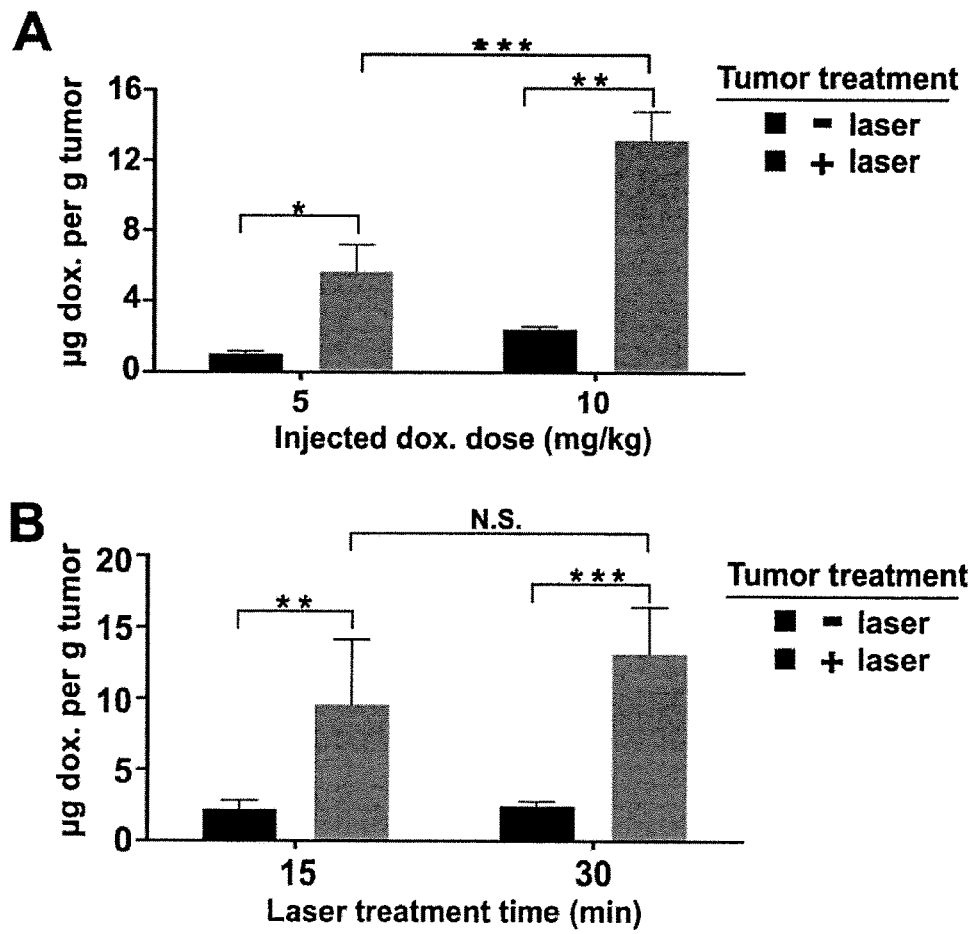
FIG. 7. Laser-induced enhanced Dox deposition from stealth PoP liposomes in a contralateral Mia Paca-2 dual tumor model. 1 hour after intravenous injection of Dox-loaded stealth PoP liposomes, tumors on only one flank of the mice were irradiated with a 665 nm laser. Immediately after irradiation, mice were sacrificed and Dox concentration in both treated and untreated tumors was determined. A) Effect of injected dose of 5 mg/kg or 10 mg/kg Dox in stealth PoP liposomes. Tumors were treated with 30 minutes of 665 nm irradiation at 350 mW/cm$^2$. B) Effect of different irradiation times of 15 or 30 minutes. Mice were injected with 10 mg/kg Dox in stealth PoP liposomes and tumors were treated with 665 nm irradiation at 350 mW/cm$^2$. There was no significant difference between 15 and 30 minutes irradiation time in terms of tumor Dox uptake. Statistical analysis were performed by Bonferroni post-test, two way ANOVA,*P<0.05, P<0.01, *P<0.001. Mean+/−S.D. for n=4 tumors per group.

Nude mice were contralaterally inoculated with the human pancreatic MIA Paca-2 cancer cells on both flanks to generate a dual tumor model for light-triggered Dox uptake studies. This method involves one tumor being treated with NIR light and the other serving as a control. Treatment time and injected dose were investigated by measuring Dox tumor uptake immediately after NIR laser treatment. 1 hour following intravenous injection with 5 mg/kg or 10 mg/kg Dox (total intravenously injected Dox dose, encapsulated in stealth PoP liposomes), tumors were laser irradiated for 15 or 30 minutes. Tumor uptake of Dox in the laser irradiated group was 6-7 fold greater than tumors receiving no laser treatment (FIG. 7A). The deposition of the drug in tumors was dependent on the injected dose, with the 10 mg/kg injected dose resulting in 13.8 μg Dox per gram of tumor (for the laser treated tumor), which was approximately double the tumor concentration of the 5 mg/kg injected dose (with a laser-treated tumor Dox concentration of 7.0 μg Dox per gram of tumor).

While the injected dose directly impacted light-triggered Dox uptake in the tumor, different light doses (applied using different irradiation times of 15 and 30 minutes) did not have as marked an effect. Mice treated with an injected dose of 10 mg/kg and irradiated for either 15 or 30 minutes resulted in 9.6 and 13.2 μg Dox per gram in laser-treated tumor tissue, respectively, and these were not statistically significantly different (FIG. 7B). Further research is required to better understand the impact of different light doses, but laser treatment could possibly be inducing partial vascular stasis, preventing more liposomes flowing into the tumors.

Figure 8:
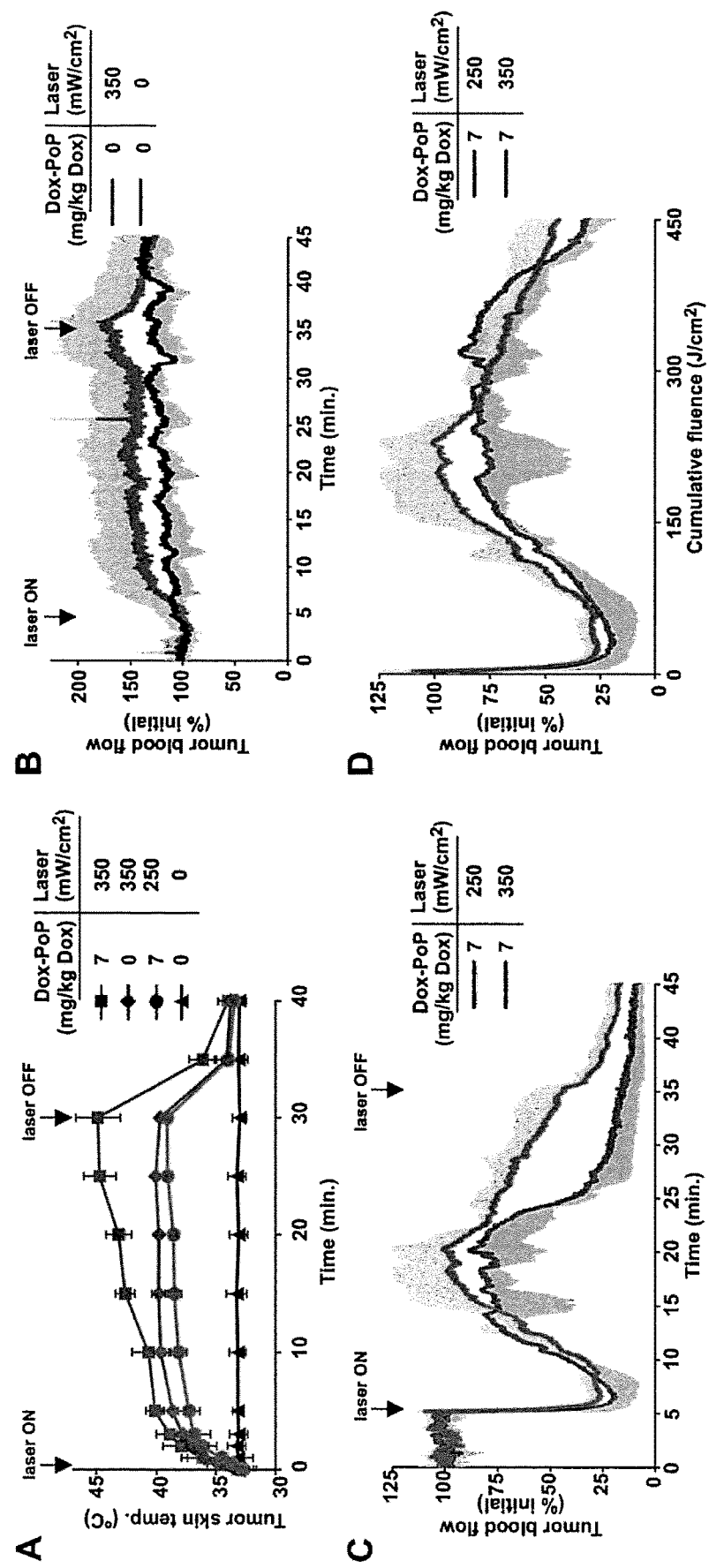
FIG. 8. Tumor surface temperature and blood flow during phototreatment with stealth PoP liposomes. A) Surface temperature of MIA Paca-2 xenograft during treatment with a 665 nm laser diode at indicated power one hour after intravenous administration of PoP liposomes at the indicated Dox dose. B) Relative change in tumor blood flow induced by the laser treatment itself. Laser was switched on at indicated fluence rate as indicated. C, D) Relative change in tumor blood flow as a function of time (C) or cumulative fluence (D) for mice one hour after intravenous administration of stealth PoP liposomes at the indicated laser fluence rates. Values indicate mean with S.D. (in a single vertical direction for blood flow data) for n=3-4 mice per group.

The effect of laser treatment on the tumor temperature was examined (FIG. 8A). One hour after 7 mg/kg Dox dosing, laser irradiation was applied at 350 mW/cm$^2$ and caused the surface temperature of the tumor to increase up to 45° C. over 30 minutes of irradiation. When the fluence rate was lowered to 250 mW/cm$^2$, the temperature increased to less than 40° C. This rise in temperature was similar to the observed tumor surface heating when 350 mW/cm$^2$ was applied, without the prior injection of PoP liposomes. Tumor blood flow was assessed with laser Doppler analysis, a technique which can non-invasively probe superficial perfusion in the investigated tissue. As shown in FIG. 8B, in the absence of PoP-liposomes, tumor blood flow was not inhibited by the 350 mW/cm$^2$ laser treatment, and increased over time by approximately 50%, possibly due to thermal heating effects. Tumors irradiated when stealth PoP liposomes were circulating in blood exhibited drastically different blood flow dynamics (FIG. 8C). Tumor blood flow initially decreased sharply, followed by an increase and then a subsequent decrease. This trend was observed at both 250 mW/cm$^2$ and 350 mW/cm$^2$ fluence rates. Vascular shutdown continued after the laser was turned off following 30 minutes of irradiation. The decrease in blood flow during laser irradiation was not due to tumor heating, since the 250 mW/cm² treatment resulted in similar heating to the drug-free 350 mW/cm² treatment, which did not show any vascular shutdown (FIG. 8B). The phenomenon of an immediate decreasing tumor flow, followed by a subsequent increase has been reported in mice with high fluence photodynamic therapy (PDT). When plotted as a function of cumulative fluence, the 250 mW/cm² and 350 mW/cm² treatments exhibited similar patterns of tumor vascular dynamics (FIG. 8D).

Figure 9:
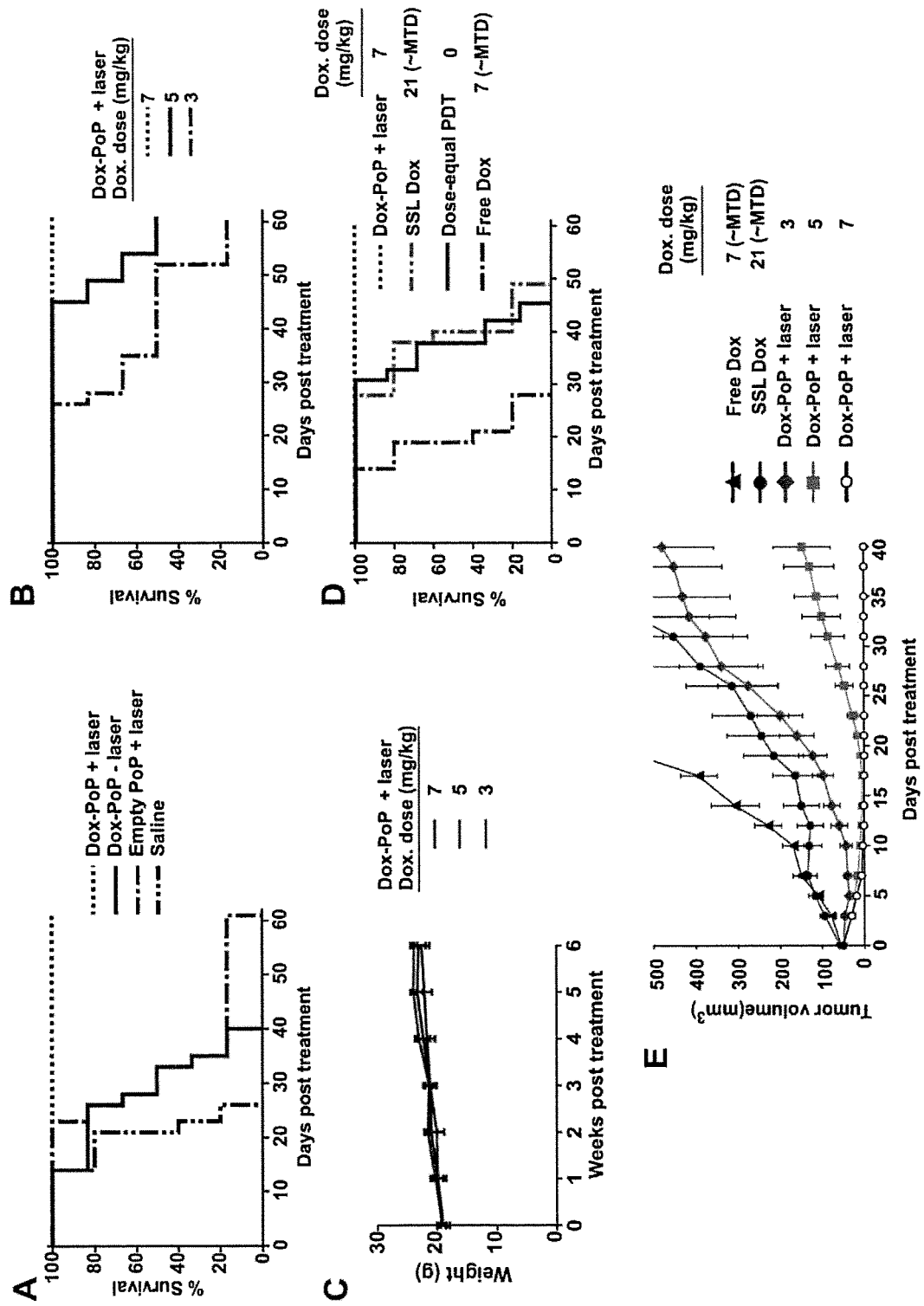
FIG. 9. Phototreatment efficacy of Dox-loaded stealth PoP liposomes. Nude mice bearing MIA Paca-2 tumors were treated when tumor diameter reached 4-5 mm and were sacrificed when tumor volume increased 10 fold. Laser treatments involved administration of 300 J/cm$^2$ of 665 nm light (300 mW/cm$^2$ over 16.7 minutes). A) Synergistic efficacy of Dox stealth PoP liposomes with laser treatment. Dox was administered at 7 mg/kg or with equivalent dosage in control groups. B) Dose response of Dox-loaded stealth PoP liposomes with phototreatment. The examined doses of 3, 5, 7 mg/kg were significantly more effective than untreated control groups (P<0.05). C) Body mass of mice that were phototreated with Dox-loaded stealth PoP liposomes. D) Dox-loaded stealth PoP liposomes with phototreatment were significantly more effective than conventional anti-tumor treatments including SSL Dox and free Dox at their maximum tolerated dose (MTD) or conventional PDT using HPPH at with the same light treatment and an equivalent photosensitizer dose (P<0.05). E) Tumor volume growth for indicated treatment groups. Mean+/−S.E. for n=5-6 mice per group.

The anti-tumor efficacy of Dox stealth PoP liposomes was assessed in nude mice bearing single MIA Paca-2 subcutaneous tumors. As shown in FIG. 9A, at a dose of 7 mg/kg Dox (or equivalent) both Dox-loaded stealth PoP liposomes alone (without laser treatment) and unloaded stealth PoP liposome with laser treatment provided some therapeutic benefit by prolonging median survival times compared to untreated control mice from 21 days to 30.5 days for both groups. However, a strong therapeutic synergy was observed for Dox-loaded stealth PoP liposomes with laser treatment, as this approach led to full survival of all mice and was significantly more effective than the two aforementioned control treatments ($P<0.05$). With a 7 mg/kg dose of Dox in stealth PoP liposomes, all phototreated tumors effectively regressed to less than 20 mm³ within two weeks of treatment and all mice survived the duration of the study (60 days) with 3 of 6 tumors permanently cured. The phototherapeutic efficacy of Dox-loaded stealth PoP liposomes at lower doses was examined (FIG. 9B). Both 3 mg/kg and 5 mg/kg Dox were highly effective in delaying tumor growth. Laser treated mice treated with Dox-PoP liposomes had a median survival time of 43.5 days with 3 mg/kg Dox, and 57 days with 5 mg/kg Dox. For mice treated with 5 mg/kg Dox, tumor regrowth was seen in only 3 of 6 mice. In all cases, Dox-loaded stealth PoP liposome phototreatments were well tolerated, as evidenced by healthy body mass in all treated mice (FIG. 9C).

As shown in FIG. 9D, phototreatment with Dox-loaded stealth PoP liposomes was substantially more effective than single-dose treatments of conventional chemotherapy or PDT. Free Dox, at its maximum tolerated dose of 7 mg/kg was ineffective treatment against MIA Paca-2 tumors, with no significant tumor growth delay compared to control mice (median survival 19 vs 21 days). Sterically stabilized Dox (SSL Dox) could be administered at a three times higher maximum tolerated dose compared to the free drug, and improved survival compared to control (median survival 40 days vs 21 days, $P<0.05$). Conventional PDT exhibited a similar tumor growth inhibition (median survival 38 days) when administered with an equivalent light dose and equivalent injected dose of HPPH, a photosensitizer with similar spectral properties as Pyro-phospholipid and currently in clinical trials. Dox-loaded stealth PoP liposomes with laser treatment was significantly more effective than these three anti-cancer modalities which have all been used in the clinic. Standard treatment of SSL Dox at a high dose (21 mg/kg) later on developed rashes on the feet of the mice which is typical symptom of palmar-plantar erythrodysesthesia (PPE) at high dose of stealth liposomal doxorubicin. Tumor volumes revealed that all Dox phototreatments with stealth PoP liposomes were more efficacious than the maximum tolerated doses of free and SSL Dox (FIG. 9E). Stealth PoP liposome phototreatment with 3 mg/kg Dox was slightly more effective than SSL Dox at 21 mg/kg. Even with presumed faster blood clearance observed with lower injected doses of liposome, PoP liposomes can be used at least 7 times lower dosage with superior therapeutic efficacy to conventional SSL Dox. These results are encouraging for achieving tumor ablation with minimal side effects.

Discussion. In this study, we systematically examined all lipid components of PoP liposomes to successfully develop a formulation that 1) could be actively loaded with Dox with high efficacy and loading ratios; 2) was stable in vitro during storage and in serum; 3) had long circulating times in vivo; and 4) could rapidly release Dox when exposed to NIR light. Increasing amounts of cholesterol enabled active loading with increasing amounts of PoP, which itself tended to destabilize the bilayer and prevent Dox loading. Although cholesterol is known to enhance liposome stability, further studies are required to better determine the role cholesterol plays in the function and structure of PoP liposomes. Increasing amounts of cholesterol also slowed down light-triggered Dox release, as did DSPE-PEG-2K. However both components were required for effective Dox loading. High Dox-to-lipid loading ratios (1:5) were possible and gave rise to unusual liposomal morphology as demonstrated in FIG. 1C. How cholesterol and DSPE-PEG-2K slows light triggered drug release is of interest and further elucidation of mechanistic aspects is required.

Increasing amounts of Pyro-phospholipid inhibited the loading of Dox into PoP liposomes, an effect which had to be countered by increasing the cholesterol content. Increased Pyro-phospholipid also increased the light-triggered release rate. An optimal amount of 2 molar % Pyro was selected since this gave the most rapid release rate when normalized by the amount of Pyro-phospholipid in the bilayer. Although Pyro-phospholipid has been shown to be well-tolerated in mice at intravenous doses as high as 1 g/kg, administration of lower doses of molecules that are photosensitizers to patients is preferred to avoid undesired sunlight toxicity or edema formation in the irradiated area as observed in PDT treatment. Using the developed Dox-loaded stealth PoP liposome formulation, Dox dosing at a low human dose of 5 mg/m², would correspond to PoP dosing in the ballpark of 1 mg/m² or 0.03 mg/kg, a photosensitizer dose that is orders of magnitude less than clinically approved Photofrin, which is usually administered at 2 mg/kg doses.

Immediately following laser treatment, a 6-7 fold increase of tumor uptake of doxorubicin was observed. The striking increase in tumoral drug concentration is likely an important factor for the effectiveness of this treatment. The enhanced drug accumulation can be due to a combination of drug release, hyperthermia-mediated vessel permeabilization, and also PDT-induced vascular permeability effect. Both triggered release and PDT can be used as means to enhance drug delivery. Further studies are needed to thoroughly ascertain the contributions of each mechanism on enhanced drug uptake and enhanced bioavailability. When treatment time with 350 mW/cm² irradiation was increased from 15 to 30 minutes, tumor drug uptake increased, but not with statistical significance. As shown in FIG. 8C, after 20 minutes of irradiation, blood flow decreased in the tumor, limiting the amount of drug that could be deposited. PDT induced microvascular stasis was likely occurring and inhibiting further supply of liposomes to the irradiated volumes. For tumor growth inhibition studies, a 16.7 minute treatment was performed with an intermediate fluence rate of 300 mW/cm², so that tumor heating did not exceed 43° C., and intra-treatment vascular shutdown during was minimal. Future directions include combining this treatment with anticoagulants, which might reduce PDT-induced vascular stasis and further improve tumor drug uptake.

Conclusion. A robust sterically-stabilized, long-circulating stealth PoP liposome formulation which can be triggered by NIR light to release encapsulated drugs was developed. Dox-loaded stealth PoP liposomes exhibited long term storage stability. PoP liposome chemophototherapy anti-tumor efficacy was superior to conventional PDT (using HPPH) and to a maximum tolerated single dose of Dox, administered freely or in long-circulating liposomes.

EXAMPLE 2

This example further describes the preparation of PoP-liposomes, and loading and release of cargo.

Figure 14:
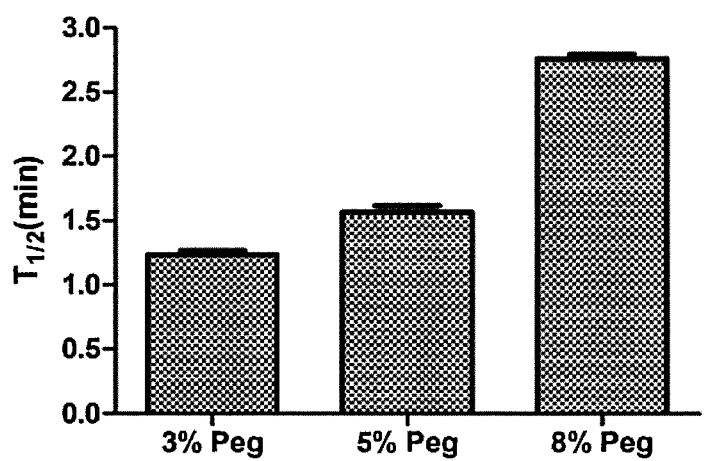
FIG. 14. 5% PEG-lipid maintains fast release rate and high loading efficiency. Time required for 50% Release of 2% Pyro-phospholipid 45% Cholesterol liposomes with 3%, 5% and 8% PEG-lipid in 50% filtered mature bovine serum at 37° C. (A); Loading efficiency of liposomes made with 0%, 1%, 3%, 5% and 8% PEG-lipid, 45% Cholesterol (B). Mean+/−S.D., n=3.
Figure 14:
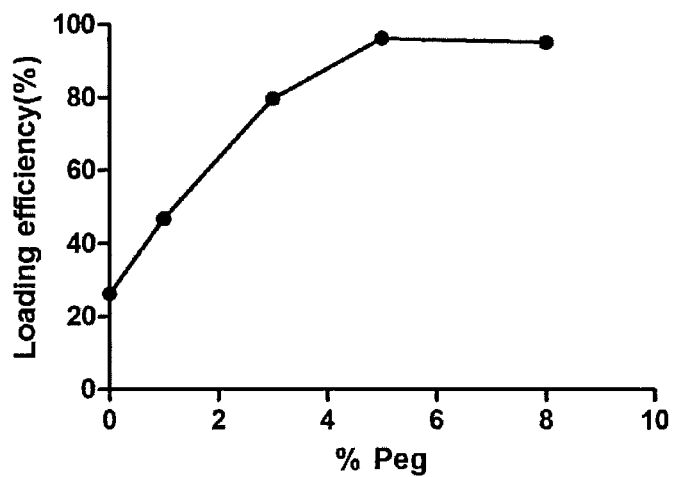

Samples with 45% cholesterol and 2% pyro-phospholipid were made with varying amounts of PEG (FIG. 14). The PEG-lipid content of the liposomes was found to have an effect on the loading and the release of doxorubicin, with optimum loading at PEG-lipid content of 5% and faster release with 3% PEG-lipid. 5% PEG-lipid was shown to be the optimum as it provided to greatest drug loading with a good release rate.

Figure 15:
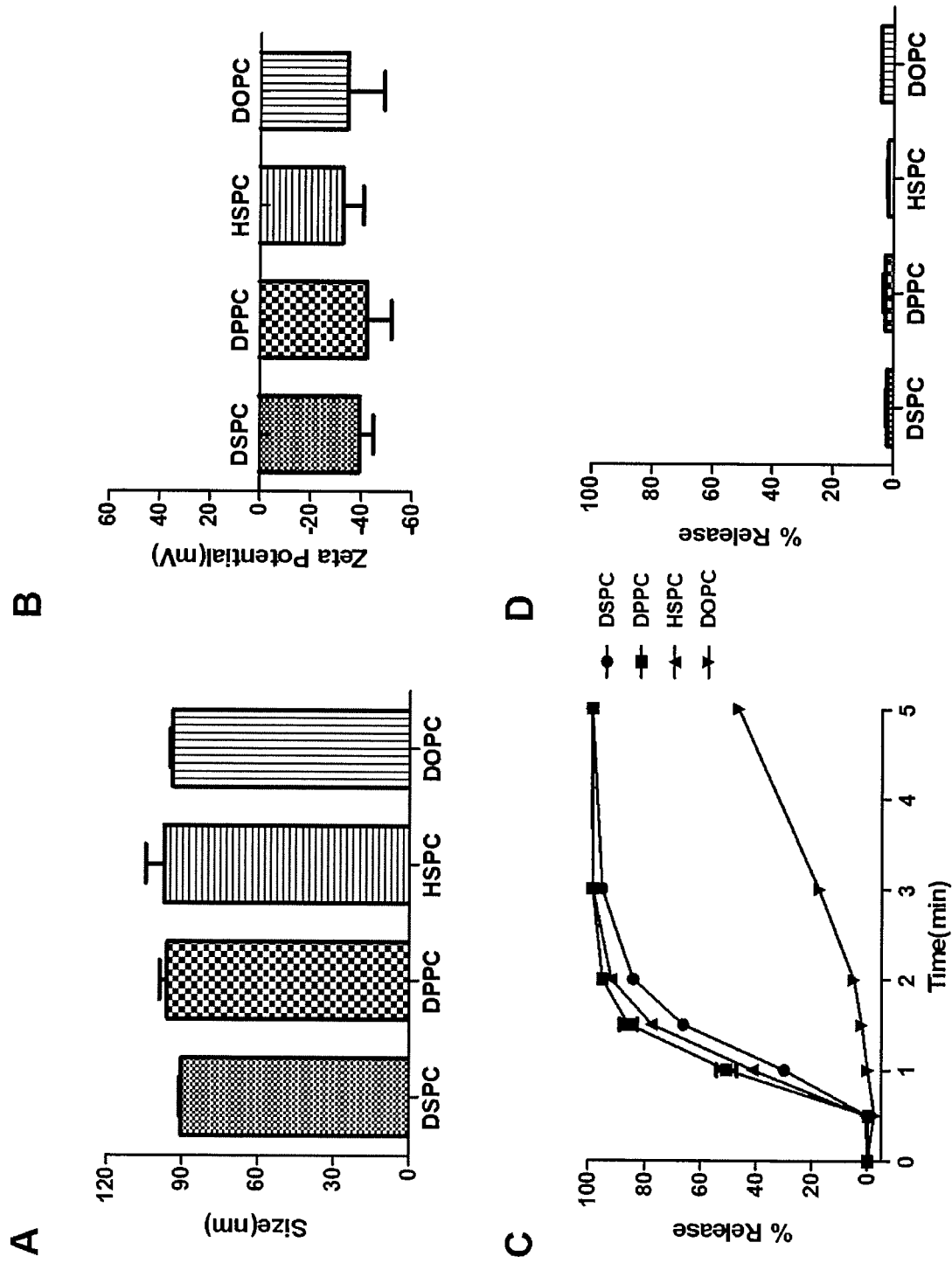
FIG. 15. Various Phosphatidylcholine (PC) lipids including DSPC, DPPC, HSPC and DOPC can be used for Pyro liposomes release while maintaining serum stability. Sizes of Pyro liposomes loaded with doxorubicin made with 53 molar % DSPC, DPPC, HSPC and DOPC were tested in PBS (A); Zeta Potential of Pyro liposomes made with 53 molar % DSPC, DPPC, HSPC and DOPC were tested in distilled H$_2$O (B); Triggered release in 50% filtered mature bovine serum of Pyro liposomes made with 53 molar % DSPC, DPPC, HSPC or DOPC (C). Stability in 50% filtered mature bovine serum at 37° C. for 4 h (D). All the formulations are made with 53 molar % DSPC, DPPC or HSPC or DOPC, 5 molar % PEG2k, 40 molar % Cholesterol and 2 molar % Pyro-phospholipid, doxorubicin to lipid loading ratio 1:8.
Figure 16:
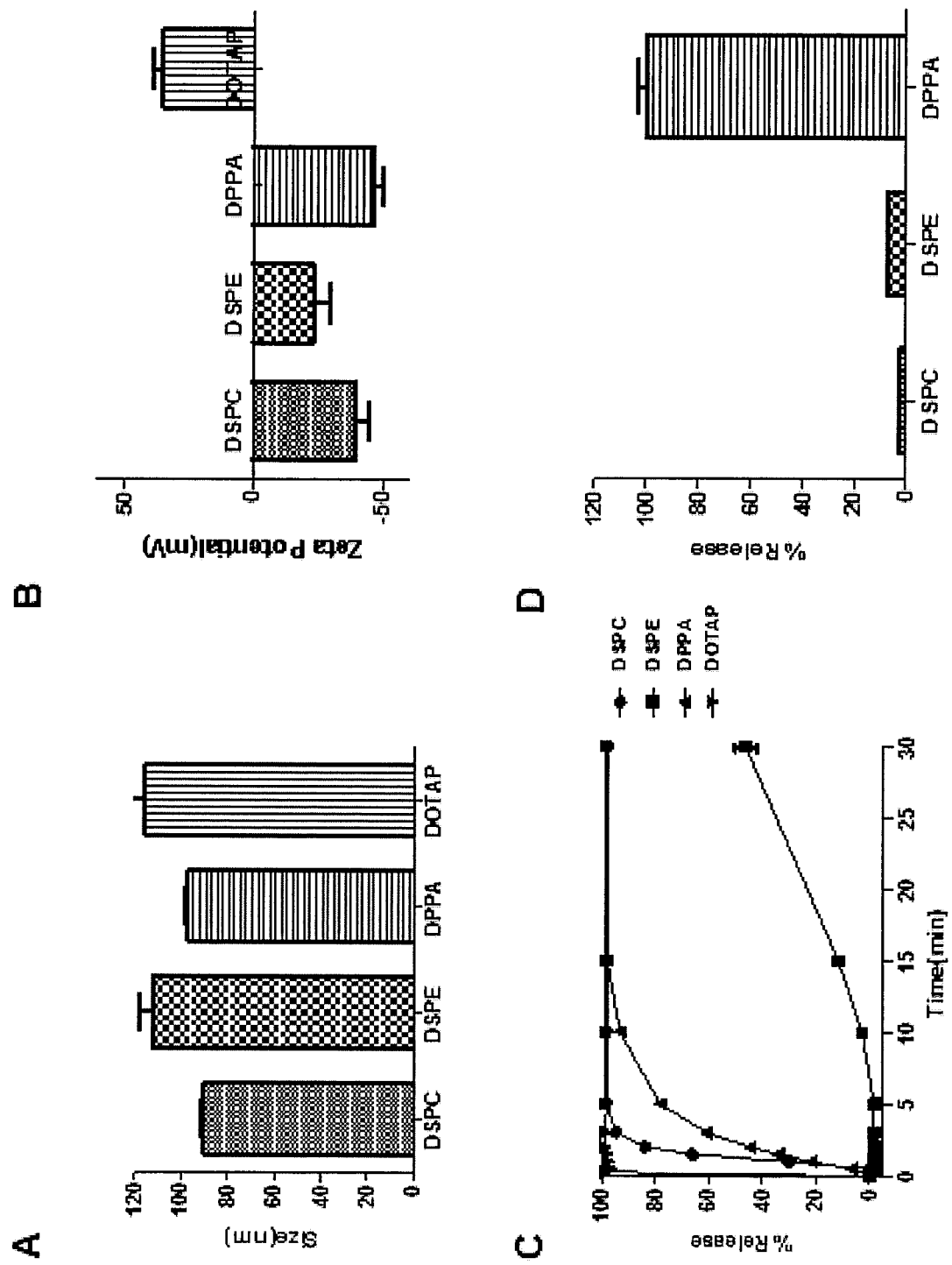
FIG. 16. Cationic lipids DOTAP and Phosphatidylethanolamine (PE) and Phosphatidic acid (PA) lipids can also be used for Pyro liposomes for light triggered release. Sizes of Pyro liposomes loaded with doxorubicin made with 43 molar % DOTAP, 53 molar % DSPE or DPPA were tested in PBS (A); Zeta potential of Pyro liposomes made with 43 molar % DOTAP, 53 molar % DSPE or DPPA were tested in distilled $H_2O$ (B); Triggered release in 50% filtered mature bovine serum of Pyro liposomes made with 43 molar % DOTAP, 53 molar % DSPE or DPPA (C). Stability of Pyro liposomes made with 43 molar % DOTAP, 53 molar % DSPE or DPPA in 50% filtered mature bovine serum at 37° C. for 4 h (D). Liposomes containing DSPE or DPPA are made with 53 molar DSPE or DPPA, 5 molar % PEG2k, 40 molar % Cholesterol and 2 molar % Pyro-phospholipid, doxorubicin to lipid loading ratio 1:8. Liposomes containing cationic lipids DOTAP are made with 43 molar % DSPC, 20 molar % DOTAP, 35 molar % Cholesterol and 2 molar % Pyro-phospholipid.
Figure 17:
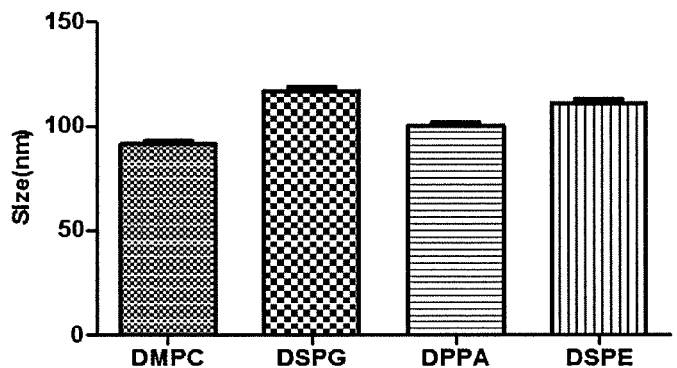
FIG. 17. PC, Phosphatidylglycerol (PG), PA and PE lipids can be used for Pyro liposomes for light triggered release. Sizes of Pyro liposomes loaded with irinotecan (IRT) made with 53 molar % DMPC, DSPG, DPPA or DSPE were tested in PBS (A); Zeta potential of Pyro liposomes made with 53 molar % DMPC, DSPG, DPPA or DSPE were tested in distilled $H_2O$ (B); Triggered release in 50% filtered mature bovine serum of Pyro liposomes made with 53 molar % DMPC, DSPG, DPPA or DSPE (C). All the formulations are made with 53 molar % DMPC, DSPG, DPPA or DSPE, 5 molar % PEG2k, 40 molar % Cholesterol and 2 molar % Pyro-phospholipid, irinotecan to lipid loading ratio 1:8.
Figure 17:
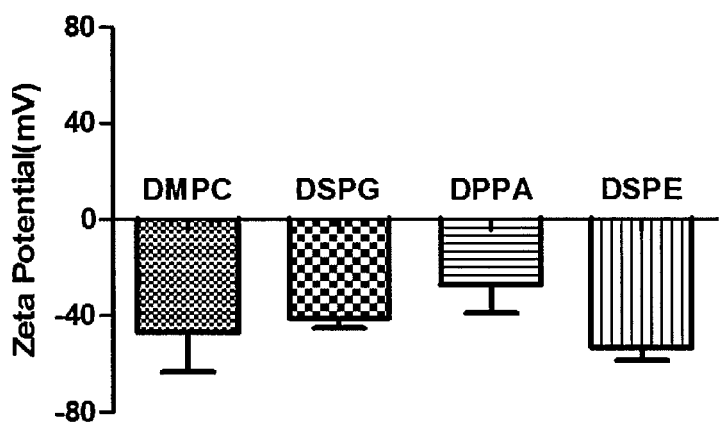
Figure 17:
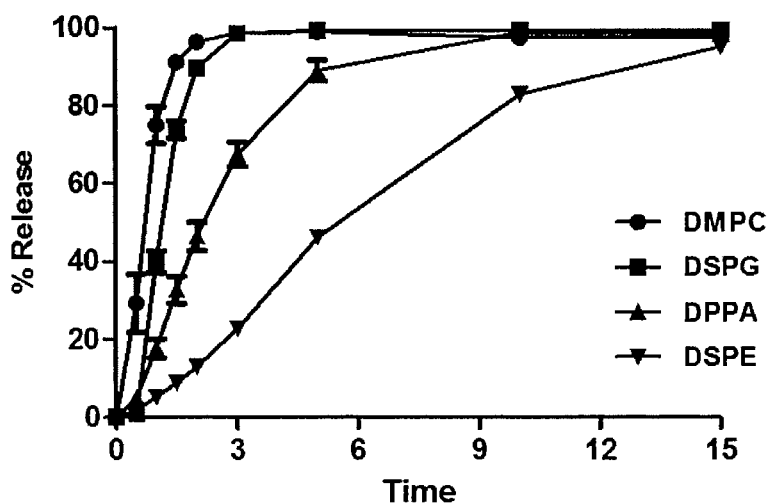
Figure 18:
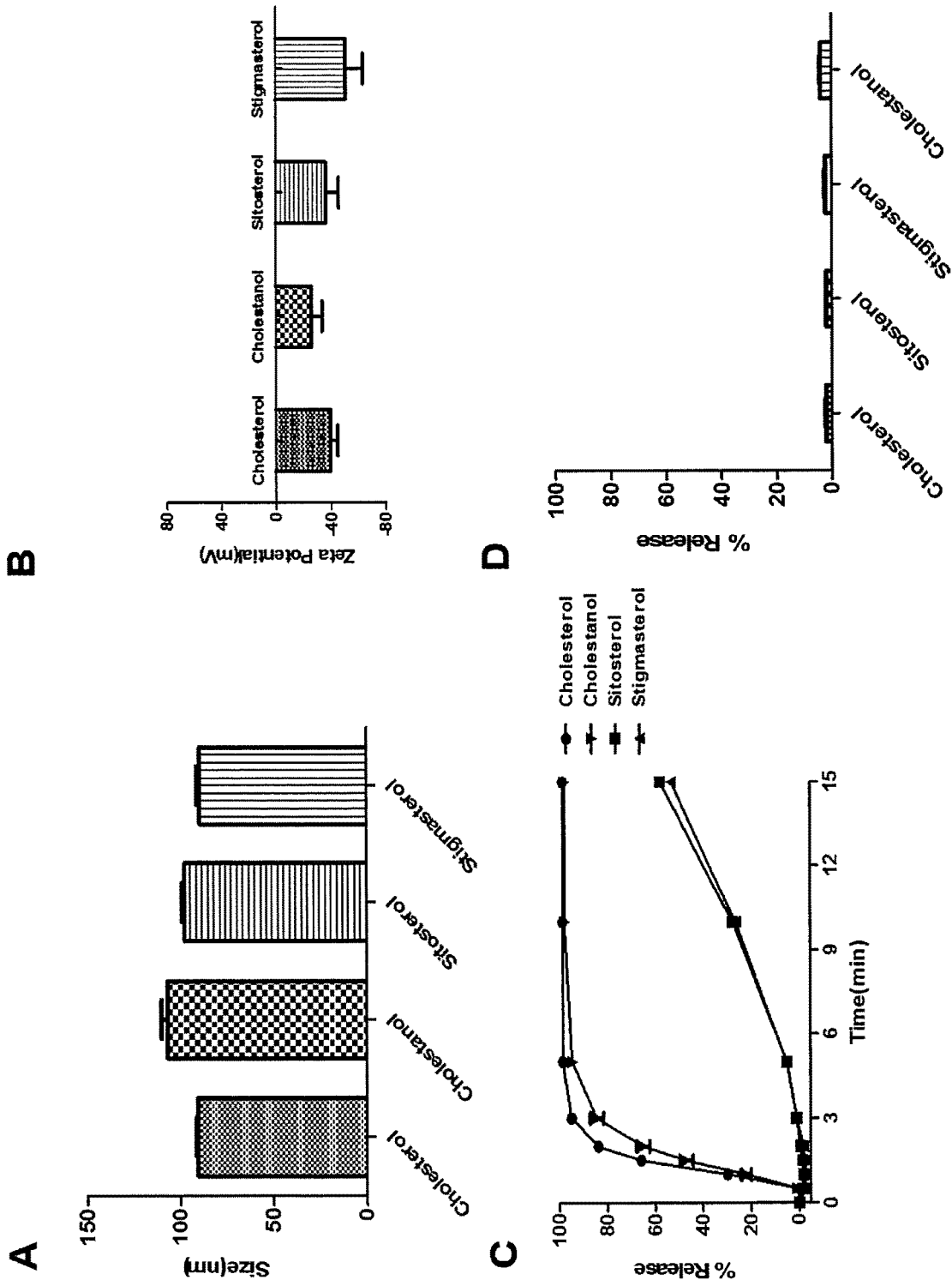
FIG. 18. Cholesterol, Cholestanol, Sitosterol and Stigmasterol can be used to form Pyro liposomes. Sizes of Pyro liposomes loaded with doxorubicin made with 40 molar % Cholesterol, beta-Cholestanol, Sitosterol or Stigmasterol were tested in PBS (A); Zeta potential of Pyro liposomes made with 40 molar % Cholesterol, beta-Cholestanol, Sitosterol or Stigmasterol were tested in distilled $H_2O$ (B); Triggered release in 50% filtered mature bovine serum of Pyro liposomes made with 40 molar % Cholesterol, beta-Cholestanol, Sitosterol or Stigmasterol (C). Stability of Pyro liposomes made with 40 molar % Cholesterol, beta-Cholestanol, Sitosterol or Stigmasterol in 50% filtered mature bovine serum at 37° C. for 4 h (D). All the formulations are made with 53 molar % DSPC, 5 molar % PEG2k, 40 molar % Cholesterol, Cholestanol, Sitosterol or Stigmasterol and 2 molar % Pyro-phospholipid, doxorubicin to lipid loading ratio 1:8.
Figure 19:
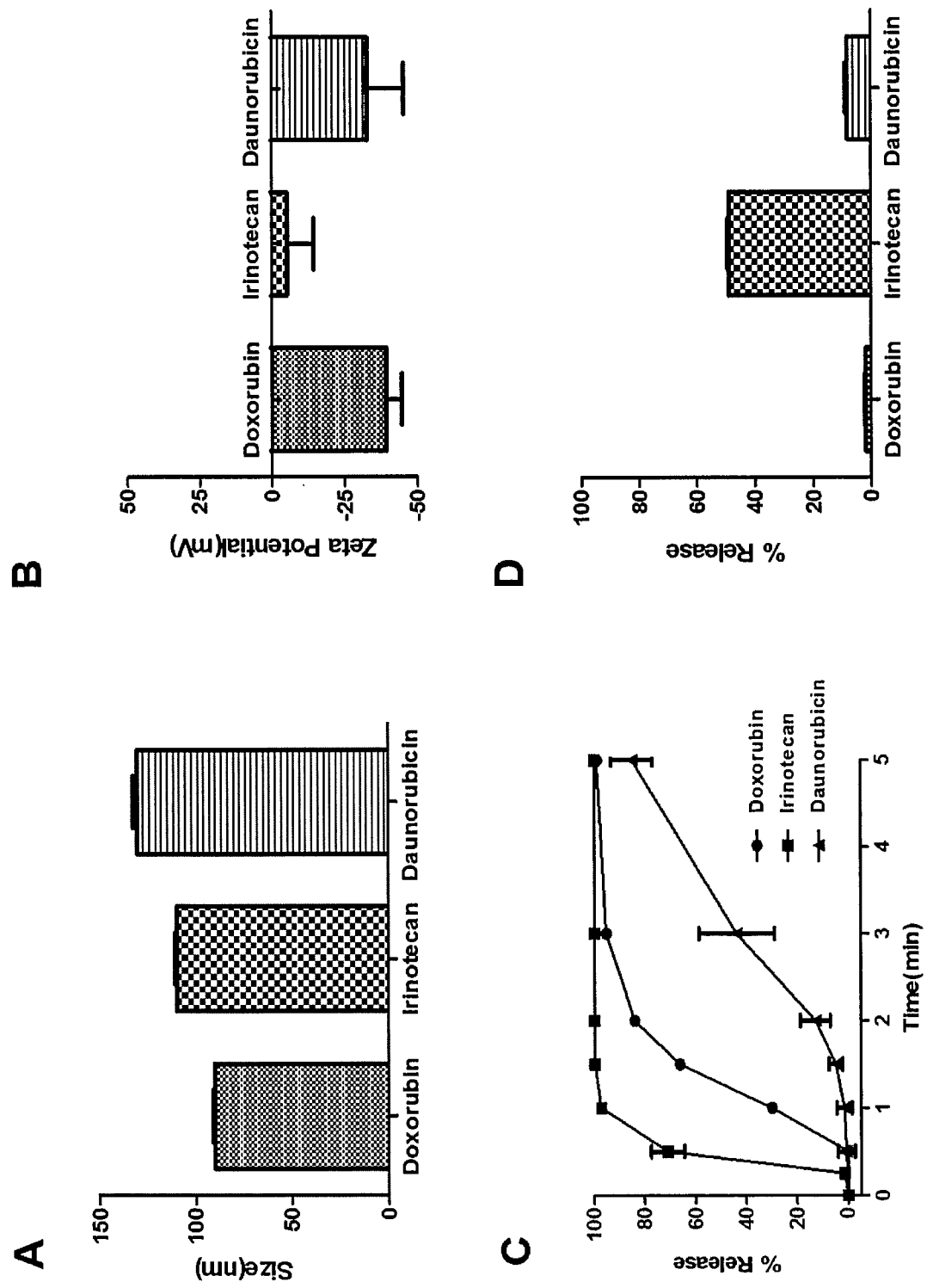
FIG. 19. Doxorubicin, irinotecan and daunorubicin can be actively loaded into Pyro liposomes and release upon laser irradiation. Sizes of Pyro liposomes loaded with doxorubicin, irinotecan or daunorubicin were tested in PBS (A); Zeta potential of Pyro liposomes loaded with doxorubicin, irinotecan and daunorubicin were tested in distilled $H_2O$ (B); Triggered release in 50% filtered mature bovine serum of Pyro liposomes loaded with loaded with doxorubicin, irinotecan or daunorubicin (C). Stability of Pyro liposomes loaded with doxorubicin, irinotecan or daunorubicin in 50% filtered mature bovine serum at 37° C. for 4 h (D). Formulations of Pyro liposomes loaded with Dox is 53 molar % DSPC, 5 molar % PEG2k, 40 molar % Cholesterol and 2 molar % Pyro-phospholipid, doxorubicin to lipid loading ratio 1:8. Formulation of Pyro liposomes loaded with irinotecan is 50 molar % Sphingomyelin, 45 molar % Cholesterol and 2 molar % Pyro-phospholipid. Formulation of Pyro liposomes loaded with daunorubicin is 43 molar % DSPC, 5 molar % PEG2k, 50 molar % Cholesterol and 2% Pyro-phospholipid. All the drug to lipid molar loading ratio is 1:8.
Figure 20:
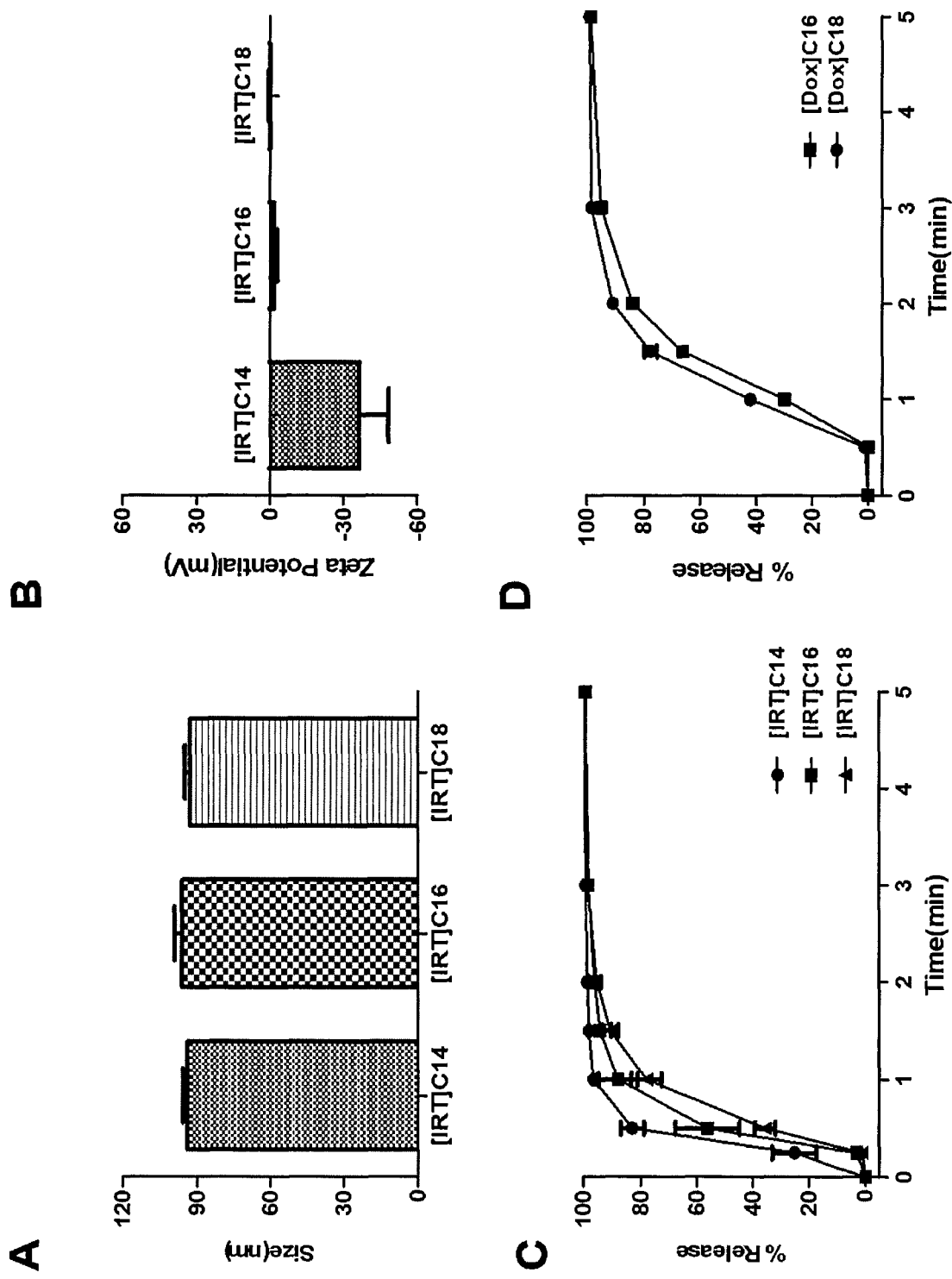
FIG. 20. Pyro lipid with variable acyl chain length can be used to form pyro liposomes. Sizes of Pyro liposomes loaded with irinotecan (IRT) made with Pyro lipid with carbon chain length 14, 16 or 18 were tested in PBS (A); Zeta Potential of Pyro liposomes made with variable carbon chain length 14, 16 or 18 were tested in distilled $H_2O$ (B); (C) Triggered release in 50% filtered mature bovine serum of Pyro liposomes made with Pyro lipid of carbon chain length 14, 16 or 18. (D) Light triggered release of Pyro liposomes made with Pyro lipid of carbon chain length 16 and 18 (Dox to lipid loading ratio 1:8) in 50% filtered mature bovine serum. All the formulations are made with 53 molar % DSPC, 5 molar % PEG2k, 40 molar % Cholesterol and 2 molar % Pyro-phospholipid, irinotecan or doxorubicin to lipid molar loading ratio 1:8.

In order to demonstrate that pyro-phospholipid induced release is applicable to a wide range of formulations, we tested doxorubicin loading and release with alternatives to DSPC including various PC lipids (FIG. 15) and other type of lipids including Phosphatidylethanolamine (PE) and Phosphatidic acid (PA) lipids (FIG. 16). FIG. 17 demonstrated another drug, irinotecan could be loaded and release with various DSPC alternatives including cationic lipids DOTAP, PA, PE, and Phosphatidylglycerol (PG) lipids. Cholesterol could also be replaced by cholesterol analogs including beta-Cholestanol, Sitosterol and Stigmasterol (FIG. 18). We additionally tested the loading, release for other drugs (irinotecan and daunorubicin). In the case of iriontecan the formulation used was PEG free consisting of Sphingomyelin, Pyro-phospholipid and cholesterol. A DSPC/PEG-lipid/pyro-phospholipid/cholesterol formulation used for daunorubicin with 50% cholesterol used (FIG. 19) as daunorubicin cannot be loaded when lower cholesterol concentrations is used. Pyro-phospholipids with a modified structure were also tested, where the lipids containing 14, 16 (normal) or 18 acyl side-chains were used for conjugation (FIG. 20). The results showed that irinotecan could be loaded and released from liposomes with 14, 16 and 18 carbon side-chains and doxorubicin could be loaded and released from liposomes with 16, 18 carbon side-chains.

Thus, PoP-liposomes as described herein form a robust system which achieved thermostable cargo retention as well as effective release upon exposure to clinically-relevant doses of NIR radiation. Release could be tuned by varying porphyrin doping, laser irradiation time and laser irradiation power. This represents a departure from externally-triggered release systems which rely on heating to a few degrees above body temperature and may have issues with stability at physiological temperatures. In response to NIR irradiation, PoP-liposomes of the present disclosure released their cargo with robust spatial and temporal control and when loaded with appropriate agents provide effective treatment and diagnostic options.

EXAMPLE 3

This example further describes the preparation of PoP-liposomes without PEG-lipid, loading, and release of cargo.

Figure 21:
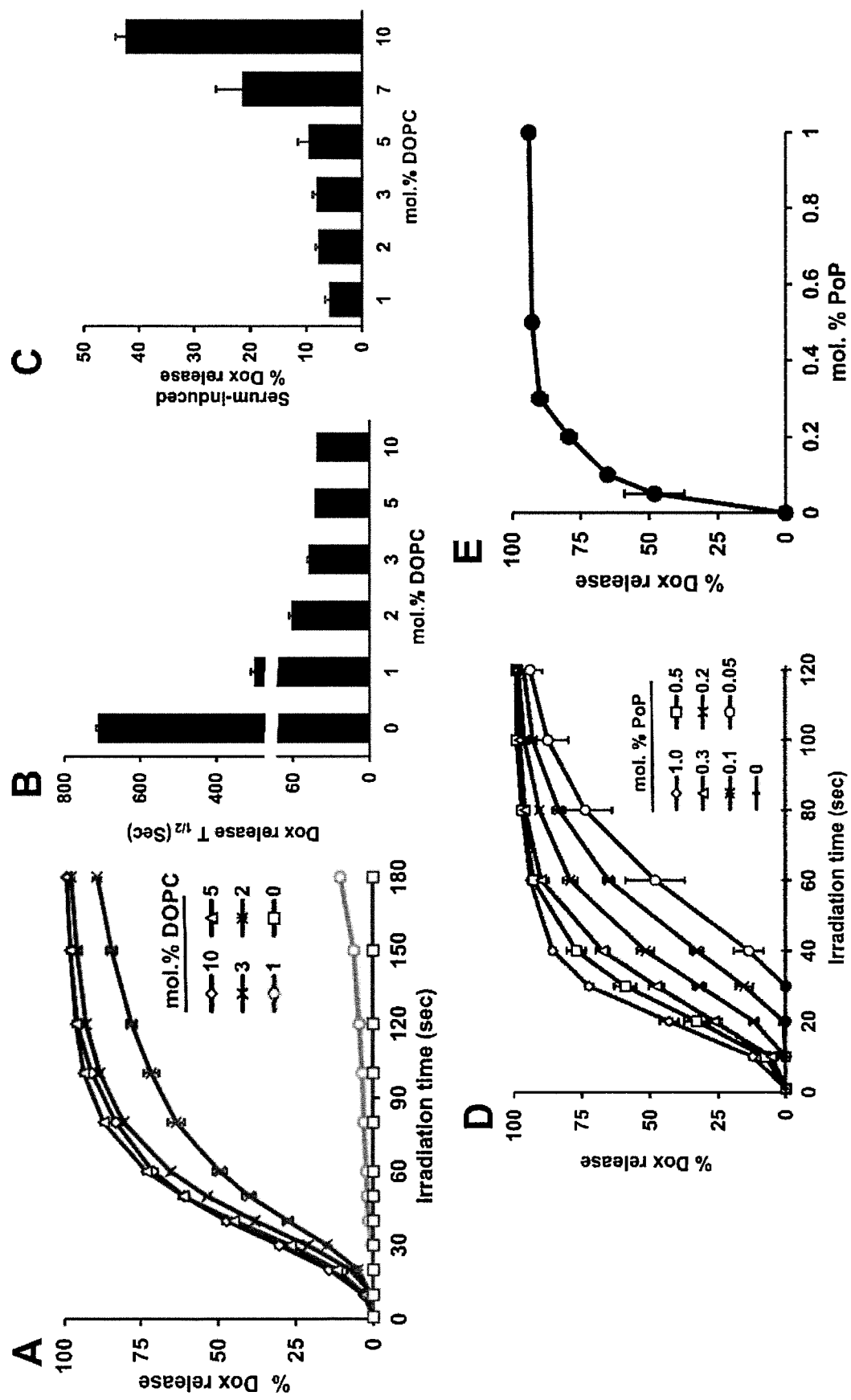
FIG. 21. Rapid light-triggered release of Dox in liposomes containing small amounts of DOPC and PoP. (A) Release of Dox from PoP liposomes (0.3 mol % PoP) with various amounts of DOPC upon irradiation at 310 mW/cm$^2$ in 50% bovine serum at 37° C. (B) Time required to reach 50% release of Dox from PoP liposomes (0.3 mol % PoP) with various amounts of DOPC. (C) Serum-induced Dox release after 4 h (h=hour(s)) incubation in 50% bovine serum at 37° C. (D) Release of Dox from PoP liposomes with various amounts of PoP (0.05-1 mol %) with laser irradiation (310 mW/cm$^2$) in 50% bovine serum at 37° C. (E) Amount of Dox released at 60 s for PoP liposomes containing varying amounts of PoP. Data are presented as mean±S.D., n=3.
Figure 27:
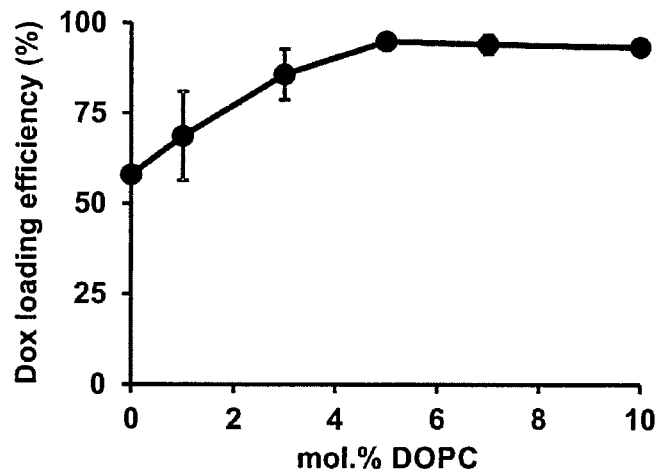
FIG. 27. DOPC assists Dox loading of PoP liposomes. DOPC assisted loading of Dox into PoP liposomes (2 mol % PoP) lacking PEG-lipid. Data are presented as mean±S.D., n=2-3.
Figure 28:
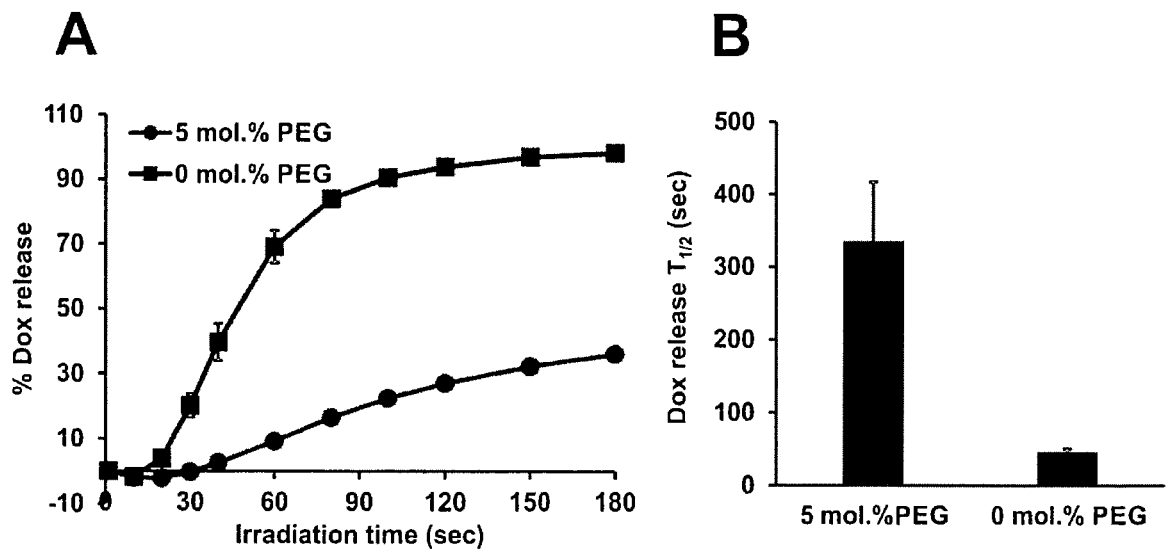
FIG. 28. PEG-lipid retards light triggered release rate from PoP liposomes containing DOPC. (A) Light triggered release profile of Dox from PoP liposomes (0.1 mol % PoP) with or without PEG. (B) Time required to reach 50% release of Dox from PoP liposomes (0.1 mol % PoP) with or without PEG-lipid. Data are presented as mean±S.D., n=3.

We elected to characterize PoP liposomes lacking PEG-lipid to see if there was an enhanced light-triggered release in PoP liposomes. Also, immunogenicity of PEG-lipid has been identified as a possible concern in patients. PoP liposomes were made with DSPC, DOPC, cholesterol, and Pyro-phospholipid (molar ratio, 59.7-x:x:40:0.3, x=mol % DOPC). DSPC was replaced with DOPC ranging from 0-10 mol % and the effects on the light-triggered release under irradiation with near infrared (NIR) 665 nm light were assessed (FIG. 21A, 21B). Inclusion of just 2 mol % DOPC accelerated light-triggered release, resulting in a 11.6 fold decrease (713 sec vs. 61 sec) in the time required to release 50% of Dox. Increasing amounts of DOPC (more than 3 mol %) further increased release rates, and liposomes with 5 mol % DOPC released 50% of loaded Dox in 43 sec. Serum stability of Dox loaded PoP liposomes with various amounts of DOPC revealed that PoP liposomes with DOPC content above 5 mol % were not stable when incubated in 50% bovine serum at 37° C. for 4 h, leading to 22% and 42% leakage of Dox at 7 mol % and 10 mol % DOPC, respectively (FIG. 21C). Thus, 5 mol % of DOPC was selected as it enabled both rapid light-triggered release and good serum stability in the absence of NIR irradiation (just ~10% Dox release in 50% bovine serum in 4 h). We previously demonstrated that the loading efficacy of Dox for liposomes containing 2 mol % Pyro-phospholipid was just ~50% without the inclusion of PEG-lipid. Interestingly, incorporation of DOPC allowed for ~95% Dox loading efficacy in PoP liposomes lacking PEG-lipid (FIG. 27). However, when the amount of pyro-phospholipid was decreased to less than 0.5 mol %, high loading efficiencies of Dox were achieved without DOPC (loading efficiency 97.3% for the formulation with 0 mol % DOPC in FIG. 21A). Inclusion of 5 mol % PEG-lipid reduced the light triggered release rate in PoP liposomes containing DOPC (336 s vs 46 s for 50% Dox release, FIG. 28).

By using a small amount of DOPC (5 mol %), rapid release of Dox was achieved using less than 1 mol % PoP (FIG. 21D). Irradiation times required to reach 50% Dox release was less than 30 s for liposomes containing 0.5-1 mol % PoP. ~90% of Dox could be released in 60 s for liposomes containing 0.3 mol % or more PoP (FIG. 21E). Increasing amount of PoP enhances light-triggered cargo release, however administration of photosensitizers to patients also increases the risk of potentially phototoxic side effects. Thus, 0.3 mol % PoP was selected for further investigation, as it offered the minimal amount of PoP used and rapidly released contents in 60 s. Unless otherwise noted, the final formulation used for subsequent studies was [DSPC:DOPC:Cholesterol:PoP], [54.7:5:40:0.3, mol %] with a drug to lipid molar ratio of 1:8.

Figure 29:
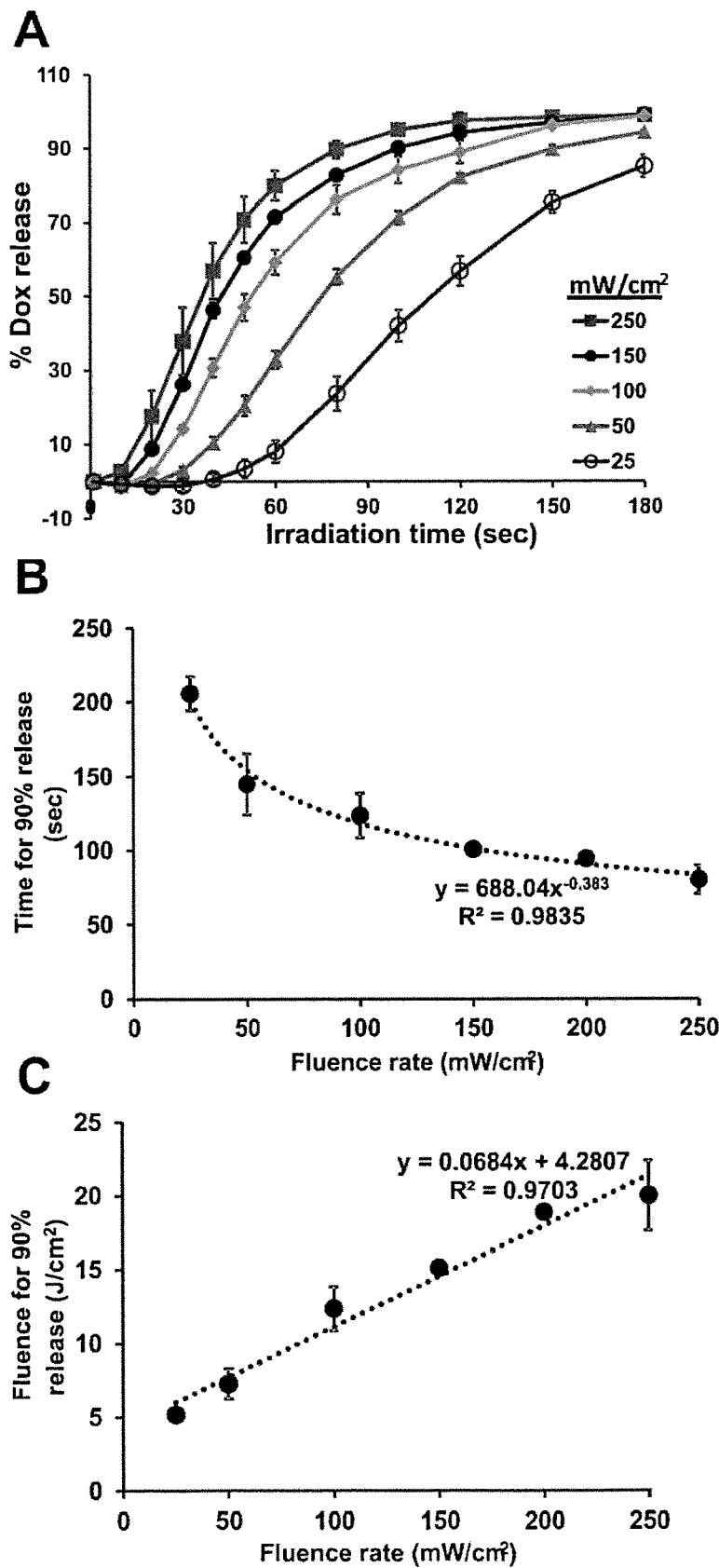
FIG. 29. Total energy required for Dox release depends on fluence rate applied. (A) Release of Dox upon irradiation at various fluence rates in 50% bovine serum. (B) Time required to reach 90% Dox release at a function of fluence rate. (C) Total fluence required to reach 90% Dox release at a function of fluence rate. Data are presented as mean±S.D., n=3.

Dox release at lower fluence rates (25 mW/cm$^2$ to 250 mW/cm$^2$) was assessed in 50% bovine serum at 37° C. (FIG. 29A). At low fluence rates (25 mW/cm$^2$), 57% Dox release was observed in 2 min of NIR irradiation. The time required to reach 90% Dox release was not linear (FIG. 29B), so that the total energy required to reach 90% release was not constant. This is in contrast to our previous observation that DOPC-free liposomes release cargo with a constant amount of energy regardless of fluence rate. The fluence required for 90% release was in a linear relationship with fluence rate, with lower total energy required at lower fluence rate (FIG. 29C). This suggests an alternative mechanism exists in PoP liposomes containing DOPC. As singlet oxygen generation is less efficient at higher fluence rates due to depletion of oxygen, we hypothesized that the release mechanism could be related to singlet oxygen generation during irradiation.

Figure 22:
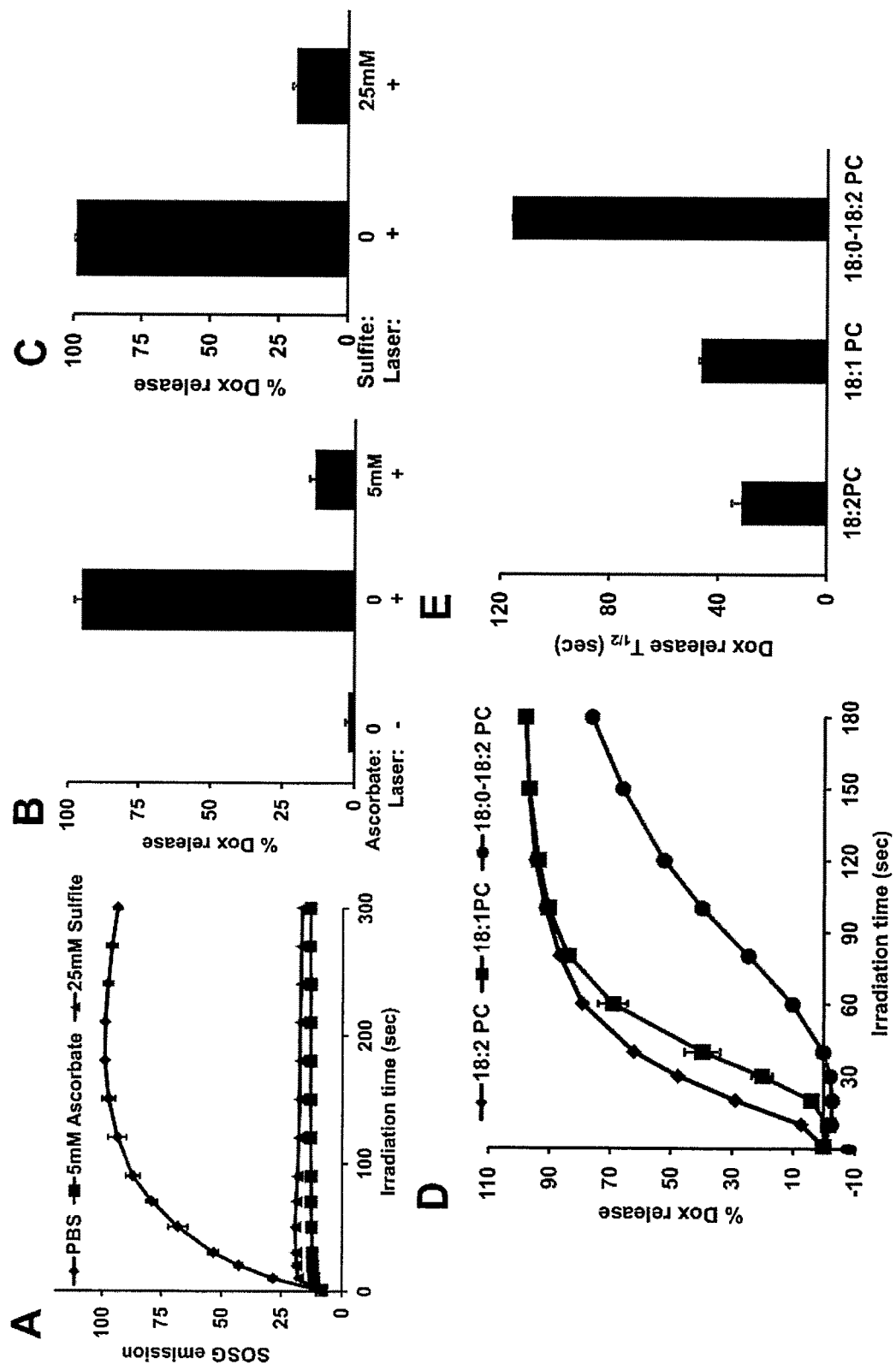
FIG. 22. Enhanced light triggered release is singlet oxygen related. (A) Singlet oxygen generation during irradiation (310 mW/cm$^2$) of PoP liposomes in PBS, PBS containing 5 mM sodium ascorbate, or 25 mM sodium sulfite. Singlet oxygen was reported by SOSG relative fluorescence unit (RFU). (B) Dox release upon irradiation (250 mW/cm$^2$ for 3 min (min=minute(s))) was inhibited in PBS containing 5 mM sodium ascorbate at room temperature. (C) Dox release upon irradiation (310 mW/cm$^2$ for 3 min) was inhibited in PBS containing 25 mM sodium sulfite at room temperature. (D) Dox release profiles of PoP liposomes (0.1% PoP, 5 mol % unsaturated lipids, 40 mol % cholesterol and 54.9 mol % DSPC) containing 18:1(cis)PC, 18:2(cis) PC, or 18:0-18:2 PC upon irradiation (310 mW/cm$^2$) in 50% bovine serum at 37° C. (E) Time required for PoP liposomes (0.1% Pyrophospholipid, 5 mol % unsaturated lipids, 40 mol % cholesterol and 54.9 mol % DSPC) to reach 50% Dox release. Data are presented as mean±S.D., n=3.

Enhanced light triggered release is singlet oxygen related. Upon light irradiation in the presence of oxygen, photosensitizers (PoP in this case) can generate reactive single oxygen. Cellular membranes are known to be a target of singlet oxygen in photodynamic therapy. It was hypothesized that the rapid light-triggered release observed was related to singlet oxygen generation. To test this, the reporter fluorophore singlet oxygen sensor green (SOSG) was used to detect the presence of singlet oxygen during liposome irradiation. The antioxidant sodium ascorbate and the molecular oxygen scavenger sodium sulfite were used to inhibit singlet oxygen generation. Under NIR irradiation, singlet oxygen was generated by the PoP liposomes, but this was inhibited by ascorbate and sulfite (FIG. 22A). Dox release from PoP liposomes was inhibited in the presence of 5 mM ascorbate (FIG. 22B). No Dox release was observed in the absence of light treatment, with or without sodium ascorbate. Light treatment of Dox-loaded PoP liposomes induced 95% Dox release in 3 min, but inclusion of 5 mM sodium ascorbate led to an 81% reduction in Dox release. Similarly, light-triggered Dox release in the presence of 25 mM sodium sulfite was reduced by 80% (FIG. 22C).

Figure 30:
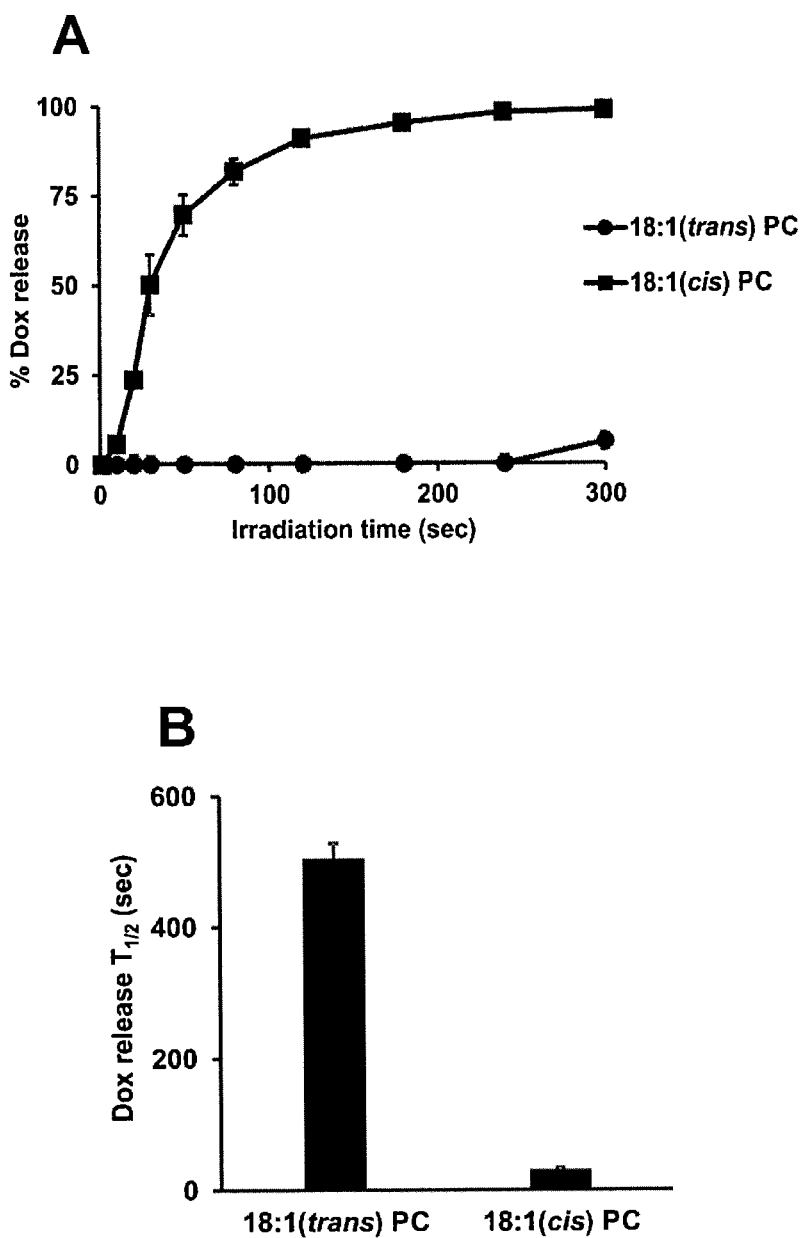
FIG. 30. The cis configuration of DOPC is required for enhancement of light release. (A) Dox release profiles of PoP liposomes (0.3 mol % PoP, 5 mol % 18:1 (trans) PC or 18:1(cis) PC) during irradiation (310 mW/cm²) in 50% bovine serum at 37° C. (B) Time required to reach 50% release of Dox from PoP liposomes (0.3 mol % PoP) containing 18:1 (trans) PC or 18:1(cis) PC. Data are presented as mean±S.D., n=3.

The light-triggered release of Dox-loaded PoP liposomes containing different unsaturated phospholipids was examined, including 18:1(cis) PC (DOPC), 18:2 (cis) PC, and 18:0-18:2 PC (FIG. 22D). Other unsaturated phospholipids also enhanced Dox release from PoP liposomes upon irradiation. Lipids with greater degree of unsaturation induced faster release (FIG. 22E). Under NIR light, 18:2(cis) PC (4 unsaturated bonds) liposomes released 50% of Dox in 31 sec, while that time increased to 46 sec for liposomes containing 18:1(cis) PC (2 unsaturated bonds). Although 18:2 (cis) PC resulted in faster release compared to 18:1 (cis) PC, PoP liposomes containing 18:2 (cis) PC demonstrated a lower loading efficiency (75% loading efficiency, Table 2). Interestingly, 18:0-18:2 PC has the same unsaturation extent as 18:1(cis) PC, however, the light-triggered release rate was slower, achieving 50% Dox release in 116 sec. This might be due to a lower probability of singlet oxygen accessing the unsaturated bonds of 18:0-18:2 PC that are on the same chain. Further studies demonstrated that the chemical configuration of the unsaturated lipid was critical, as 18:1(trans) PC did not show obvious enhancement in light triggered release (FIG. 30A). Irradiation for 505 sec was required to reach 50% Dox release in 18:1(trans) PC, compared to 31 sec for 18:1(cis) PC (FIG. 30B). Local defects or destabilization may occur during this process and ultimately assist in the disruption of the lipid bilayers by 18:1 (cis) PC but not 18:1(trans) PC.

TABLE 2

Characterization of PoP liposomes containing unsaturated lipids

| Unsaturated lipids | Size (nm) | PDI | Loading efficiency (%) |
|---|---|---|---|
| 18:0-18:2 (cis) PC | 114.3 ± 1.6 | 0.04 ± 0.02 | 98.2 ± 0.85 |
| 18:2 (cis) PC | 108.2 ± 0.05 | 0.07 ± 0.02 | 75.3 ± 2.5 |
| 18:1 (trans) PC | 114.35 ± 3.5 | 0.06 ± 0.0.02 | 96.2 ± 0.56 |

Data show mean ± S.D., n = 3

Figure 23:
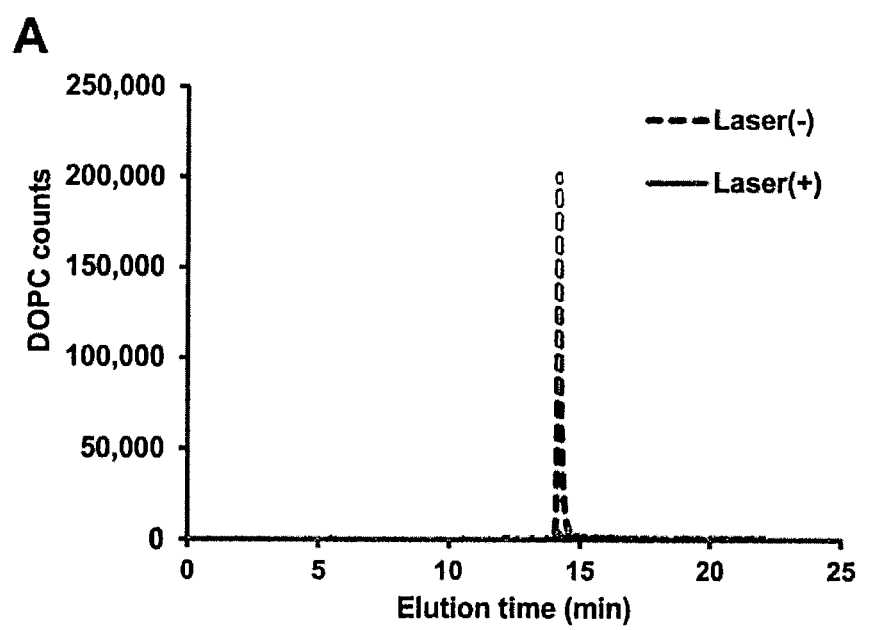
FIG. 23. Light irradiation of PoP liposomes results in oxidization of DOPC. (A) DOPC content in PoP liposomes before and after irradiation for 4 min at 310 mW/cm$^2$. (B) New lipid species generated after irradiation (m/z: 850.5806). (C) DOPC oxidation kinetics (% DOPC present compared to non-irradiated samples) while irradiated at 310 mW/cm$^2$. Data are presented as mean±S.D., n=3. (D) Structure of DOPC and possible structure of oxidized DOPC product (Exact mass 850.5804, matching the detected oxidized species with m/z: 850.5806). (E) Schematic of DOPC oxidation in PoP liposomes by singlet oxygen leading to release of Dox.
Figure 23:
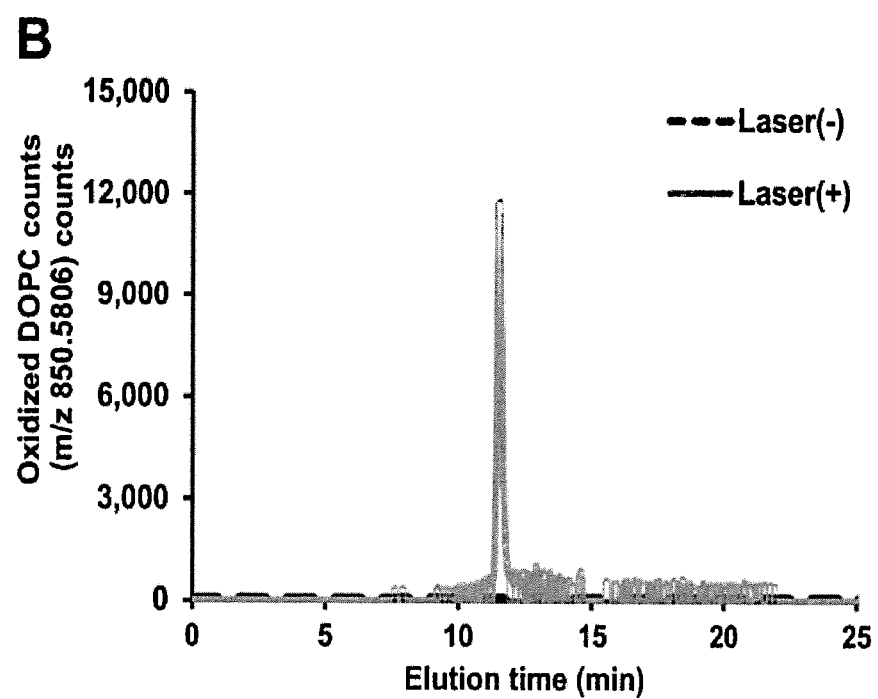
Figure 23:
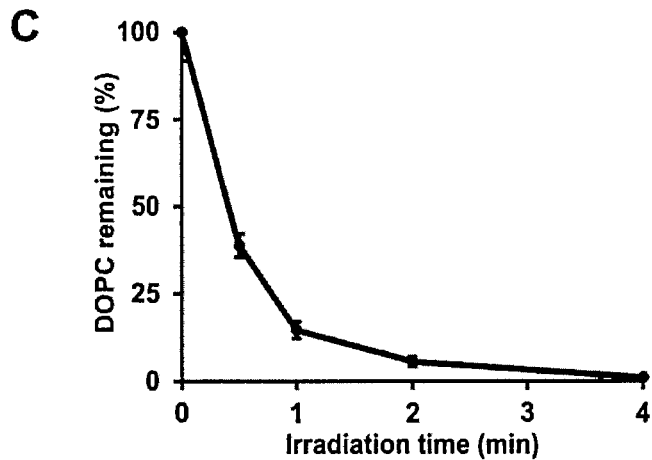
Figure 23:
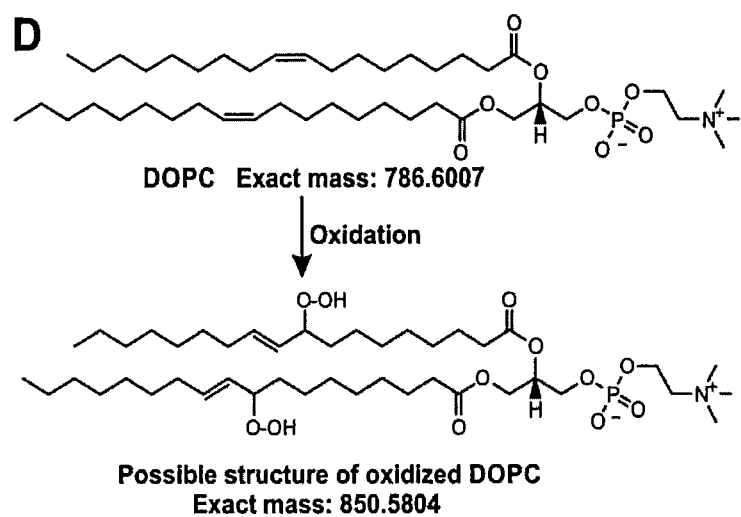
Figure 23:
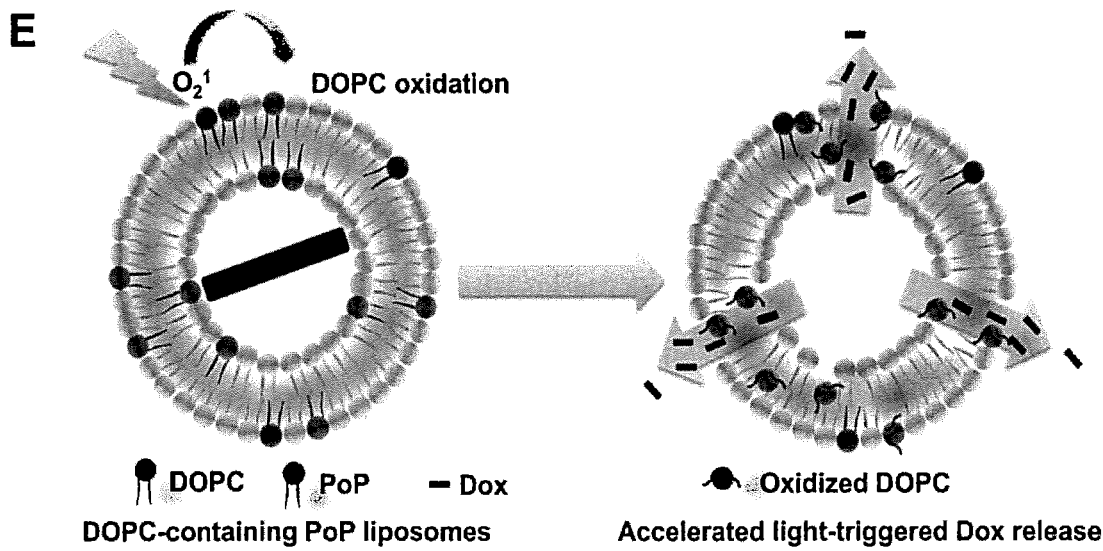
Figure 31:
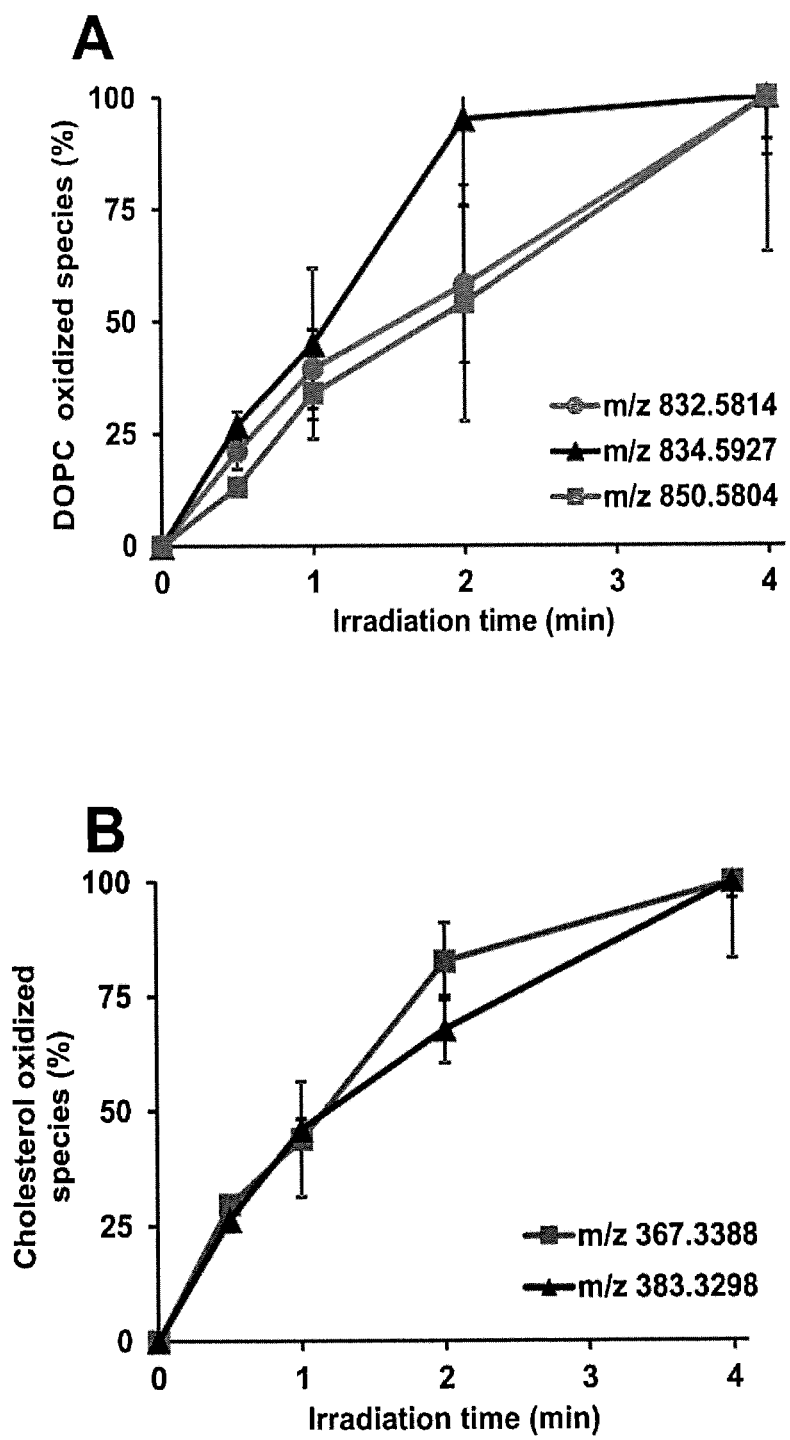
FIG. 31. Generation of new species upon irradiation. (A) DOPC related oxidized species generated over time while irradiation (310 mW/cm²). Highest signals (4 min irradiation) were normalized as 100%. (B) Cholesterol-related oxidized species generated over time during irradiation (310 mW/cm²). Highest signals (4 min irradiation) were normalized as 100%. Data are presented as mean±S.D., n=3.

Oxidization of DOPC during light-triggered release. Singlet oxygen can cause oxidation of unsaturated phospholipids and cholesterol. The DOPC content of the PoP liposomes before and after NIR irradiation (310 mW/cm$^2$ for 4 min) was assessed by liquid chromatography and mass spectrometry (LC-MS). 96% of DOPC was eliminated following irradiation (FIG. 23A) and three DOPC-related oxidized species (m/z: 832.5814, 834.5927 and 850.5806; phospho-lipid head groups confirmed, FIG. 23B and FIG. 31A) were identified. In addition to these DOPC-related species, 2 cholesterol-related oxidized species (m/z: 367.3388, 383.3298, FIG. 31B) were also identified. DOPC oxidization kinetics under NIR irradiation showed that 85% of DOPC was oxidized after 1 min, a time point that at which ~90% of loaded Dox was released (FIG. 23C). DOPC was further oxidized with prolonged NIR irradiation, with 99% of the DOPC oxidized after 4 min. The amount of DSPC remained constant throughout the course of irradiation (data not shown). A possible lipid structure with 9-hydroperoxides matching the correct mass of the observed DOPC oxidized species (m/z 850.5806) is presented in FIG. 23D. Singlet oxygen reacts with carbon at either end of a double bound by concerted addition (or "ene" reaction) and produces an allylic hydroperoxide in the trans configuration. It is likely that both side chains of DOPC were oxidized, forming a mixture of 9- and 10-hydroperoxides. Lipid hydroperoxides are not stable species and prone to secondary oxidization. There was a relatively high variation of DOPC oxidized species detected (FIG. 25A), while cholesterol oxidized species (FIG. 31B) were relatively consistent.

Figure 32:
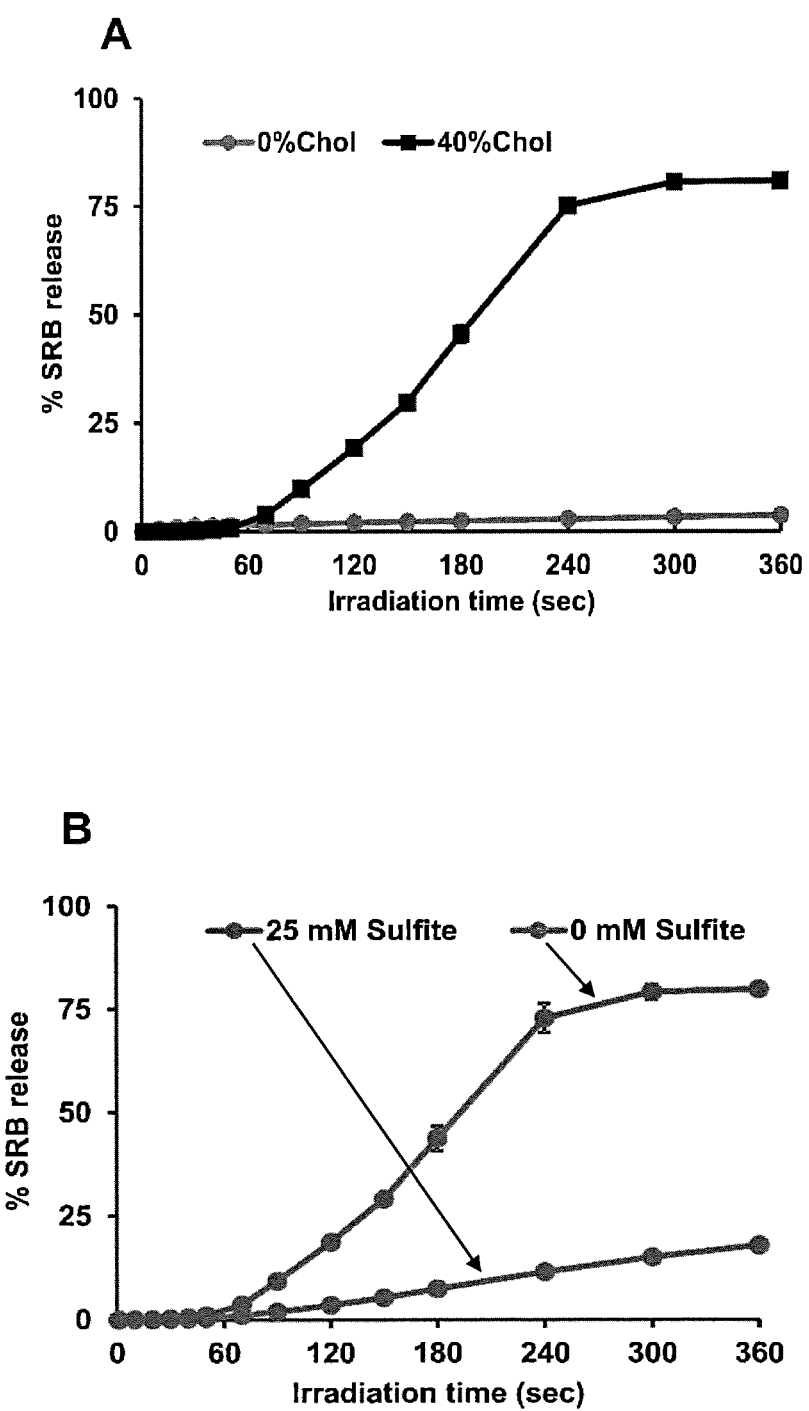
FIG. 32. Oxidization of cholesterol leads to cargo release of DOPC-free PoP liposomes. (A) Liposomes contained 5 mol % PEG-lipid, 5 mol % PoP, 0% or 40% Cholesterol, and 90 mol % or 50 mol % DSPC, respectively. Light-triggered release of sulforhodamine (SRB) loaded PoP liposome was performed at 250 mW/cm² in PBS at room temperature. (B) Sulfite inhibition of permeabilization. Liposomes contained of 5 mol % PEG-lipid, 5 mol % PoP, 40% Cholesterol, and 50 mol % DSPC. Light triggered release was performed at 250 mW/cm² in PBS or PBS containing 25 mM sodium sulfite at room temperature.

The formation of allylic hydroperoxides can lead to a decrease in hydrophobic interactions that maintain liposome integrity, and likely caused acceleration of leakage and release of Dox (FIG. 23E). Further studies revealed that in the case of DOPC-free liposomes, the ability of PoP liposomes to release cargo upon NIR irradiation was dependent on oxidization of cholesterol. PoP liposomes lacking both cholesterol and DOPC could not effectively release encapsulated dyes (FIG. 32A), but inclusion of cholesterol enabled light triggered release. The oxygen scavenger sodium sulfite inhibited light-induced dye release (FIG. 32B).

Figure 24:
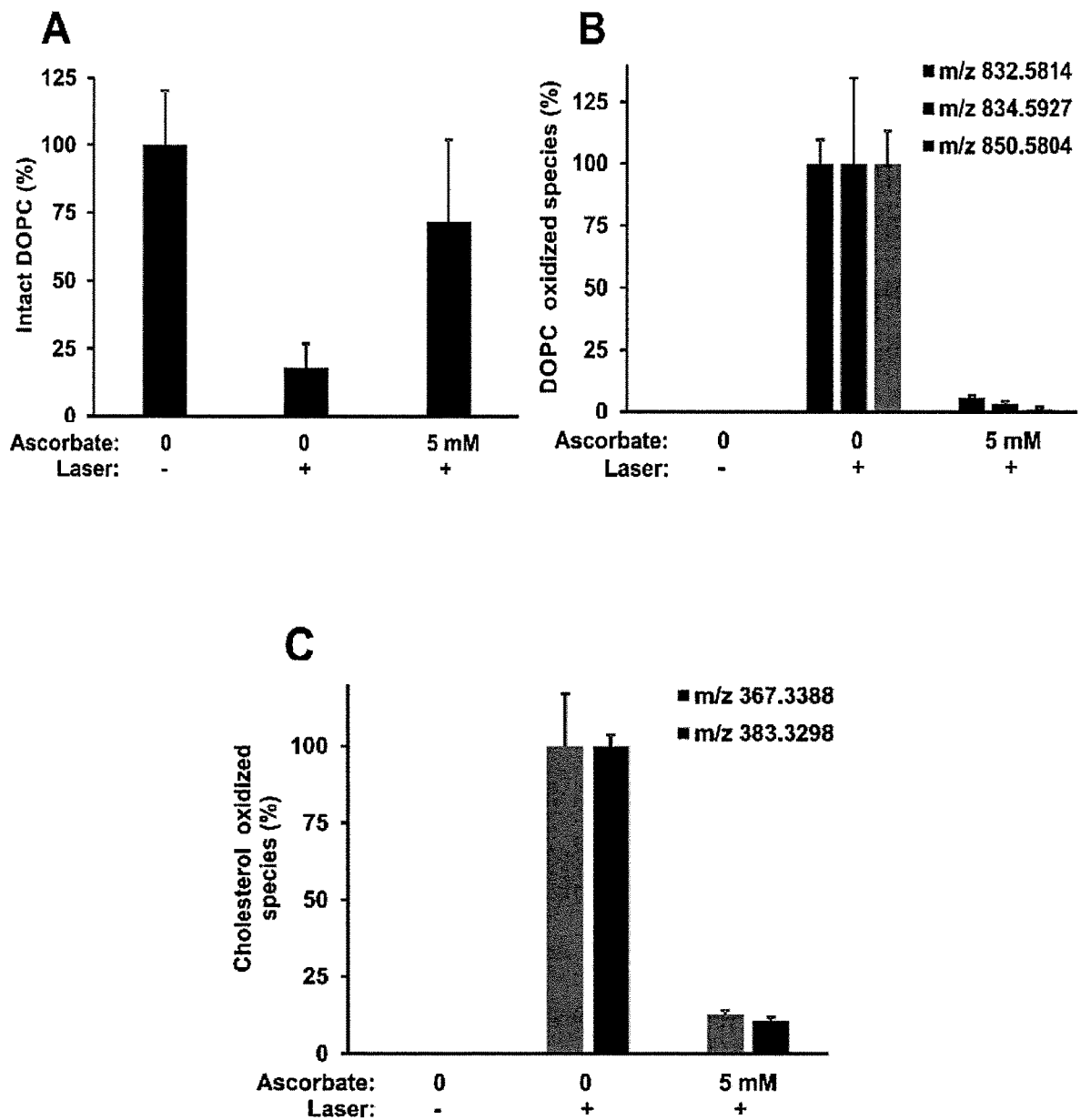
FIG. 24. Ascorbate inhibits light-triggered lipid oxidation. PoP liposomes were irradiated with a 665 nm laser diode for 4 min at 310 mW/cm² in the presence or absence of 5 mM sodium ascorbate. Signals in—laser without sodium ascorbate were normalized as 100%. (A) DOPC oxidization by light treatment was inhibited by sodium ascorbate. Sodium ascorbate inhibited generation of DOPC-related (B) and cholesterol-related (C) oxidized species upon irradiation. Data are presented as mean±S.D., n=3-6.

Lipid oxidization upon NIR irradiation was inhibited by sodium ascorbate (an anti-oxidant shown to inhibit light-triggered release in FIG. 22B), as monitored by LC-MS. In the absence of the anti-oxidant, only 18% of the intact DOPC remained following irradiation. NIR-triggered loss of DOPC was inhibited in the presence of ascorbate, with 72% of the DOPC remaining following irradiation (FIG. 24A). In the presence of sodium ascorbate, DOPC-related oxidized species were reduced to 5% compared to no sodium ascorbate samples (FIG. 24B). Generation of cholesterol-related oxidized species also decreased to just ~10% in the presence of ascorbate (FIG. 24C). Taken together with the dependence of DOPC to enhance light-triggered release, these results suggest that DOPC oxidization by singlet oxygen was responsible for the enhancement of Dox release upon NIR irradiation.

Figure 25:
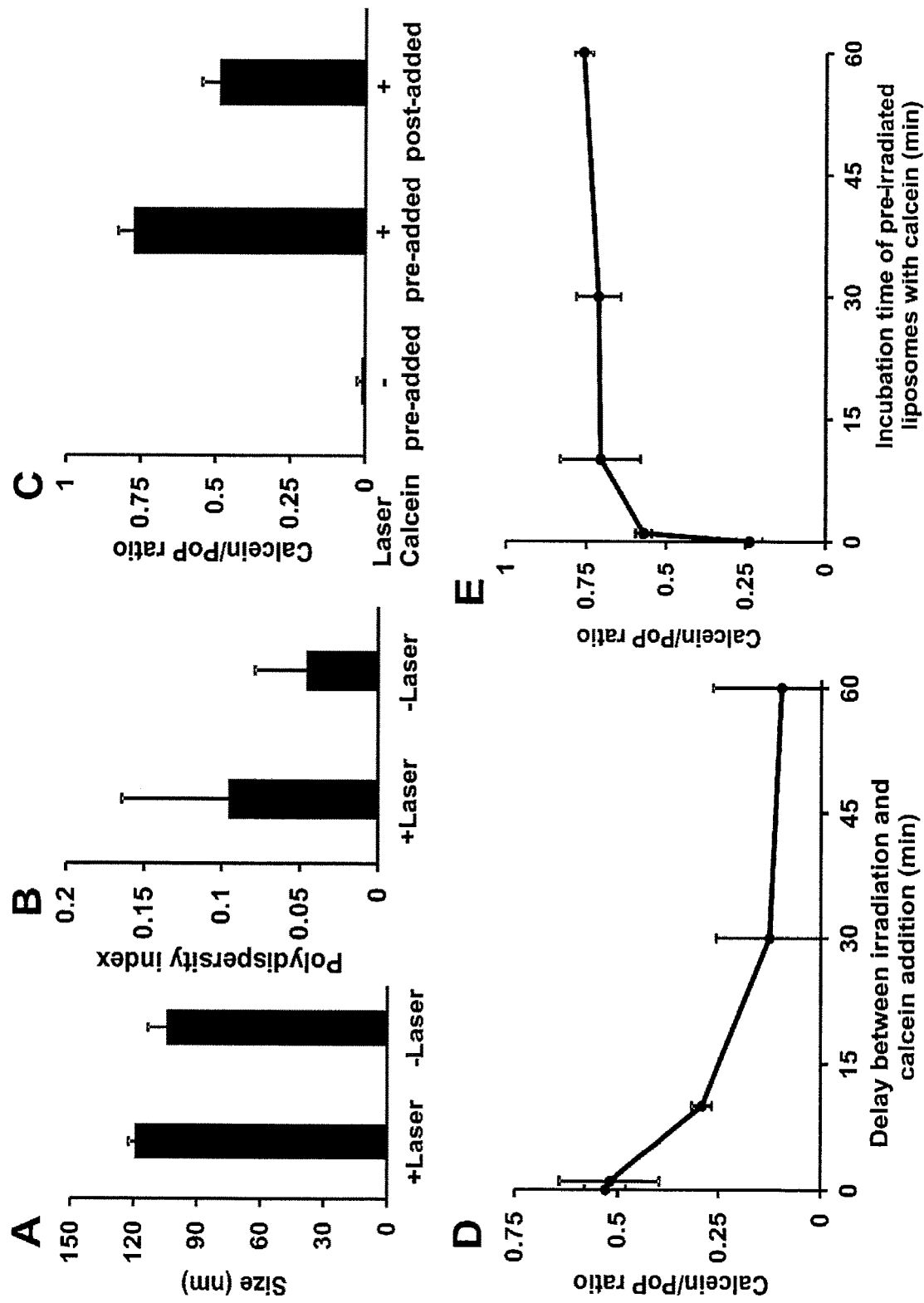
FIG. 25. Transient permeabilization of PoP liposomes containing DOPC upon NIR irradiaition. (A) Size of PoP liposomes with or without laser irradiaiton (250 mW/cm² for 3 min), measured in PBS. (B) Polydispersity index (PDI) of PoP liposomes with or without laser irradiaition (250 mW/cm² for 3 min), measured in PBS. PDI was slightly increased but not significant (one tailed t test). (C) Passive loading of calcein (presented as calcein/PoP emission ratio) with calcein addition prior or after irradiation (250 mW/cm² for 3 min). (D) Passive loading of calcein into empty pre-irradiated PoP liposomes (250 mW/cm² for 3 min). Calcein was added at indicated times following irradiation and incubation at room temperature. (E) Passive loading of calcein into pre-irradiated empty PoP liposomes (250 mW/cm² for 3 min). Calcein was added to empty PoP liposomes immediately after irradiation and incubated for various amounts of time at room temperature. Data are presented as mean±S.D., n=3.
Figure 33:
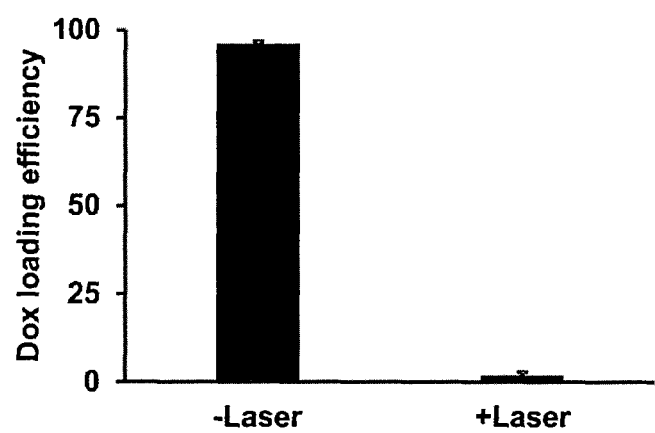
FIG. 33. Inefficient loading of Dox in pre-irradiated PoP liposomes. Pre-irradiation empty PoP liposomes (2 mg/ml lipids) was performed at 310 mW/cm² for 4 min in 250 mM ammonium sulfate solution. Pre-irradiated PoP liposomes were kept at room temperature for 30 min, followed by dialysis to remove free ammonium sulfate. Dox loading was at 1:8 drug to lipid loading ratio. Data are presented as mean±S.D., n=3.

Transient permeabilization of PoP liposomes upon NIR irradiation. We previously reported that PoP liposome membranes are only temporarily permeabilized, based on the observation that with exposure to NIR light, external calcein can be loaded into the core of the liposomes. However, for DOPC-containing PoP liposomes, the unsaturated lipid component is irreversibly oxidized, so the permanence of membrane permeabilization was of interest. Size and polydispersity index (PDI) were recorded before and after irradiation (FIGS. 25A and 25B). Liposome size increased with statistical significance (105 nm vs 119 nm, P<0.05) following light treatment, although this can be considered a modest change in liposome diameter. PDI increased but the change was not statistically significant (0.046 vs 0.096). Thus, the physical size changes that occurred in the liposomes during irradiation were subtle. Water soluble dyes such as calcein could passively load into empty PoP liposomes under NIR irradiation. This is reflected by the calcein:PoP fluorescence ratio of 0.77 in the liposome-containing fractions following removal of the free dye by gel filtration chromatography (FIG. 25C). In these conditions, non-irradiated liposomes had a calcein:PoP flurescence ratio close to 0. Interestingly, when calcein was added to empty PoP liposomes after NIR irradiation (as opposed to prior to, which is how the assay was usually performed), calcein became encapsulated in pre-irradiated empty PoP liposomes (calcin/PoP ratio 0.49). This suggests that irradiated DOPC-containing PoP liposomes did not re-seal themselves immediately after irradiation and transient membrane permeabilization was persistent. To investigate whether the pre-irradiated liposomes resealed themselves at all, calcein was added to pre-irradiated empty DOPC-containing PoP liposomes at different time points following irradiation. As shown in FIG. 25D, the amount of calcein encapsulated decreased over time, with the calcein:PoP fluorescence ratio decreasing from when the calcein was immediately added after NIR irradiation by 45% at 10 min post irradiation and by 82% at 60 min post irradiation. Thus, pre-irradiated PoP liposomes appeared to gradually reseal themselves over time, preventing calcein from being encapsulated. This was further verified in another experiment in which calcein was added to empty PoP liposomes immediately after irradiation and then incubated for 0, 1, 10, 30 and 60 min at room temperature. Prolonged incubation of pre-irradiated empty PoP liposomes in the presence of calcein led to enhanced calcein encapsulation (FIG. 25E). Most of the light-triggered loading occurred in the earlier time points with little further increase after 30 min, suggesting the membrane re-organization and re-sealing occurred in approximately 10 min. Since irradiated liposomes reformed membrane structures that were sufficiently intact to retain calcein over a gel filtration column, we investigated whether pre-irradiated liposomes could actively load Dox. Active loading of Dox was inefficient (~2% Dox loaded) for empty PoP liposomes pre-irradiated with NIR in ammonium sulfate (FIG. 33), suggesting PoP liposomes with oxidized DOPC and cholesterol were not stable enough to maintain an internal ammonium sulfate gradient (during dialysis) that is required for active Dox loading.

Figure 26:
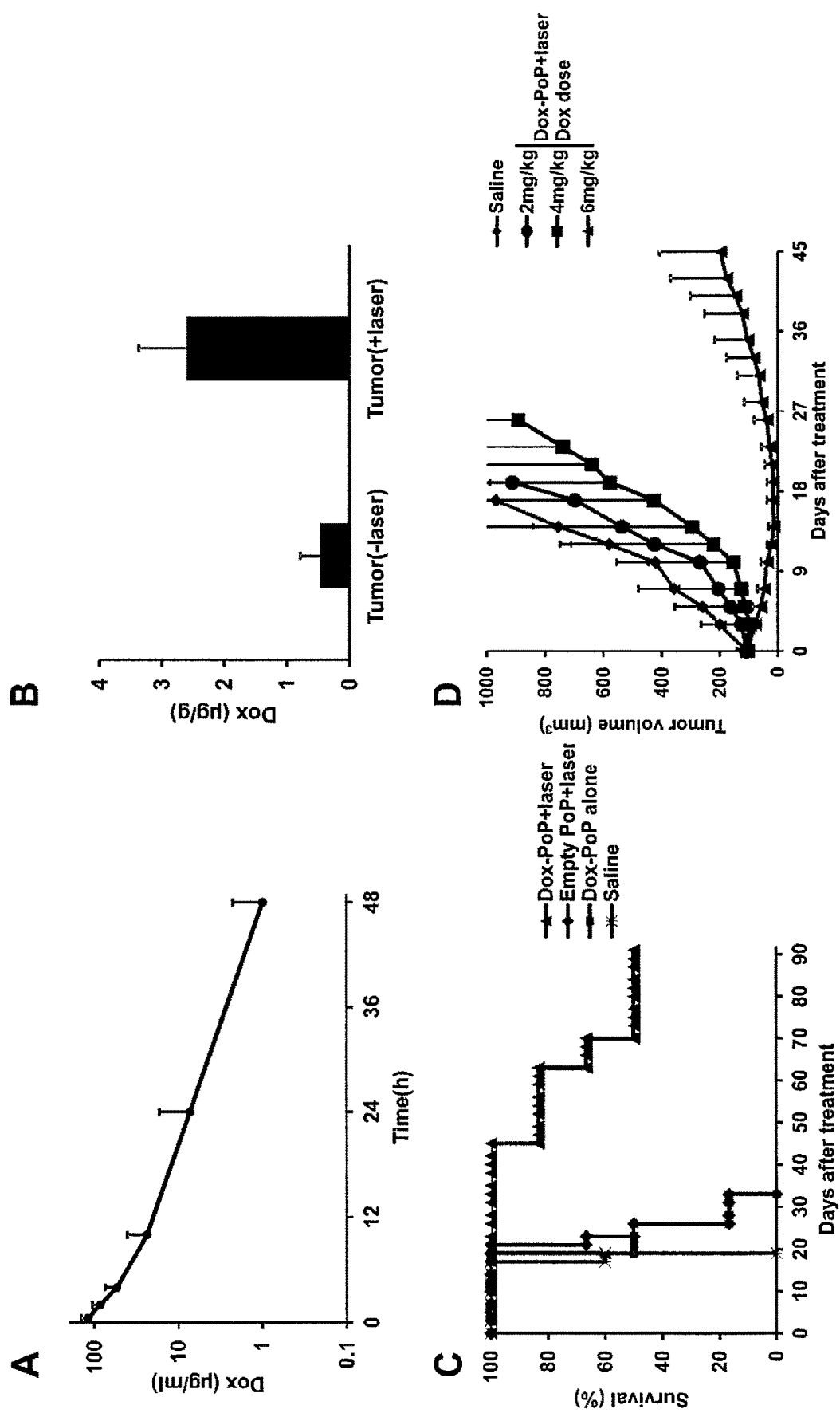
FIG. 26. In vivo evaluation of Dox-loaded DOPC-containing PoP liposomes. (A) Pharmacokinetics of Dox in serum after intravenous injection of DOPC-containing Dox-PoP liposomes (10 mg/kg Dox). Data show mean+S.D., n=4. (B) Tumoral uptake of Dox immediately after intravenous administration and phototreatment with Dox-PoP liposomes (6 mg/kg Dox) with or without laser irradiation (250 mW/cm² for 40 min). A dual tumor model was used, with a tumor on one flank irradiated and the other non-irradiated as—laser control. The irradiated tumors had statistically significant more Dox uptake based on the unpaired t test (***P<0.001). Data are presented as mean±S.D., n=4. (C) Kaplan-Merier survival cures of nude mice bearing Mia Paca-2 xenografts. Mice were intravenously administered Dox-PoP liposomes (6 mg/kg Dox, 0.25 mg/kg PoP), empty-PoP liposomes (0.25 mg/kg PoP) or saline. 10 min following injection, mice were with light irradiation (250 mW/cm² for 40 min, 600 J/cm²) as indicated. Mice were sacrificed when tumors reached 10 times initial volume. (D) Tumor volumes of nude mice bearing Mia Paca-2 xenografts. Mice were intravenously injected with Dox-PoP liposomes at 2, 4, or 6 mg/kg Dox or saline. 10 min following injection, tumors were irradiated for 40 min at 250 mW/cm². Data are presented as mean+S.D., n=5-6.
Figure 34:
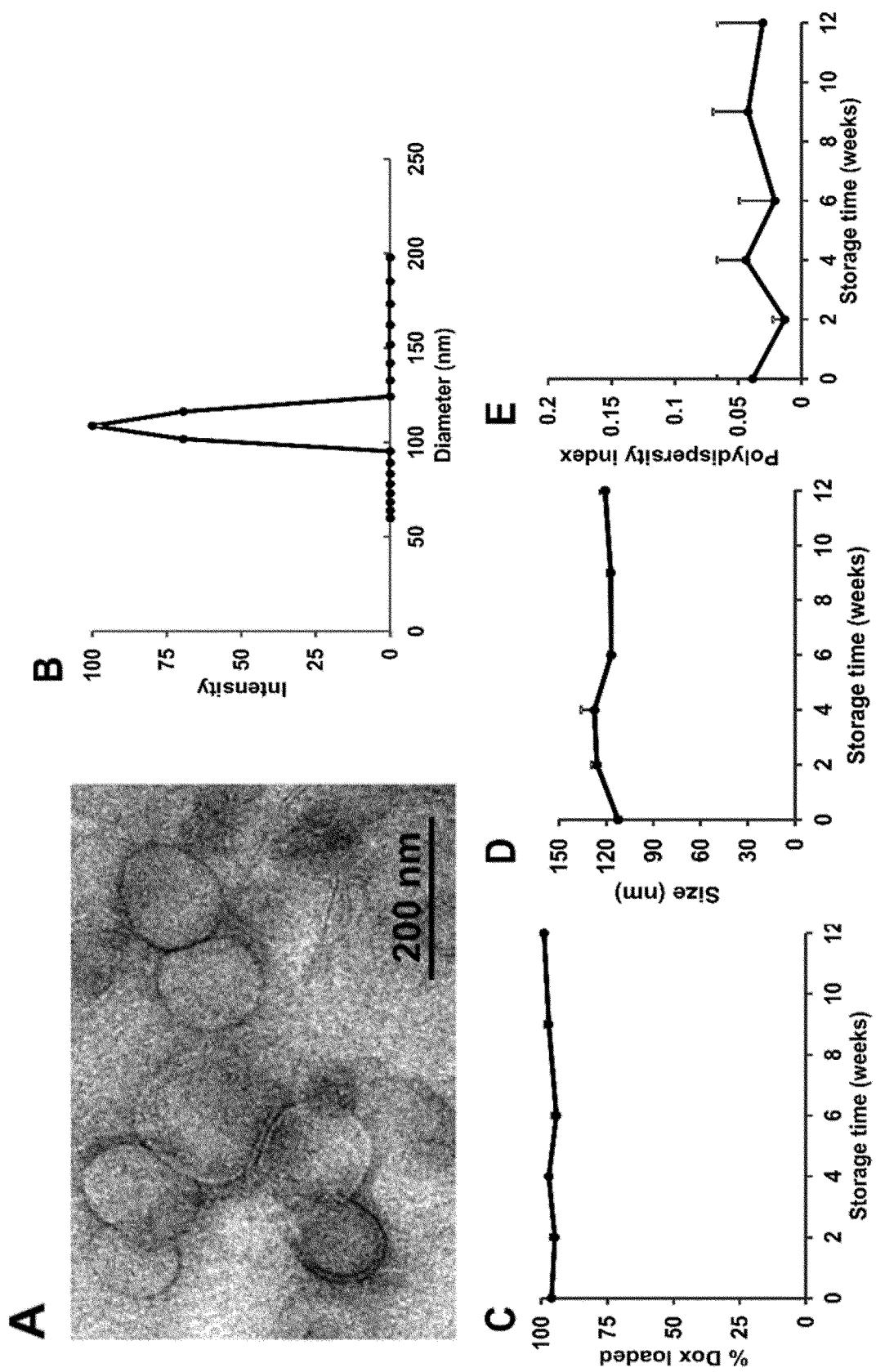
FIG. 34. Physical characterization and stability of Dox-loaded, DOPC-containing PoP liposomes. (A) Negative staining TEM image of Dox loaded liposomes. A 200 nm scale bar is shown. (B) Size distribution of Dox-loaded liposomes, tested in PBS. (C) % Dox retention inside PoP liposomes (0.3 mol % PoP) for 3 months stored at 4° C. (D) Sizes of Dox loaded PoP liposomes over 3 months, tested in PBS. (E) Polydispersity index (PDI) of Dox loaded PoP liposomes in 3 months, tested in PBS. Data are presented as mean+S.D., 3 batches of independently prepared liposomes.

In vivo evaluation. Dox-loaded, DOPC-containing PoP liposomes prepared were ~120 nm and spherical in shape (FIGS. 34A and 34B). Liposomes were stable in storage at 4° C. (protected from light exposure) for at least 3 months. No discernable drug leakage, changes of sizes or polydispersity index were observed (FIGS. 34C, 34D and 34E). For pharmacokinetic studies, liposomes were intravenously injected into CD-1 mice at a Dox dose of 10 mg/kg (FIG. 26A). A circulating half-life of 8.3 hours was observed for this PEG free formulation ([DSPC:DOPC:Chol:PoP] molar ratio of [54.7:5:40:0.3]), which was shorter than the 21.9 hour half-life of a PEGylated stealth PoP-liposome formulation ([DSPC:PEG-lipid:Chol:PoP] molar ratio of [53:5:40:2]) we recently reported [6]. With the same injection dose, non-PEGylated PoP liposomes exhibited only half the Dox peak serum concentration (119 vs 250 µg/ml) 0.5 h after injection, one third the median residence time (MRT, 9.6 vs 29.3 h), and 18% the area under the curve (AUC, 851 vs 4837 µg·h/ml) compared PEGylated stealth PoP liposomes. The clearance rate of PEG free PoP liposomes was 6 times faster (0.012 vs 0.002 ml/h/g) and the volume of distribution at steady state was 18.8 times larger to that of PEGylated PoP liposomes.

Figure 35:
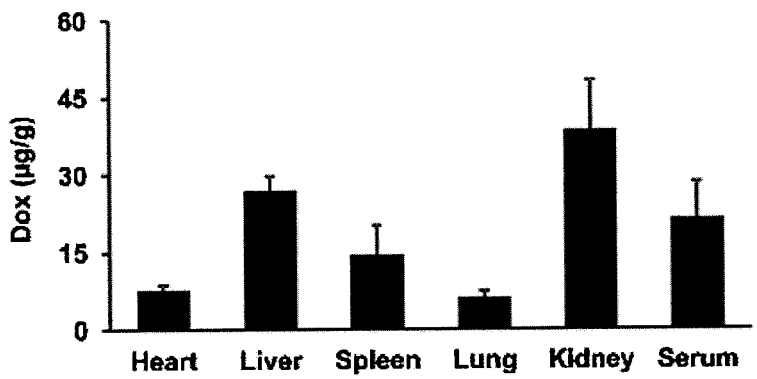
FIG. 35. In vivo parameters following phototreatment. (A) Biodistribution of Dox loaded PoP liposomes immediately after laser treatment. Body mass of mice (B) from FIG. 26A and (C) FIG. 26B in 4 weeks. Data are presented as mean±S.D., n=5-6.
Figure 35:
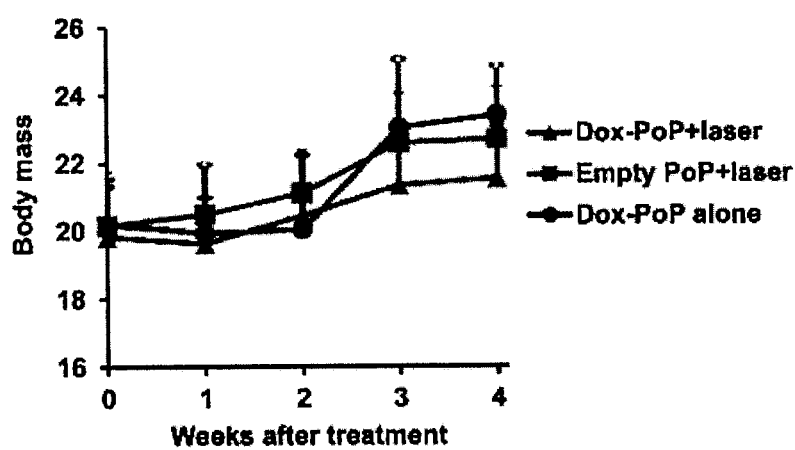
Figure 35:
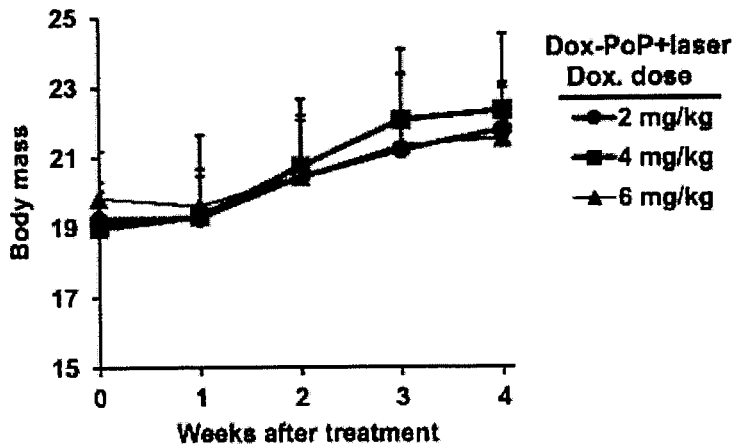

A dual tumor model was used to assess chemophototherapy-induced Dox accumulation in tumors, with one flank of tumor irradiated and the other used as a non-irradiated control. Tumor uptake of Dox immediately after laser treatment (250 mW/cm$^2$ for 40 min) was determined (FIG. 26B). A 5.6 fold increase of tumoral Dox accumulation was achieved in the irradiated tumors, compared to the non-irradiated tumors. However, the amount of Dox accumulation in both the non-irradiated and irradiated tumors (0.5 vs 1.0 µg/g, 2.6 vs 7.0 µg/g, respectively) was lower compared to the previously reported PEGylated PoP liposomes at an injection dose 5 mg/kg. The shorter circulating times for the non-PEGylated liposomes could be a contributing factor for the decreased deposition. Also, PoP can also induce a photodynamic mediated vascular permeabilization effect, which could contribute to the enhanced accumulation of nanoscale therapeutics. Thus the lower PoP dose (0.3 vs 2 mol %) in the non-PEGyated liposomes and diminished tumor vascular damage effects are likely reason for the relatively low Dox accumulation in the irradiated tumors. Dox distribution in key organs was determined immediately after laser treatment and revealed that most of the Dox was in kidney, spleen and liver, with a substantial amount of Dox-loaded PoP liposomes remaining in circulation after light treatment (FIG. 35A).

The anti-tumor efficacy of Dox loaded PoP (Dox-PoP) liposomes containing 5 mol % DOPC was assessed in mice bearing MIA PaCa-2 xenografts (FIG. 26C). 6 mg/kg Dox-PoP liposomes with light treatment was significantly more effective than the same dose of Dox-PoP liposomes without light treatment (median survival 80.5 vs 22.5 days, *P<0.001), or empty PoP liposomes with light treatment (median survival 80.5 vs 24.5 days, *P<0.001). 6 mg/kg Dox-PoP liposomes without light irradiation slightly delayed tumor growth compared to saline control (median survival 22.5 vs 19 days,*P<0.05). The equivalent dose of empty PoP liposomes with laser treatment was also marginally effective in tumor growth inhibition compared to saline control (median survival 24.5 days vs 19 days, **P<0.01). The enhanced efficacy of Dox-PoP liposomes with light treatment, compared to the other two monotherapies (chemotherapy with Dox-PoP alone or equivalent photodynamic therapy with empty PoP liposomes) could be due to the enhanced tumoral drug accumulation due to drug release and synergistic effects of chemotherapy and photodynamic therapy.

Given the effectiveness of the single-treatment chemophototherapy, a dose response of Dox-PoP liposomes with light was performed (FIG. 26D). Dox-PoP liposomes at just a 2 mg/kg Dox dose with laser treatment inhibited tumor growth compared to the saline control (median survival 23.5 vs 19 days, *P<0.05). 4 mg/kg Dox-PoP liposomes was not significant more effective than 2 mg/kg (median survival 28 vs 23.5 days). 6 mg/kg Dox-PoP liposomes was significantly more effective than 4 mg/kg (median survival 80.5 vs 28 days, **P<0.01), with 2 out of 6 mice permanently curved (33% cure rate). Based on the tumor volume data, on day 19 after phototreatment, 2 mg/kg Dox-PoP liposomes did not statistically significantly inhibit tumor growth compared to saline, while 4 mg/kg Dox-PoP liposomes was effective in tumor growth control (*P<0.05). 6 mg/kg Dox-PoP liposomes was significantly more potent than 4 mg/kg Dox-PoP liposomes (*P<0.05). Taken together, 4 mg/kg liposomes was effective in tumor growth inhibition, and 6 mg/kg Dox-PoP liposomes was more effective and 33% cure rate could be achieved. The body mass of mice revealed no weight loss during the course of treatment (FIG. 35B, 35C). There was no significant heating during the laser treatment, as the tumor surface temperature did not exceed 40° C. based on measurements with a thermal camera (data not shown).

Conclusion. Incorporation of unsaturated lipids, including DOPC, into PoP liposomes dramatically accelerated NIR light-triggered release. This allowed for the use of very low amounts of PoP (0.1-0.3 mol %) to trigger rapid light release while preserving serum stability in the absence of NIR irradiation. The mechanism of enhanced light release rate was related to the oxidation of DOPC by singlet oxygen. In the case of DOPC-free PoP liposomes, cholesterol oxidization led to light-triggered cargo release. Tumor inhibition using MIA Paca-2 xenografts demonstrated excellent chemophototherapy efficacy. The strategy of combining small amounts of unsaturated phospholipids together with stably bilayer-inserted photosensitizers (such as PoP) is a useful strategy for inducing rapid light-triggered intravascular release of therapeutics.

Experimental.

Materials: 1,2-distearoyl-sn-glycero-3-phosphocholine (DSPC), Cholesterol, 1,2-dioleoyl-sn-glycero-3-phosphocholine (18:1 (Δ9-cis) PC or DOPC), 1,2-distearoyl-sn-glycero-3-phosphoethanolamine-N-[amino(polyethylene glycol)-2000] (MPEG-2000-DSPE, PEG-lipid, or PEG) were obtained from Corden Pharma. (1, 2-dilinoleoyl-sn-glycero-3-phosphocholine (18:2(cis) PC), 1-stearoyl-2-linoleoyl-sn-glycero-3-phosphocholine (18:0-18:2 PC) and 1,2-dielaidoyl-sn-glycero-3-phosphocholine (18:1(trans) PC) were obtained from Avanti Polar Lipids. Other chemicals were obtained from Sigma unless noted otherwise. The PoP used was pyro-phospholipid and was synthesized as previously reported.

Liposome preparation: Unless noted otherwise, various formulations of liposomes were prepared by the same method as described herein. Unless otherwise noted, the finalized PoP liposome formulation in this study was [DSPC:DOPC:Cholesterol:PoP], [54.7:5:40:0.3], mol %, with a drug to lipid molar ratio 1:8. To generate 5 mL of PoP liposomes (20 mg/mL total lipids) of the indicated formations, lipids were dissolved in 1 mL ethanol at 60° C., followed by injection of 4 mL of 250 mM ammonium sulfate (pH 5.5) buffer at 60° C. The liposome solutions were then passed 10 times at 60° C. through sequentially stacked polycarbonate membranes of 0.2, 0.1, and 0.08 μm pore size using a high pressure nitrogen extruder (Northern Lipids). Free ammonium sulfate was removed by dialysis in an 800 mL solution composed of 10% sucrose and 10 mM histidine (pH 6.5) with at least 2 buffer exchanges. For sulforhodamine (SRB) loaded PoP liposomes, lipids of the indicated formulations were dissolved in ethanol and hydrated with 50 mM SRB, sonicated at 45° C. for 30 min. Liposomal fractions were collected through gel filtration method.

Cargo loading and characterization of PoP liposomes: Doxorubicin (Dox, LC Labs #D-4000) was loaded via the ammonium sulfate gradient method. Dox with a drug to lipid molar ratio of 1:8 was added into the lipid solutions and incubated at 60° C. for 1 h. Liposomes sizes and polydispersity index were determined by dynamic light scattering in PBS. Dox loading efficiency were determined by running 20 μL of liposomes (20 mg/ml lipids) diluted in 1 mL of PBS over a Sephadex G-75 column. 24×1 mL fractions were collected and Dox fluorescence in each fraction was measured using a TECAN Safire fluorescence microplate reader (excitation and emission wavelengths of 480 nm and 590 nm, respectively). Loading efficiency was determined as the percentage of drug in the liposome-containing fractions (first 3-8 fractions). Negative stained transmission electron microscopy (TEM) was performed using a JEM-2010 electron microscope with 1% uranyl acetate staining. Serum stability was performed by incubating PoP liposomes (20 mg/mL lipids) diluted 200 times in 50% sterile bovine serum (Pel-Freeze) at 37° C. for the indicated times. 0.25% Triton X-100 was added to read the total Dox fluorescence. Dox release was measured by florescence using the formula: % Dox release=$(F_{final}-F_{initial})/(F_{x-100}-F_{initial})\times 100\%$.

Light triggered drug release: Light-triggered release experiments were performed with a power-tunable 665 nm laser diode (RPMC Lasers) at the indicated fluence rate (310 mW/cm$^2$ or 250 mW/cm$^2$, as noted). Dox release was recorded in real time in a fluorometer (PTI). Irradiation was performed with PoP liposomes (20 mg/mL lipids) diluted 600 times in 50% sterile bovine serum (Pel-Freeze) at 37° C. Temperature was measured by inserting a K-type thermocouple probe directly into the irradiated solution. 0.25% Triton X-100 was added after laser irradiation to read the total fluorescence. Dox release was assessed by measuring Dox fluorescence before and after treatment with the formula: % Dox release=$(F_{final}-F_{initial})/(F_{x-100}-F_{initial})\times 100\%$. Inhibition of Dox release by sodium ascorbate was performed in a 96 microplate with 2 μL PoP liposomes (20 mg/mL lipids) diluted 100 times in PBS containing 5 mM of sodium ascorbate. Samples were irradiated at 250 mW/cm$^2$ for 3 min. Inhibition of Dox release by sodium sulfite was performed in a cuvette with 5 μL PoP liposomes (20 mg/mL lipids) diluted 600 times in PBS containing 25 mM sodium sulfite. Samples were irradiated at 310 mW/cm$^2$.

Singlet oxygen determination: Singlet oxygen sensor green (SOSG) reagent (Life Technologies #S-36002) was employed for the detection of singlet oxygen generated by pyro-phospholipid during irradiation. SOSG fluorescence (exc./em. 504 nm/525 nm) was recorded during irradiation in a fluometer (PTI). Light irradiation was performed in PBS containing 500 nM SOSG and Dox-loaded PoP (420 nM PoP) liposomes. PBS containing 5 mM sodium ascorbate or 25 mM sodium sulfite were employed to inhibit the singlet oxygen generation.

Liquid chromatography-mass spectrometry (LC-MS): Dox loaded PoP liposomes (20 mg/mL lipids, [DSPC:DOPC:Cholesterol:PoP], [54.7:5:40:0.3], mol %) were diluted 100 times in PBS and irradiated (310 mW/cm$^2$) for 0.5, 1, 2, 4 min for oxidation kinetics. For oxidization inhibition, samples were irradiated for 4 min at 310 mW/cm$^2$ in PBS containing 5 mM sodium ascorbate. 1 mL of treated liposomes was then extracted with a methanol:chloroform 1:2 (v/v) solution. The organic layer was collected and the aqueous layer was re-extracted. The organic layers were combined and dried under vacuum and stored in −80° C. Lipids were re-suspended in chloroform for LC-MS use. LC-MS data acquisition was performed using LC-ESI-QTOF [Agilent 1260 HPLC coupled to Agilent 6530 Accurate-Mass Quadrupole Time-of-Flight instrument (Agilent Technologies, Santa Clara, Calif., USA)] in positive electrospray ionization mode. Chromatographic separation was achieved using a Luna C5 reversed phase column (5 μm, 4.6 mm×50 mm, Phenomenex) with a C5 reversed phase guard cartridge. Mobile phase A and B were 95:5 water:methanol (v/v) and 60:35:5 isopropanol:methanol:water, respectively. Each mobile phase was supplemented with 0.1% (v/v) formic acid and 5 mM ammonium formate. The gradient started after 3 min at 0% B and then increased to 100% B over 10 min followed by 100% B for 7 min before equilibration for 8 min at 0% B. The flow rate was 0.5 mL/min. A DualJSI fitted electrospray ionization (ESI) source was used. Capillary and fragmentor voltages were set to 3500 and 175 V. Drying gas temperature was 350° C. with a flow rate of 12 L/min. Data was collected using an m/z range of 50-1700 in extended dynamic range.

For targeted analysis, the corresponding m/z for each ion (for DOPC m/z=786.6007, [M+H]$^+$, and for DSPC m/z=790.6320, [M+H]$^+$) was extracted in MassHunter Qualitative Analysis (version B.06.00, Agilent Technologies). Peak areas for each ion in extracted ion chromatogram were manually integrated and were presented as ion counts. DOPC and DSPC were confirmed by their MS/MS fragmentation patterns. MS/MS experiments were carried out in a similar way. Different collision energies were used to get optimal ionization. Fragmentation patterns were observed at 15 V, 35 V and 55 V. In order to identify emerging species after irradiation, raw data obtained was imported into MassHunter Profinder (version B.06.00, Agilent Technologies) for peak alignment. Statistical analysis and filtering of the newly identified species were carried out in Mass Profiler Professional (MPP, version 12.6.1, Agilent Technologies).

Light-induced calcein encapsulation: 10 μL of empty PoP liposomes (20 mg/mL lipids) were diluted 20 times in PBS in a microplate well. Laser irradiation was performed at 665 nm and 250 mW/cm$^2$ for 3 min at room temperature. Calcein (50 mM) was added before or after irradiation as indicated. Liposome samples were loaded onto a Sephadex G-75 column immediately after treatment (FIG. 25C). For the kinetics of calcein encapsulation into pre-irradiated empty PoP liposomes, calcein was added immediately after, 1 min, 10 min, 30 min or 60 min after irradiation. Samples were then added to G-75 columns after incubation at room temperature for 3 min (FIG. 25D). Alternatively, calcein was added before irradiation (250 mW/cm$^2$ for 3 min) and incubated at room temperature for 0 min, 1 min, 10 min, 30 min and 60 min (FIG. 25E). Calcein encapsulation efficiency was determined by gel filtration with a Sephadex G-75 column. 16×0.5 mL fractions were collected, calcein (485 nm/525 nm) and PoP (420 nm/670 nm) fluorescence were read with a TECAN Safire fluorescence microplate reader. Calcein/PoP ratios in the liposomal fractions (6-9 fractions) were calculated by simple division.

Pharmacokinetics and biodistribution: Female mice (female CD-1, 18-20 g, Charles River) were intravenously injected via tail vein with Dox loaded DOPC-containing PoP liposomes (10 mg/kg Dox), n=4. Small blood volumes were sampled at sub-mandibular and retroorbital locations at 0.5, 2, 4, 10, 24 and 28 h post injection. Blood was centrifuged at 1,500× g for 15 min. 10 μL serum was collected and diluted 100 times in extraction buffer (0.075 N HCl, 90% isopropanol). Samples were stored at −20° C. overnight. Samples were removed and centrifuged for 15 min at 10,000× g. Supernatants were collected and analyzed by fluorescence. Dox concentrations were determined by a standard curve. Noncompartmental pharmacokinetics parameters were analyzed by PKsolver.

For biodistribution, female nude mice (Jackson labs, #007850) were inoculated with 5×10$^6$ MIA Paca-2 cells on both flanks (n=4). 10 min following intravenous injection with 6 mg/kg Dox loaded DOPC-containing PoP liposomes, mice were anesthetized via inhalation of isoflurane and tumors (8-10 mm) on one flank were irradiated at 250 mW/cm$^2$ for 40 min, tumors on the other flank were used as non-irradiated controls. Mice were sacrificed immediately after irradiation. Tumors and key organs were collected and washed in PBS, weighted, and homogenized in nuclear lysis bufffer [0.25 mol/L sucrose, 5 mmol/L Tris-HCl, mmol/L MgSO$_4$, 1 mmol/L,CaCl (pH 7.6)]. Dox was extracted overnight in 0.075 N HCl 90% isopropanol and quantified as described above.

Tumor growth inhibition: Five week old female nude mice (Jackson Labs, #007805) were inoculated with 5×10$^6$ MIA Paca-2 cells on one flank. When tumor sizes reached 6-8 mm, mice were randomly grouped into four groups with 5-6 mice per group: (1) Dox-PoP with laser; (2) Empty PoP with laser; (3) Dox-PoP without laser; (4) Saline. 200 μL of Dox-PoP (6 mg/kg Dox, 0.25 mg/kg PoP) or empty PoP liposomes (0.25 mg/kg PoP) were I.V. injected through the tail vein. For the dose response experiment, another two groups Dox-PoP (2 mg/kg Dox)+laser or Dox-PoP (4 mg/kg Dox)+laser were included. 10 min following I.V. injection, mice were anesthetized via inhalation of isoflurane. Irradiated tumors were treated with 665 nm laser at 250 mW/cm$^2$ for 40 min (600 J/cm$^2$). Tumor temperatures during laser treatment were monitored with a thermal camera. Tumor sizes were recorded 2-3 times per week by measuring three tumor dimensions using a caliper. Tumor volumes were calculated with the ellipsoid formula: Volume=π·L·W$^2$/6, where L and W are the length and width of the tumor, respectively. Body weights of the mice were monitored for four weeks. Mice were sacrificed when the tumor volume exceeded 10 times initial volume or at the end of the study period (90 days).

Statistical analysis Data were analyzed by GraphPad Prism (version 5.01). Kaplan-Merier survival cures were analyzed with log-rank (Mantel-Cox) test. Median survival was defined as the time at which the staircase survival curve crosses 50% survival. Tumor volume curves were analyzed by one-way ANOVA test followed by Tukey's multiple comparison test. Differences were considered significant at P<0.05. (*P<0.05, P<0.01, *P<0.001).

EXAMPLE 4

This example further describes the preparation of PoP-liposomes with different PoPs, loading of the PoP-liposomes, and selective/sequential release of cargo form the PoP-liposomes.

Figure 36:
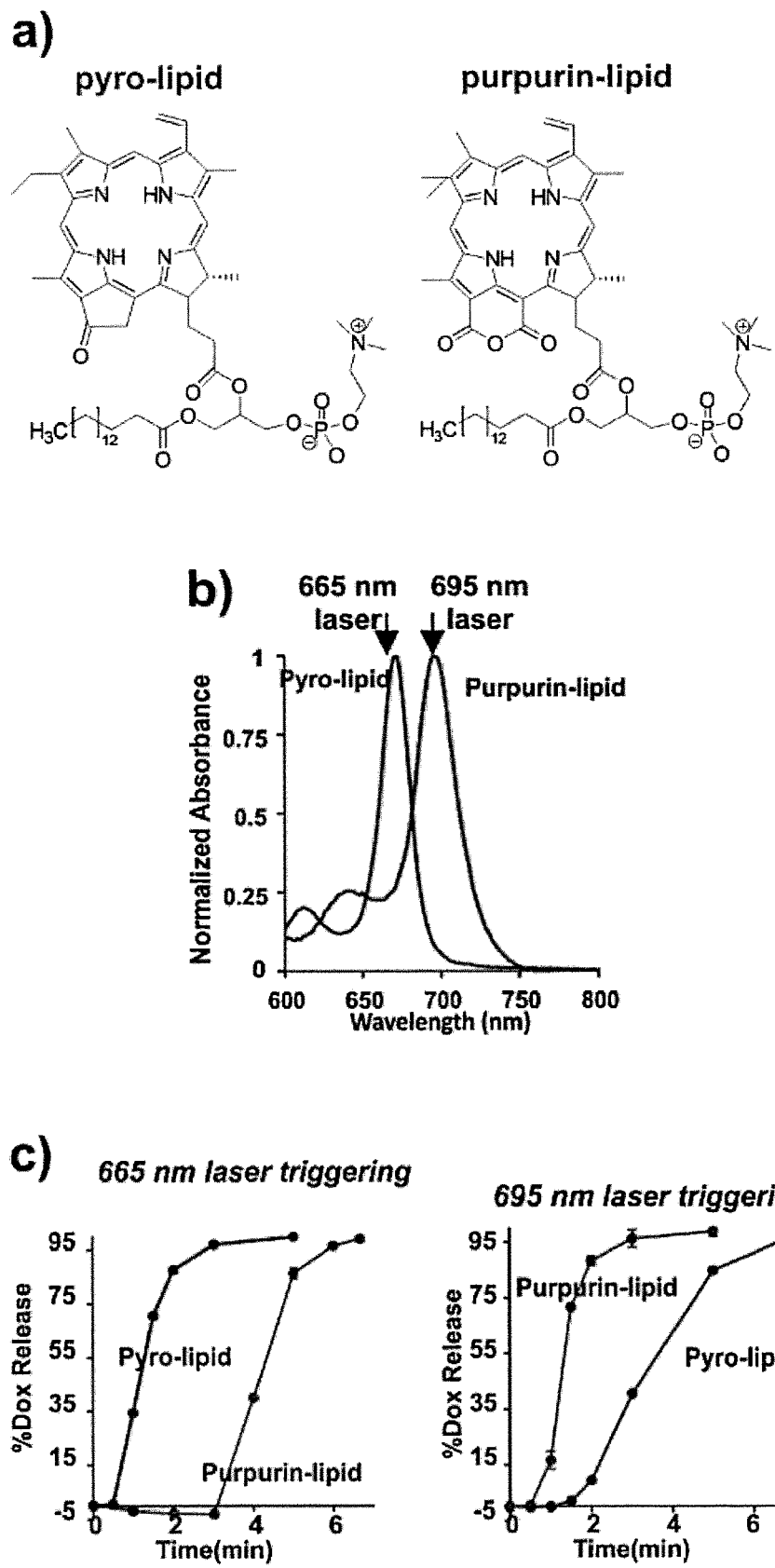
FIG. 36. Development of multi-color, multi-channel PoP liposomes. a) Structures of pyro-PoP and purpurin-PoP. b) Absorption spectra in water of indicated PoP liposomes. Wavelength of lab laser excitation is indicated. c) Dox release from pyro or purpurin-PoP under either 665 or 695 nm laser.

Development of different types of PoP for light-activated PoP liposomes. A new type of PoP based on purpurin-18 was developed, which differs in structure from pyro-phospholipid based on the exocyclic ring (FIG. 36a). Purpurin-18 is commercially available and was readily esterified to the lyso-lipid. Purpurin-PoP purity was over 95% and identity was confirmed with mass spectrometry. Both pyro- and purpurin-PoP liposomes could be formed with a molar ratio of PoP:PEG-lipid:CHOL:DSPC of 2:5:40:53 and exhibited spectrally resolvable absorption. As shown in FIG. 36b, the laser diodes (665 nm and 695 nm) provided a good degree of separation of the two colors of PoP liposomes.

Next, these two types of PoP liposomes were successfully loaded with doxorubicin via sulfate gradient and subjected to laser irradiation from either the standard 665 nm laser (used for all other data in this proposal) or a 695 nm laser diode. As shown in FIG. 36c, the 665 nm laser provided a degree of selective permeabilization for the pyro-phospholipid PoP liposomes, whereas the 695 nm laser more efficaciously permeabilized the purpurin-lipid PoP liposomes. Although in both cases, release did eventually occur for both types of liposomes, by halting laser irradiation after just a couple of minutes selective release is achieved in this system.

EXAMPLE 5

This example describes the release of passively loaded cargo from serum-stable PoP liposomes.

Figure 37:
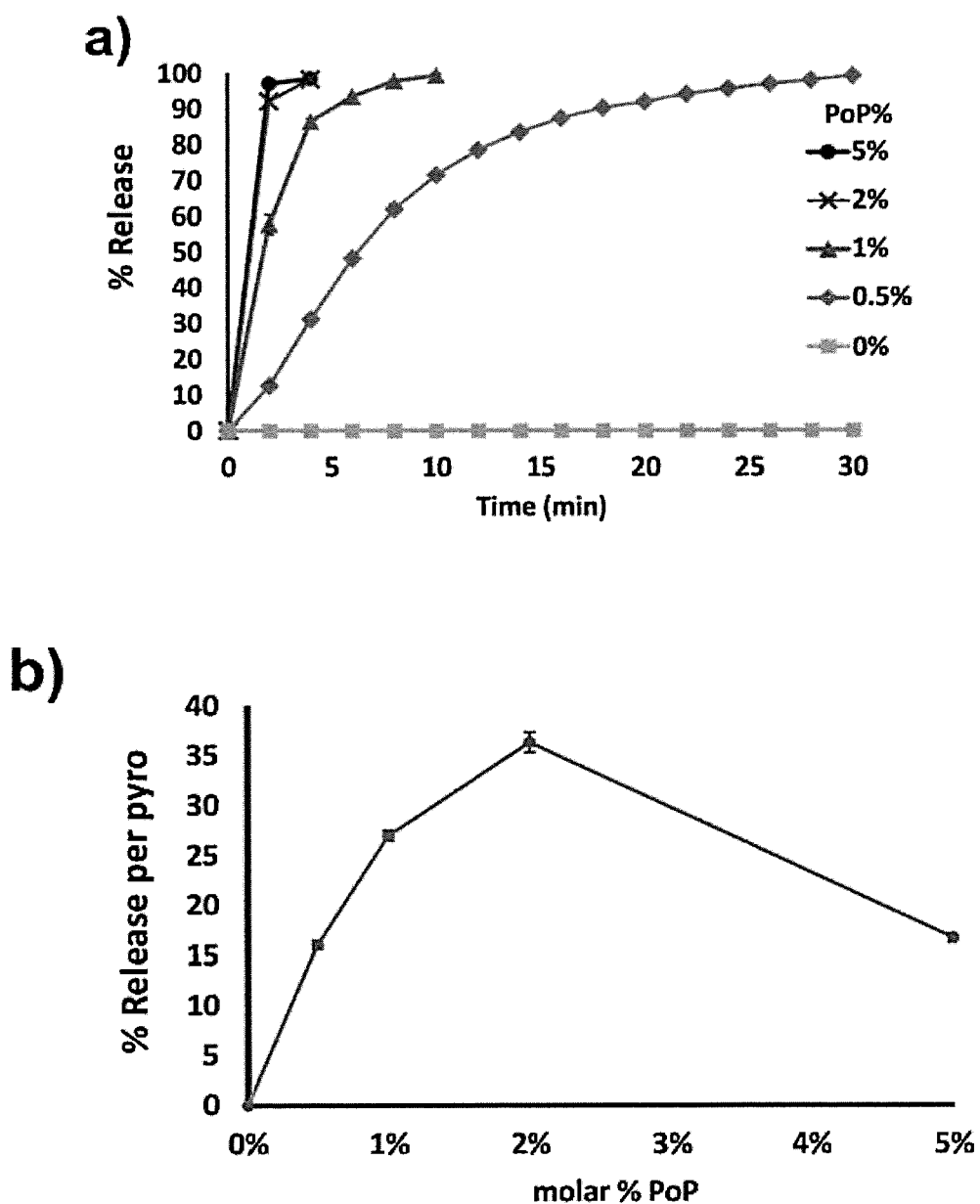
FIG. 37. a) Addition of varying amounts of Pyro-phospholipid to liposome increases the release of a passively loaded cargo, the hydrophilic dye SRB. b) Release rate normalized by the amount of pyro-phospholipid present.
Figure 38:
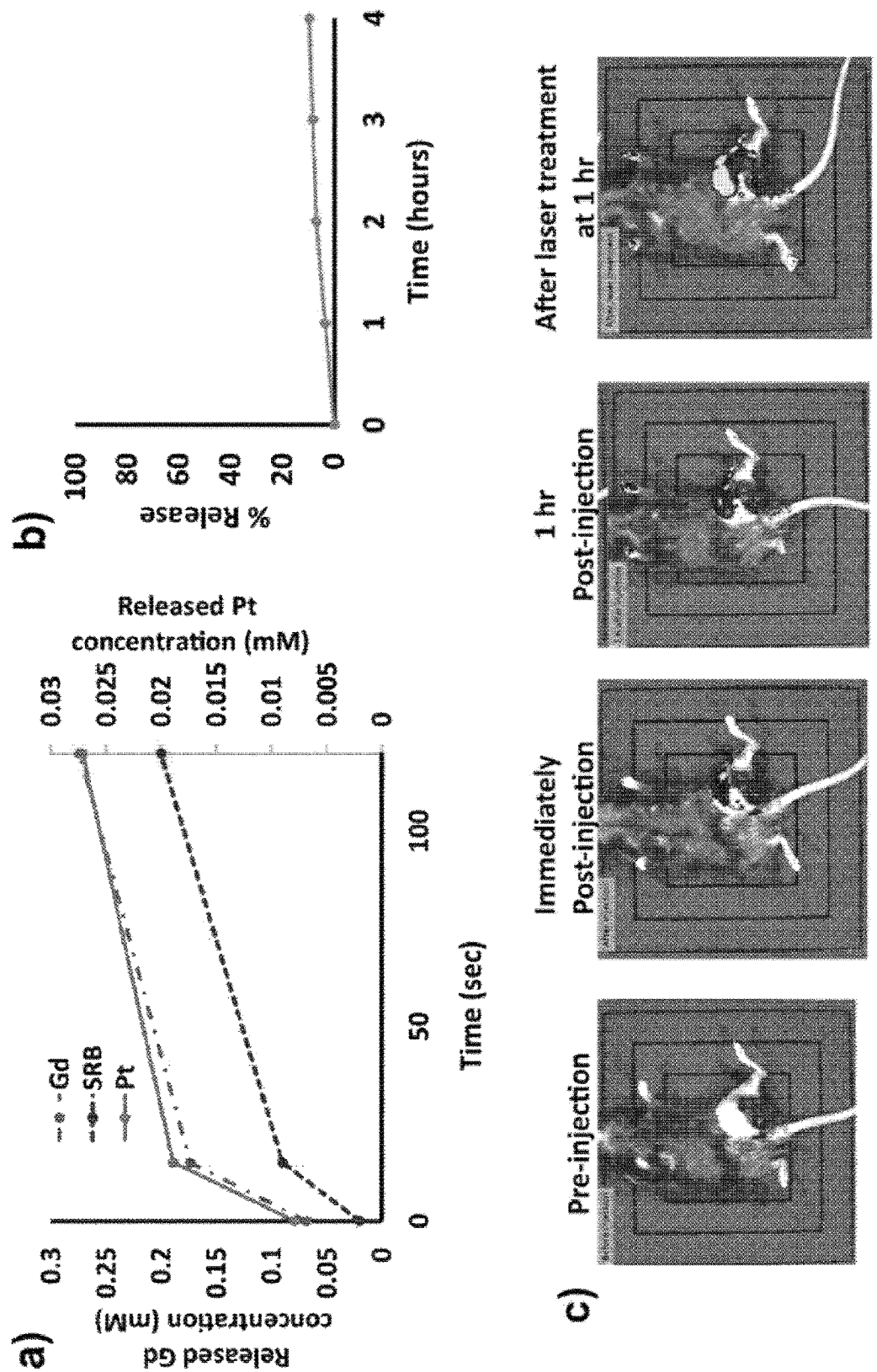
FIG. 38. PoP liposomes (2 molar % PoP) were simultaneously loaded with Gd-DTPA, SRB and oxaliplatin. Free cargo was removed and liposomes were injected intratumorally into mice bearing B16F10 melanomas. SRB fluorescence was used to 1) guide injections and 2) demonstrate distribution within the tumor and 3) monitor release. Gd-DTPA is intended to be used for MR contrast and oxaliplatin exerts a therapeutic effect. a) Release of Gd, PT, and SRB triggered by 665 nm laser irradiation as a function of time. b) SRB release in the absence of NIR light. c) Images of mice pre-injection, immediately post-injection, 1 hr. post-injection, and after laser treatment at 1 hr.

PoP liposomes were formed with a molar ratio of [50:5:2:32:11] [CHOL:PEG2K-DSPE:Pyro-phospholipid:DSPC:DOPC] and were hydrated with 50 mM sulforhodamine B, a hydrophilic dye. After separating the free dye, liposomes were subjected to laser irradiation. As shown in FIG. 37, PoP conferred release of the passively loaded cargo and 2% PoP was determined to be optimal. 38

EXAMPLE 6

This example describes the release of actively-loaded irinotecan from PoP liposomes.

Figure 39:
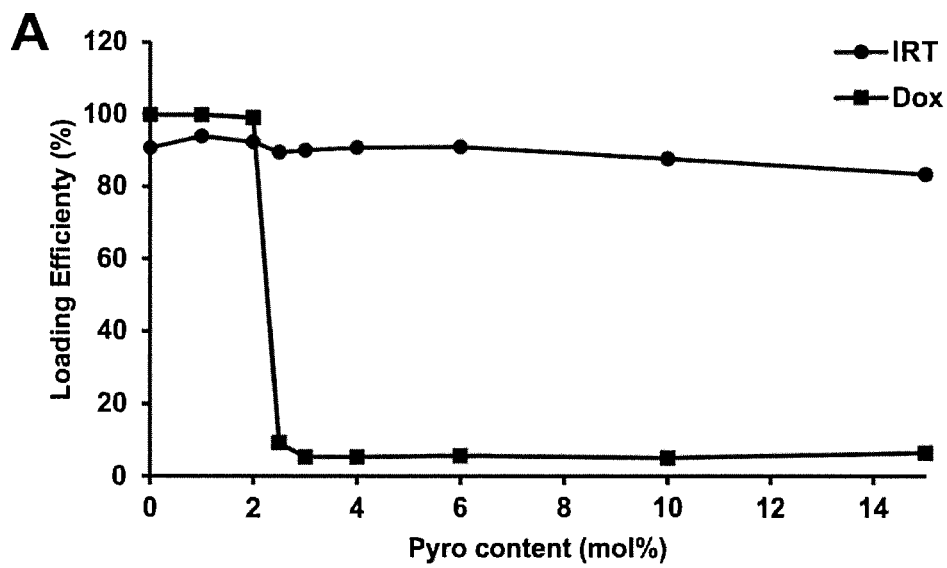
FIG. 39. Drug Loading and Release. A) Pyro-phospholipid PoP was titrated into liposomes consisting of DSPC:DSPE-PEG2000:Chol (60:5:35 molar ratio) replacing DSPC to compare the effects of pyro-phospholipid PoP content on Dox and IRT loading. B) Release of Dox and IRT from liposomes consisting of 2% pyro-phospholipid under 665 nm laser irradiation.
Figure 39:
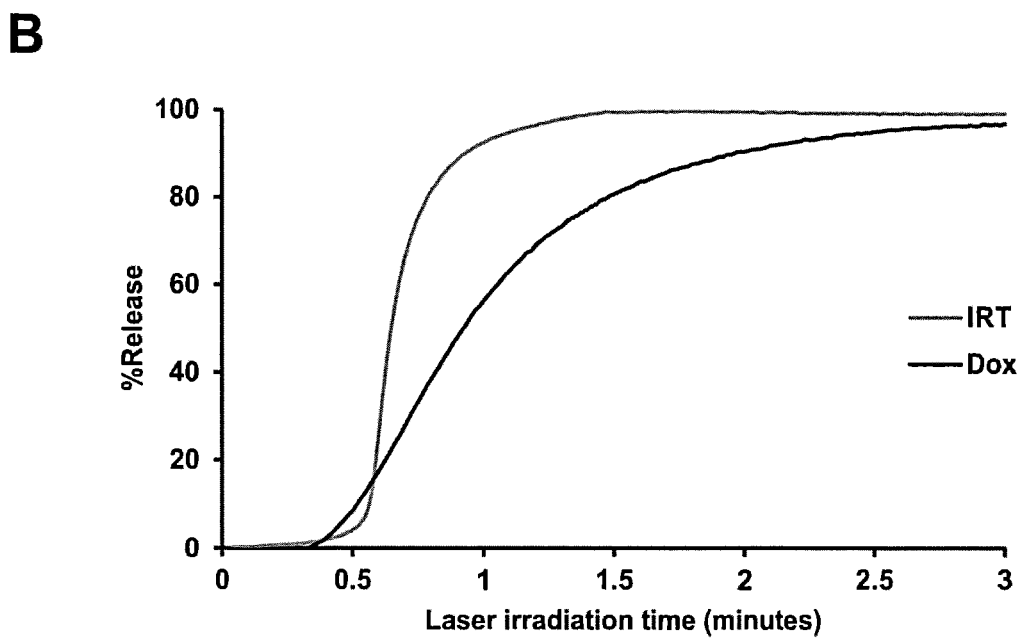
Figure 40:
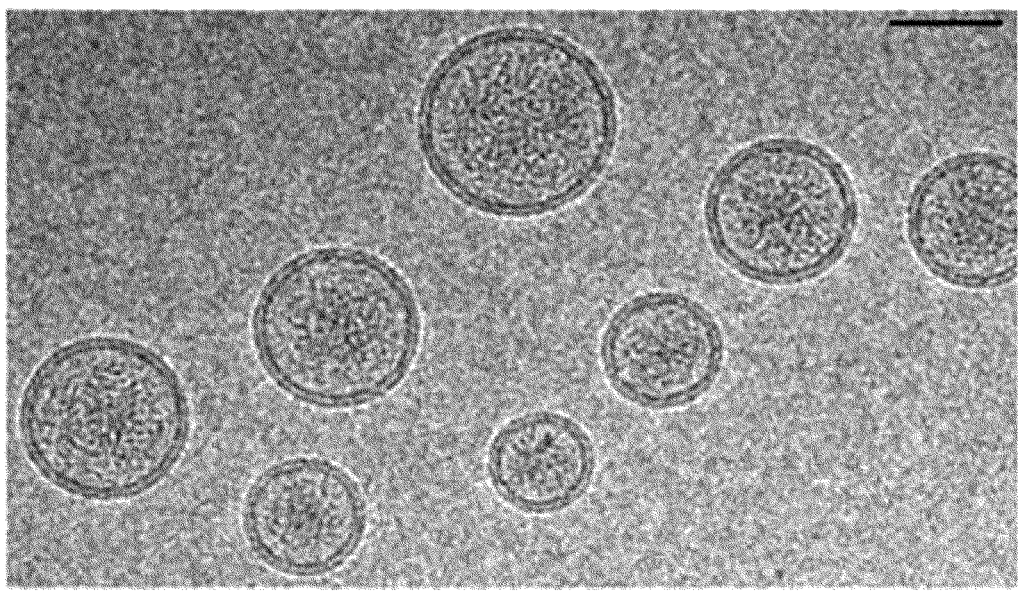
FIG. 40. Effects of drug on liposomes morphology. Cryo-TEM images of IRT (A) and Dox (B) loaded PoP-liposomes consisting of DSPC:DSPE-PEG2000:Pyro-phospholipid:Chol (58:5:2:35).
Figure 40:
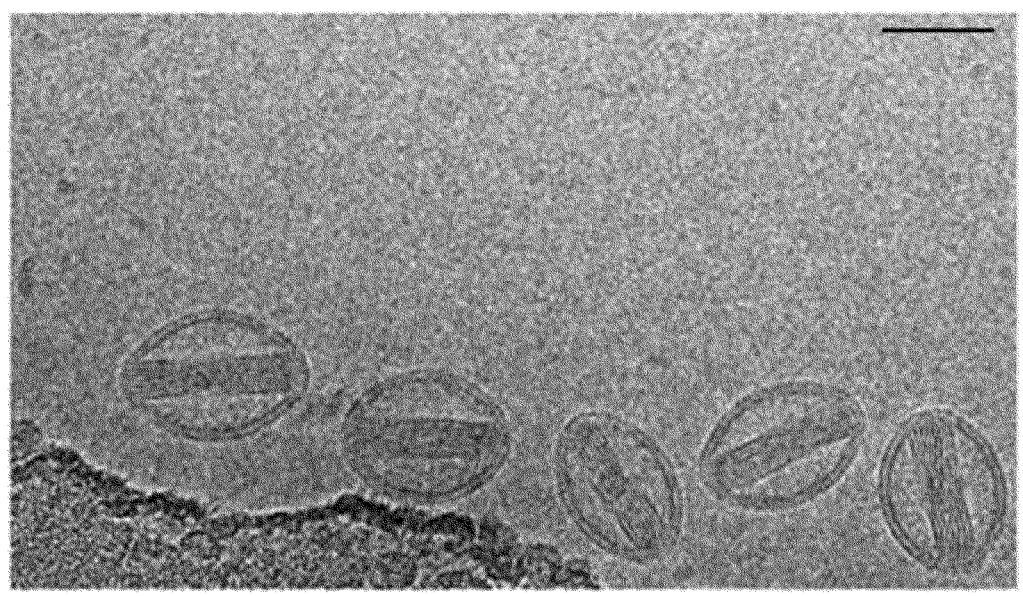

Using a Doxil-like liposome formulation and replacing some of the DSPC with pyro-phospholipid can produce liposomes which could stably load Dox and exhibit similar pharmacokinetics to that of the pyro-phospholipid free liposomes. However there is a maximum amount of pyro-phospholipid which could be added to the liposomes before Dox loading became impossible. This amount was found to be a function of the cholesterol content. When the cholesterol content was 35 mol % Dox could only be loaded into liposomes containing 2 mol % or less pyro-phospholipid. At 45 mol % cholesterol Dox could be loaded to liposomes containing 8 mol % pyro-phospholipid. This was suspected to be due to the formation of Dox crystals in the liposomes which caused them to stretch and destabilize the bilayer. This trend was not found to be present when pyro-phospholipid containing liposomes were loaded with IRT (irinotecan). Liposomes were made using DSPC:DSPE-PEG2000:Cholesterol (mole ratio 60:5:35) and pyro-phospholipid was titrated in replacing DSPC. We found that while Dox could not be loaded into liposomes containing more than 2 mol % pyro-phospholipid, IRT however did not show such limitation and could be loaded into liposomes containing as much as 15 mol % pyro-phospholipid. (FIG. 39A). The light release of IRT from these liposomes was also tested. Using 2 mol % pyro, which was previously found to be the optimum for Dox release, IRT release was compared to Dox release in 50% serum. The results showed that IRT release from PoP-liposomes is faster than that of Dox (FIG. 39B). To help understand these differences between IRT and Dox cryo-TEM images of IRT and Dox loaded liposomes comprising of DSPC:DSPE-PEG2000:Pyro-phospholipid:Cholesterol (mole ratio 58:5:2:35) were taken. The images showed that IRT loaded liposomes did not form large crystals as Dox, nor did they have an effect on the shape of the liposomes. Instead IRT formed crystals which occupied the entirety of the liposomes core. (FIG. 40). This demonstrates that IRT does not alter the morphology of the liposomes suggesting the poor loading of Dox in pyro-phospholipid containing liposomes is likely do to destabilization of the bilayer due to stretching induced by the formation of Dox crystals. It additionally shows that the faster release of IRT may be due to more diffused crystals which can dissolve more readily when the liposome bilayer is permeabilized, than Dox which is a more compact crystal.

While the disclosure has been described with reference to specific embodiments and examples, it should be understood by those having skill in the art that various changes in form and detail may be made therein without departing from the spirit and scope of the present disclosure as disclosed herein.

The invention claimed is:

1. A composition comprising nanovesicles, said nanovesicles having a bilayer, wherein the bilayer of the nanovesicles comprises 0.1 to 5 mol % porphyrin-phospholipid (PoP), 30 to 45 mol % sterol, 45 to 61.5 mol % of one or more phospholipids which is/are not conjugated to porphyrin, and optionally 1 to 6 mol % polyethylene glycol-lipid (PEG-lipid), wherein the porphyrin-phospholipid has the following structure (pyro-phospholipid):

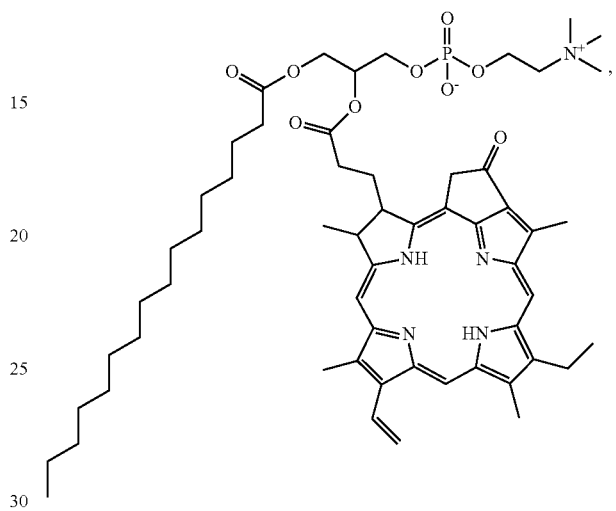

and wherein the one or more phospholipids which is/are not conjugated to the porphyrin are chosen from 1,2-distearoyl-sn-glycero-3-phosphocholine (DSPC), 1,2-distearoyl-sn-glycero-3-phosphoethanolamine (DSPE), 1,2-dihexadecanoyl-sn-glycero-3-phosphate (DPPA), 1,2-distearoyl-sn-glycero-3-phospho-(1'-rac-glycerol) (DSPG), hydrogenated L-α-phosphatidylcholine (HSPC), 1,2-dioleoyl-sn-glycerol-3-phosphocholine (DOPC), 1,2-dioleoyl-3-trimethylammonium-propane (DOTAP), 1,2-dipalmitoyl-sn-glycero-3-phosphocholine (DPPC), and 1,2-dimyristoyl-sn-glycero-3-phosphocholine (DMPC), and wherein the nanovesicles are loaded with cargo comprising doxorubicin or irinotecan.

2. The composition of claim 1, wherein the sterol is cholesterol.

3. The composition of claim 1, wherein the one or more phospholipids comprises DSPC and/or DOPC.

4. The composition of claim 1, wherein the bilayer comprises 1.0-3.0 mol % porphyrin-phospholipid, 35 to 45% cholesterol, with the remainder being made up by one or more phospholipids not conjugated to a porphyrin.

5. The composition of claim 3, wherein the nanovesicle bilayer comprises a composition selected from the group consisting of:
 i) DSPC:PEG-lipid:cholesterol:PoP::53:5:40:2;
 ii) DSPC:DOPC:Cholesterol:PoP::54.7:5:40:0.3;
 iii) Cholesterol:DSPC:DOPC:PEG-lipid:PoP::50:32:11:5:2; and
 iv) DSPC:PEG-lipid:Cholesterol:PoP::60:5:35:2.

6. The composition of claim 1, wherein the nanovesicles are present in a carrier, wherein the carrier is a physiological buffer.

7. The composition of claim 3, wherein the phospholipid comprises DSPC and DOPC, wherein the DOPC is present from 0.1 to 5 mol %.

8. The composition of claim 1, wherein the cargo molecule is Doxorubicin.

9. The composition of claim 1, wherein the cargo is present in the aqueous compartment of the nanovesicles.

10. The composition of claim 1, wherein the phospholipid to cargo drug molar ratio is from 10:1 to 5:1.

11. The composition of claim 1, wherein the composition further comprises additional nanovesicles, wherein the additional nanovesicles have a bilayer comprising 0.1 to 5 mol % purpurin-phospholipid, 30 to 45 mol % sterol, 45 to 61.5 mol % of one or more phospholipids which is/are not conjugated to porphyrin, and optionally 1 to 6 mol % polyethylene glycol-lipid (PEG-lipid).

12. A method of delivering a cargo to a desired location comprising the steps of:
    a) administering to an individual the composition of claim 1 such that it enters the circulatory system;
    b) allowing the nanovesicles to reach the desired location; and
    c) exposing the nanovesicles to near infrared radiation of wavelength from 650 to 1000 nm such that the cargo is released from the nanovesicles.

13. The method of claim 12, wherein the nanovesicles comprise an imaging agent and the method further comprises imaging the individual after administration and before exposing the nanovesicles and determining that the nanovesicles have reached the desired location.

14. The method of claim 12, wherein the individual is a human or non-human mammal.

15. The method of claim 12, wherein the nanovesicles are exposed to a wavelength of 658, 665, or 671 nm.

16. The method of claim 12, wherein the nanovesicles are exposed to near infrared radiation for up to 30 minutes.

17. The method of claim 12, wherein step c) is carried out as multiple exposures to the near infrared radiation.

18. A method of controlled release of cargo comprising:
    a) providing a composition of claim 1, wherein there is no detectable release of the cargo at temperatures from room temperature to 37° C.; and
    b) exposing the composition to a light of wavelength of 650-1000 nm from a laser which has a power of from 10 to 350 mW/cm$^2$,
wherein at least 90% of the cargo is released within 1 to 8 minutes upon exposure to light in step b).

19. The method of claim 18, wherein the phospholipid not conjugated to porphyrin is DSPC and DOPC, and wherein DOPC is present from 0.1 to 5 mol %.

20. The method of claim 18, wherein the pyro-phospholipid is present from 0.1 to 1.0 mol %, and wherein at least 50% of the cargo is released within 1 minute.

21. The composition of claim 1, wherein the cargo molecule is irinotecan.

22. The composition of claim 3, wherein the bilayer of the nanovesicle comprises DSPC and 1.5-2.5 mol % pyro-phospholipid.

* * * * *